(12) United States Patent
Boudreaux

(10) Patent No.: US 10,194,976 B2
(45) Date of Patent: Feb. 5, 2019

(54) LOCKOUT DISABLING MECHANISM

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 849 days.

(21) Appl. No.: 14/468,037

(22) Filed: Aug. 25, 2014

(65) Prior Publication Data

US 2016/0051317 A1    Feb. 25, 2016

(51) Int. Cl.
*A61B 18/14* (2006.01)
*H01H 9/28* (2006.01)
(Continued)

(52) U.S. Cl.
CPC ......... *A61B 18/1445* (2013.01); *H01H 9/286* (2013.01); *A61B 2017/00367* (2013.01);
(Continued)

(58) Field of Classification Search
CPC ............ A61B 18/1445; A61B 18/1442; A61B 2017/00367; A61B 2017/2923; A61B 2018/00607; A61B 2018/0091; A61B 2018/1455; A61B 2018/1452; A61B 17/29; A61B 2017/2901; A61B 2017/2902; A61B 2017/2903; A61B 17/2909;
(Continued)

(56) References Cited

U.S. PATENT DOCUMENTS 2,366,274 A    1/1945 Luth et al.
2,458,152 A    1/1949 Eakins
(Continued)

FOREIGN PATENT DOCUMENTS

CN    2868227 Y    2/2007
CN    102834069 A    12/2012
(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
(Continued)

*Primary Examiner* — Roland Hupczey, Jr.

(57) ABSTRACT

A surgical instrument is disclosed. The surgical instrument has a handle assembly. The handle assembly has a trigger operatively coupled to a firing plate, an energy button configured to deliver energy to at least one electrode, a lockout element operatively coupled to the energy button, the lockout element configured to prevent operation of the firing plate, and a lockout disabling mechanism configured to disable the lockout element, the lockout disabling mechanism operable between a first position and a second position. When the lockout disabling mechanism is located in the first position, the lockout element is enabled and can be unlocked by the energy button, and wherein when the lockout disabling mechanism is in the second position, the lockout element is disabled.

26 Claims, 49 Drawing Sheets

(51) Int. Cl.
 *A61B 17/00* (2006.01)
 *A61B 17/29* (2006.01)
 *A61B 18/00* (2006.01)
 *A61B 90/00* (2016.01)

(52) U.S. Cl.
 CPC ............... *A61B 2017/2923* (2013.01); *A61B 2018/0091* (2013.01); *A61B 2018/00607* (2013.01); *A61B 2018/1455* (2013.01); *A61B 2090/0801* (2016.02); *A61B 2090/08021* (2016.02); *H01H 2215/00* (2013.01); *H01H 2239/03* (2013.01); *H01H 2300/014* (2013.01)

(58) Field of Classification Search
 CPC .... A61B 2017/2912; A61B 2017/2913; A61B 2017/2915; A61B 2017/2925; A61B 2017/2943; A61B 17/295; A61B 17/28; A61B 17/2833; A61B 17/285; A61B 2017/2946; H01H 2215/00
 USPC .......................................................... 606/52
 See application file for complete search history.

(56) References Cited

U.S. PATENT DOCUMENTS

| | | |
|---|---|---|
| 2,510,693 A | 6/1950 | Green |
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,314,559 A | 2/1982 | Allen |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |

(56) References Cited

U.S. PATENT DOCUMENTS

| | | |
|---|---|---|
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A * | 2/2000 | Williamson, IV ............ A61B 17/07207 606/40 |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| 6,409,722 B1 | 6/2002 | Hoey et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 | 5/2003 | Paton et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,610,060 B2 | 8/2003 | Mulier et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,682,501 B1 | 1/2004 | Nelson et al. |
| 6,695,840 B2 | 2/2004 | Schulze |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |

(56) References Cited

U.S. PATENT DOCUMENTS

| | | | |
|---|---|---|---|
| 7,118,570 B2 | 10/2006 | Tetzlaff et al. |
| 7,125,409 B2 | 10/2006 | Truckai et al. |
| 7,131,970 B2 * | 11/2006 | Moses ............... A61B 18/1442 |
| | | | 606/205 |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |

(56) References Cited

U.S. PATENT DOCUMENTS

| | | |
|---|---|---|
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 9,522,029 B2 | 12/2016 | Yates et al. |
| 2002/0022836 A1 | 2/2002 | Goble et al. |

(56) References Cited

U.S. PATENT DOCUMENTS

| | | |
|---|---|---|
| 2002/0049551 A1 | 4/2002 | Friedman et al. |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0113827 A1* | 5/2005 | Dumbauld ......... A61B 18/1445 606/45 |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208336 A1* | 9/2007 | Kim ................... A61B 18/1445 606/41 |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0071525 A1* | 3/2011 | Dumbauld ......... A61B 18/1445 606/51 |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0288369 A1* | 11/2011 | Ginnebaugh ........ A61B 18/085 600/36 |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |

(56) References Cited

U.S. PATENT DOCUMENTS

| | | |
|---|---|---|
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0180281 A1 | 6/2014 | Rusin |
| 2014/0194874 A1 | 7/2014 | Dietz et al. |
| 2014/0194875 A1 | 7/2014 | Reschke et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 4300307 A1 | 7/1994 |
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2529681 A1 | 12/2012 |

(56) References Cited

FOREIGN PATENT DOCUMENTS

| | | |
|---|---|---|
| EP | 1767164 B1 | 1/2013 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H 08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, Engineering Formulas § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, Integrated Circuit Engineering, Addison-Wesley Publishing, Reading, MA (1979). (book—not attached).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200S, (2012), p. 7, 12 pages, accessed Mar. 31, 2014 at http://www.erbe-med.com/erbe/media/Marketingmaterialien/85140-170_ERBE_EN_VIO_200_S__D027541.

Jang, J. et al. "Neuro-fuzzy and Soft Computing." Prentice Hall, 1997, pp. 13-89, 199-293, 335-393, 453-496, 535-549.

(56) References Cited

OTHER PUBLICATIONS

Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
U.S Appl. No. 15/265,293, filed Sep. 14, 2016.
U.S. Appl. No. 15/258,570, filed Sep. 7, 2016.
U.S. Appl. No. 15/258,578, filed Sep. 7, 2016.
U.S. Appl. No. 15/258,586, filed Sep. 7, 2016.
U.S. Appl. No. 15/258,598, filed Sep. 7, 2016.

\* cited by examiner

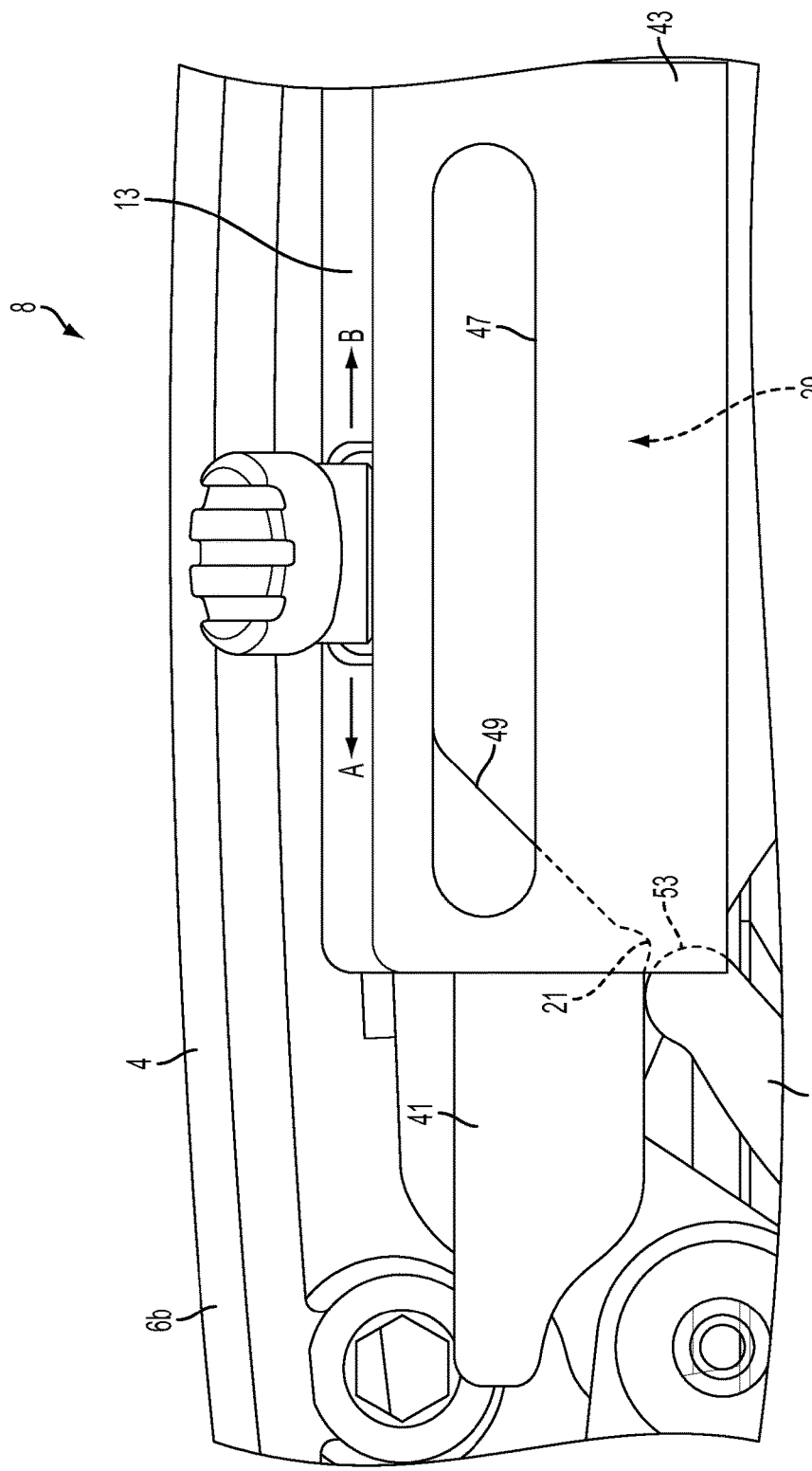

LOCKOUT DISABLING MECHANISM

CROSS-REFERENCE TO RELATED APPLICATIONS

This application is related to U.S. patent application Ser. No. 14/467,883, titled "SIMULTANEOUS I-BEAM AND SPRING DRIVEN CAM JAW CLOSURE MECHANISM," filed Aug. 25, 2014 now U.S. Publication No. 2016/0051315 and U.S. patent application Ser. No. 14/467,990, titled "ELECTROSURGICAL ELECTRODE MECHANISM," filed Aug. 25, 2014 now U.S. Publication No. 2016/0051316; each of which is incorporated herein by reference in its entirety.

INTRODUCTION

The present disclosure is related generally to electrosurgical devices with various mechanisms for clamping and treating tissue. In particular, the present disclosure is related to electrosurgical devices with a knife lockout disabling feature.

Conventional electrosurgical devices have a knife lockout that prevents the user from firing the knife unless the energy is activated. The energy button and lockout button are the same component. This feature, however, prevents a user of a conventional electrosurgical device from turning off or otherwise disabling the knife lockout feature such that the device can be operated faster. Also, conventional electrosurgical devices make it difficult to unlock the knife when the fire trigger is forced to the closed position. Thus, when the knife eventually comes unlocked, the knife jumps forward due to the potential energy developed under the compressive forces. Such jump of the knife is undesirable. Accordingly, to provide flexibility to a user of a conventional electrosurgical device, the following disclosure describes various solutions for turning off the knife lockout.

While several devices have been made and used, it is believed that no one prior to the inventors has made or used the device described in the appended claims.

SUMMARY

In one embodiment, a surgical instrument is provided. The surgical instrument comprises a handle assembly. The handle assembly comprises a trigger operatively coupled to a firing plate; an energy button configured to deliver energy to at least one electrode; a lockout element operatively coupled to the energy button, the lockout element configured to prevent operation of the firing plate; and a lockout disabling mechanism configured to disable the lockout element, the lockout disabling mechanism operable between a first position and a second position, wherein when the lockout disabling mechanism is located in the first position, the lockout element is enabled and can be unlocked by the energy button, and wherein when the lockout disabling mechanism is in the second position, the lockout element is disabled.

In another embodiment, the lockout disabling mechanism of the surgical instrument comprises a button slidably movable between the first position and the second position; a slider operatively coupled to the button, wherein the slider is slidably movable between the first position and the second position by the button; and a lever arm having a first end and a second end, the first end coupled to the slider and the second end coupled to the lockout element. The lever arm disables the lockout element when the slider is slidably moved from the first position to the second position.

In various other embodiments, the lockout disabling mechanism of the surgical instrument comprises a lock arm operatively coupled to the lever arm and the lockout element. The slider of the surgical instrument comprises a ramped wall portion to engage the first end of the lever arm. The slider of the surgical instrument comprises a detent to provide tactile feedback when locking and unlocking the lockout disabling mechanism. The detent is configured to maintain the slider in the locked position.

In another embodiment, the lockout disabling mechanism of the surgical instrument comprises a button rotatably movable between the first position and the second position; a rotator operatively coupled to the button, wherein the rotator is rotatably movable between the first position and the second position by the button; and a lever arm having a first end and a second end, the first end coupled to the rotator and the second end coupled to the lockout element; wherein the lever arm disables the lockout element when the rotator is rotatably moved from the first position to the second position. The lockout disabling mechanism of the surgical instrument comprises a lock arm operatively coupled to the lever arm and the lockout element.

In one embodiment, a surgical instrument is provided. The surgical instrument comprises a handle assembly. The handle comprises a trigger operatively coupled to a trigger plate and a firing plate; an energy button configured to deliver energy to at least one electrode; a lockout element operatively coupled to the energy button, the lockout element configured to prevent operation of the firing plate; and a lockout disabling mechanism configured to disable the lockout element, the lockout disabling mechanism operable between a first position and a second position, wherein when the lockout disabling mechanism is located in the first position, the lockout element is enabled and can be unlocked by the energy button, and wherein when the lockout disabling mechanism is in the second position, the lockout element is disabled; a shaft assembly comprising a proximal end and a distal end, wherein the shaft assembly is coupled to the handle assembly at the proximal end; and an end effector coupled to the distal end of the shaft assembly. The end effector comprises a jaw assembly. The jaw assembly comprises a first jaw member; and a second jaw member, wherein rotation of the trigger plate transitions the jaw assembly between an open configuration and an approximated configuration by moving at least one of the first jaw member and the second jaw member relative to the other one of the first jaw member and the second jaw member; and a cutting member deployable in response to rotation of the firing plate.

In another embodiment, the lockout disabling mechanism of the surgical instrument comprises a button slidably movable between the first position and the second position; a slider operatively coupled to the button, wherein the slider is slidably movable between the first position and the second position by the button; and a lever arm having a first end and a second end, the first end coupled to the slider and the second end coupled to the lockout element; wherein the lever arm disables the lockout element when the slider is slidably moved from the first position to the second position.

In another embodiment, the lockout disabling mechanism of the surgical instrument comprises a lock arm operatively coupled to the lever arm and the lockout element. The slider of the surgical instrument comprises a ramped wall portion to engage the first end of the lever arm. The slider of the surgical instrument comprises a detent to provide tactile feedback when locking and unlocking the lockout disabling mechanism. The detent of the surgical instrument is configured to maintain the slider in the locked position.

In another embodiment, the lockout disabling mechanism surgical instrument comprises a button rotatably movable between the first position and the second position; a rotator operatively coupled to the button, wherein the rotator is rotatably movable between the first position and the second position by the button; and a lever arm having a first end and a second end, the first end coupled to the rotator and the second end coupled to the lockout element. The lever arm disables the lockout element when the rotator is rotatably moved from the first position to the second position. The lockout disabling mechanism of the surgical instrument comprises a lock arm operatively coupled to the lever arm and the lockout element.

In one embodiment, a surgical instrument is provided. The surgical instrument comprises an energy button; a lockout mechanism configured to prevent a cutting element from being fired unless the energy button is actuated; and a lockout disabling mechanism configured to disable the lockout mechanism, the lockout disabling mechanism is configured to operate between a first position and a second position, wherein when the lockout disabling mechanism is located in the first position, the lockout mechanism is enabled, and wherein when the lockout disabling mechanism is in the second position, the lockout mechanism is disabled.

In another embodiment, the lockout disabling mechanism of the surgical instrument comprises a button slidably movable between the first position and the second position; a slider operatively coupled to the button, wherein the slider is slidably movable between the first position and the second position by the button; and a lever arm having a first end and a second end, the first end coupled to the slider and the second end coupled to the lockout element. The lever arm disables the lockout element when the slider is slidably moved from the first position to the second position. The lockout disabling mechanism comprises a lock arm operatively coupled to the lever arm and the lockout element. The slider comprises a ramped wall portion to engage the first end of the lever arm. The slider comprises a detent to provide tactile feedback when locking and unlocking the lockout disabling mechanism. The detent is configured to maintain the slider in the locked position.

In another embodiment, the lockout disabling mechanism of the surgical instrument comprises a button rotatably movable between the first position and the second position; a rotator operatively coupled to the button, wherein the rotator is rotatably movable between the first position and the second position by the button; and a lever arm having a first end and a second end, the first end coupled to the rotator and the second end coupled to the lockout element. The lever arm disables the lockout element when the rotator is rotatably moved from the first position to the second position.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 6A is a detailed view of a knife lockout disabling mechanism showing a slider, a lever arm, and a button, according to one embodiment.

DESCRIPTION

Figure 1:
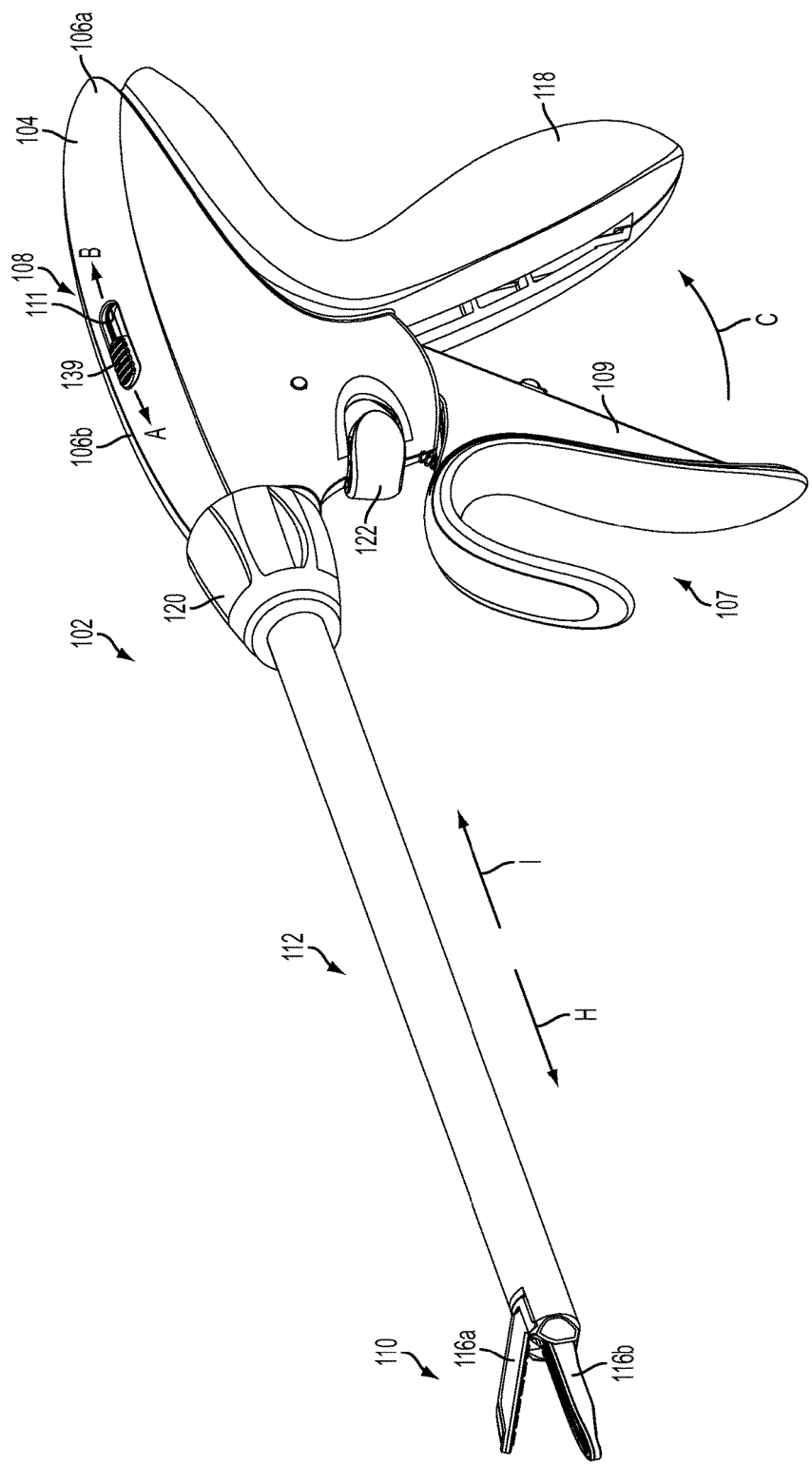
FIG. 1 illustrates a surgical instrument comprising a knife lockout disabling mechanism, according to one embodiment.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other.

Various suitable ways in which the teachings herein may be combined will be readily apparent to those of ordinary skill in the art in view of the teachings herein. Such modifications and variations are intended to be included within the scope of the claims.

Before explaining the various embodiments of the surgical devices having a knife lockout disabling mechanism in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

In various embodiments, the present disclosure provides an electrosurgical instrument comprising a knife lockout disabling mechanism configured to disable or override the knife lockout mechanism of the electrosurgical instrument. In one embodiment, the knife lockout disabling mechanism comprises a slider, a lever arm, and a button operatively coupled to the slider. The button can be engaged by the user to slidably move the slider back (proximally) and forth (distally) between several positions. In one embodiment, the slider is configured to slidably move back and forth between two positions. The lever arm is configured to pivot around a lock arm and to push in or activate the energy button when rotated. In one embodiment, the lever arm is connected to a ramped (or pivoting) slider that forces the lever arm to rotate and force the lock arm to rotate to unlock, disable, or override the knife lockout mechanism of the electrosurgical instrument. In one embodiment, the slider includes features to lock the lever arm in place once it is activated. A spring may be coupled to the energy button to force the lever arm and the slider back to their start positions once the energy button is deactivated. In other words, in one embodiment, the slider is configured to be in the lock-off (lock defeated) or lock-on (lock undefeated) position and the spring is configured to force the slider back to its start position in the transition area.

In another embodiment, the knife lockout disabling mechanism of the electrosurgical instrument comprises a rotator, a lever arm, and a button operatively coupled to the rotator configured to disable, override, or otherwise turn off the knife lockout mechanism of the electrosurgical instrument. The button can be engaged by the user to rotate the rotator between various positions. In one embodiment, the rotator can be rotated between two positions. The rotator acts on the lever arm to engage a surface of the lockout mechanism and thereby defeat the lockout mechanism of the electrosurgical instrument.

The above knife lockout disabling mechanisms, as discussed in more detail below, provide several advantages over conventional electrosurgical devices with knife lockout mechanisms that cannot be disabled. For example, the lockout disabling mechanisms according to the present disclosure are configured to fit in a form factor of current electrosurgical instruments with only a change to one of the housing shrouds. The lockout disabling mechanism generally moves between two states (off or on). Thus, the button portion of the slider or rotator can move slidably or rotatably between the two positions or states but not in any intermediate positions between the two states. In one embodiment, the button can be retrofitted into some existing electrosurgical instruments and locks into place without requiring any additional or new components to lock it in position. The button can be configured to employ a spring that is already provided for the energy button, as described herein. Also, either the slider or rotator is operatively coupled to the energy button such that when the knife lockout disabling mechanism is activated, it moves the energy button inward to provide a visual and tactile clue that the knife lockout feature is turned off.

Turning now to the figures, FIG. 1 illustrates a surgical instrument 102 comprising a trigger assembly 107 and a lockout disabling mechanism 108. In this view, a first jaw member 116*a* of an end effector 110 is fully open and the knife lockout disabling mechanism 108 is located in the off position. The knife lockout disabling mechanism 108 is configured to clamp and fire an end effector 110 coupled to the surgical instrument 102. The surgical instrument 102 comprises a handle assembly 104, a shaft assembly 112, and the end effector 110. The shaft assembly 112 comprises a proximal end and a distal end. The proximal end of the shaft assembly 112 is coupled to the distal end of the handle assembly 104. The end effector 110 is coupled to the distal end of the shaft assembly 112. The handle assembly 104 comprises a pistol grip 118. The handle assembly 104 comprises a left handle housing shroud 106*a* and a right handle housing shroud 106*b*. The trigger assembly 107 comprises a trigger 109 actuatable towards the pistol grip 118. The knife lockout disabling mechanism 108 comprises a button 139, or knob, that is actuatable for adjusting or controlling the position of the knife lockout disabling mechanism 108 between first and second positions A and B (A=Distal and B=Proximal relative to the clinician) within a slot 111 formed in the left handle housing shroud 106*a*. A rotatable shaft knob 120 is configured to rotate the shaft assembly 112 with respect to the handle assembly 104. The handle assembly 104 further comprises an energy button 122 configured to provide electrosurgical energy to one or more electrodes in the end effector 110.

Figure 48:
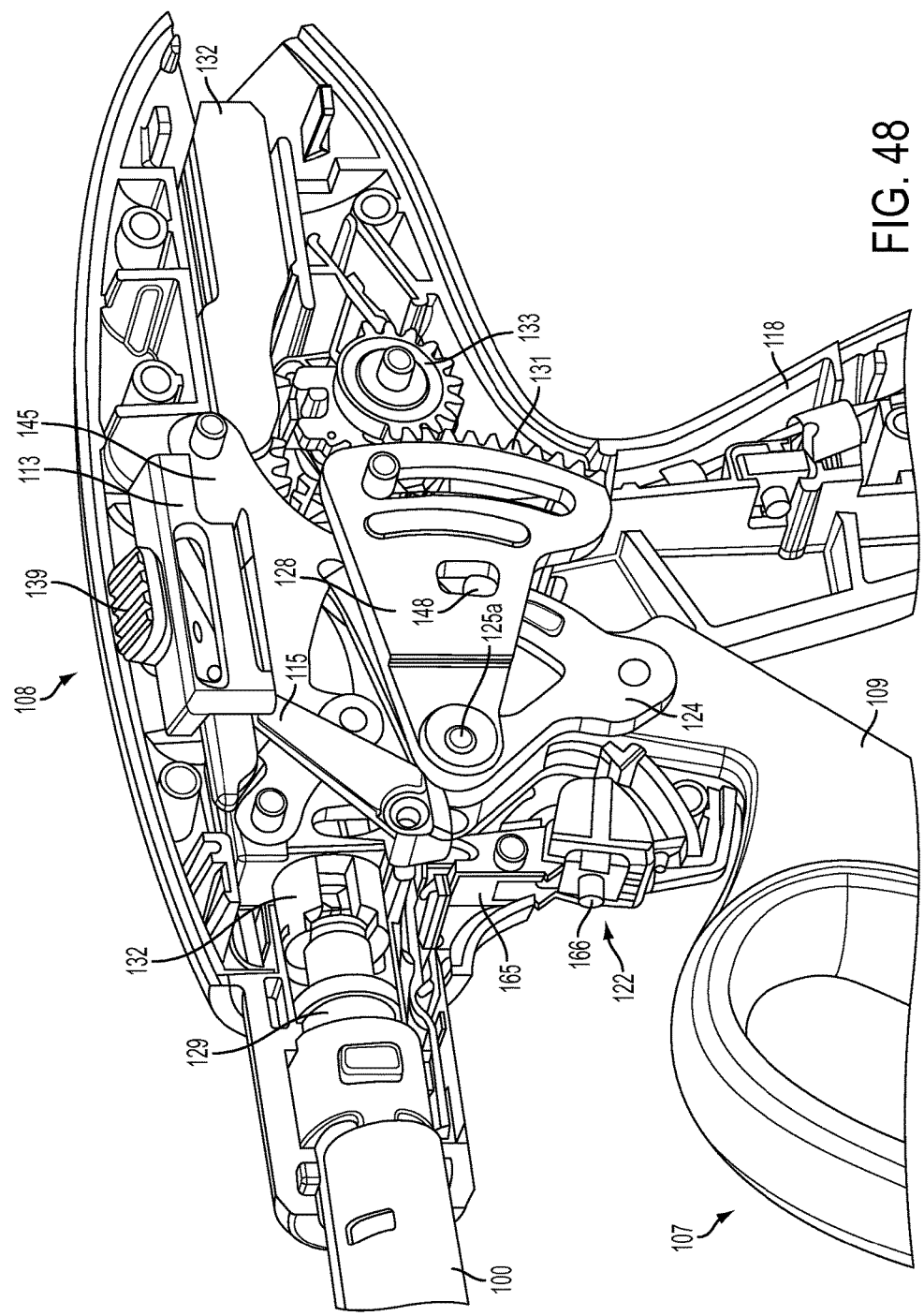
FIG. 48 is a side view of an end effector portion of the surgical instrument shown in FIGS. 1 and 2 showing an energy button located underneath the energy button housing to illustrate that the lock release mechanism also is the energy delivery element, according to one embodiment.

The knife lockout mechanism forces the user to first clamp (close the jaws 110), energize the electrodes, and then cut the tissue (fire the knife). The knife unlock feature contains the energy button 122 so that the energy button 122 has to be depressed before the knife can be released or that the single trigger can move the rack 136 forward. The single trigger 109 closes the jaws in the first ~13 degrees of stroke. The single trigger 109 fires the knife in the last ~29 degrees of stroke. The lockout is the stop in between the first stroke and the second stroke. As shown in FIG. 48, an energy button 166 is located underneath the energy button 122 housing to illustrate that the lock release mechanism also is the energy delivery element.

The shaft assembly 112 comprises a closure/jaw actuator, a firing/cutting member actuator, and an outer sheath. In some embodiments, the outer sheath comprises the closure actuator. The outer sheath comprises one or more contact electrodes on a distal end configured to interface with the end effector 110. The one or more contact electrodes are operatively coupled to the energy button 122 and an energy source (not shown).

The energy source may be suitable for therapeutic tissue treatment, tissue cauterization/sealing, as well as sub-therapeutic treatment and measurement. The energy button 122 controls the delivery of energy to the electrodes. As used throughout this disclosure, a button refers to a switch mechanism for controlling some aspect of a machine or a process. The buttons may be made out of a hard material such as usually plastic or metal. The surface may be formed or shaped to accommodate the human finger or hand, so as to be easily depressed or pushed. Buttons can be most often biased switches, even though many un-biased buttons (due to their physical nature) require a spring to return to their un-pushed state. Terms for the "pushing" of the button, may include press, depress, mash, and punch.

In some embodiments, an end effector 110 is coupled to the distal end of the shaft assembly 112. The end effector 110 comprises a first jaw member 116a and a second jaw member 116b. The first jaw member 116a is pivotally coupled to the second jaw member 116b. The first jaw member 116a is pivotally moveable with respect to the second jaw member 116b to grasp tissue therebetween. In some embodiments, the second jaw member 116b is fixed. In other embodiments, the first jaw member 116a and the second jaw member 116b are pivotally movable. The end effector 110 comprises at least one electrode. The electrode is configured to deliver energy. Energy delivered by the electrode may comprise, for example, radiofrequency (RF) energy, sub-therapeutic RF energy, ultrasonic energy, and/or other suitable forms of energy. In some embodiments, a cutting member (not shown) is receivable within a longitudinal slot defined by the first jaw member 116a and/or the second jaw member 116b. The cutting member is configured to cut tissue grasped between the first jaw member 116a and the second jaw member 116b. In some embodiments, the cutting member comprises an electrode for delivering energy, such as, for example, RF and/or ultrasonic energy.

In certain instances, as described above, the surgical instrument 102 may include an automatic energy lockout mechanism. The energy lockout mechanism can be associated with a closure mechanism of the surgical instrument 102. In certain instances, the energy lockout mechanism can be configured to permit energy delivery to the end effector 10 when the energy delivery button 122 is actuated if the jaw members 116a and 116b are in an open configuration. In certain instances, the energy lockout mechanism may be configured to deny energy delivery to the end effector 110 when the energy delivery button 122 is actuated if the jaw members 116a and 116b are in a closed configuration. In certain instances, the energy lockout mechanism automatically transitions from permitting the energy delivery to denying the energy delivery when the jaw members 116a and 116b are transitioned from the closed configuration to the open configuration, for example. In certain instances, the energy lockout mechanism automatically transitions from denying the energy delivery to permitting the energy delivery when the jaw members 116a and 116b are transitioned from the open configuration to the closed configuration, for example.

Figure 2:
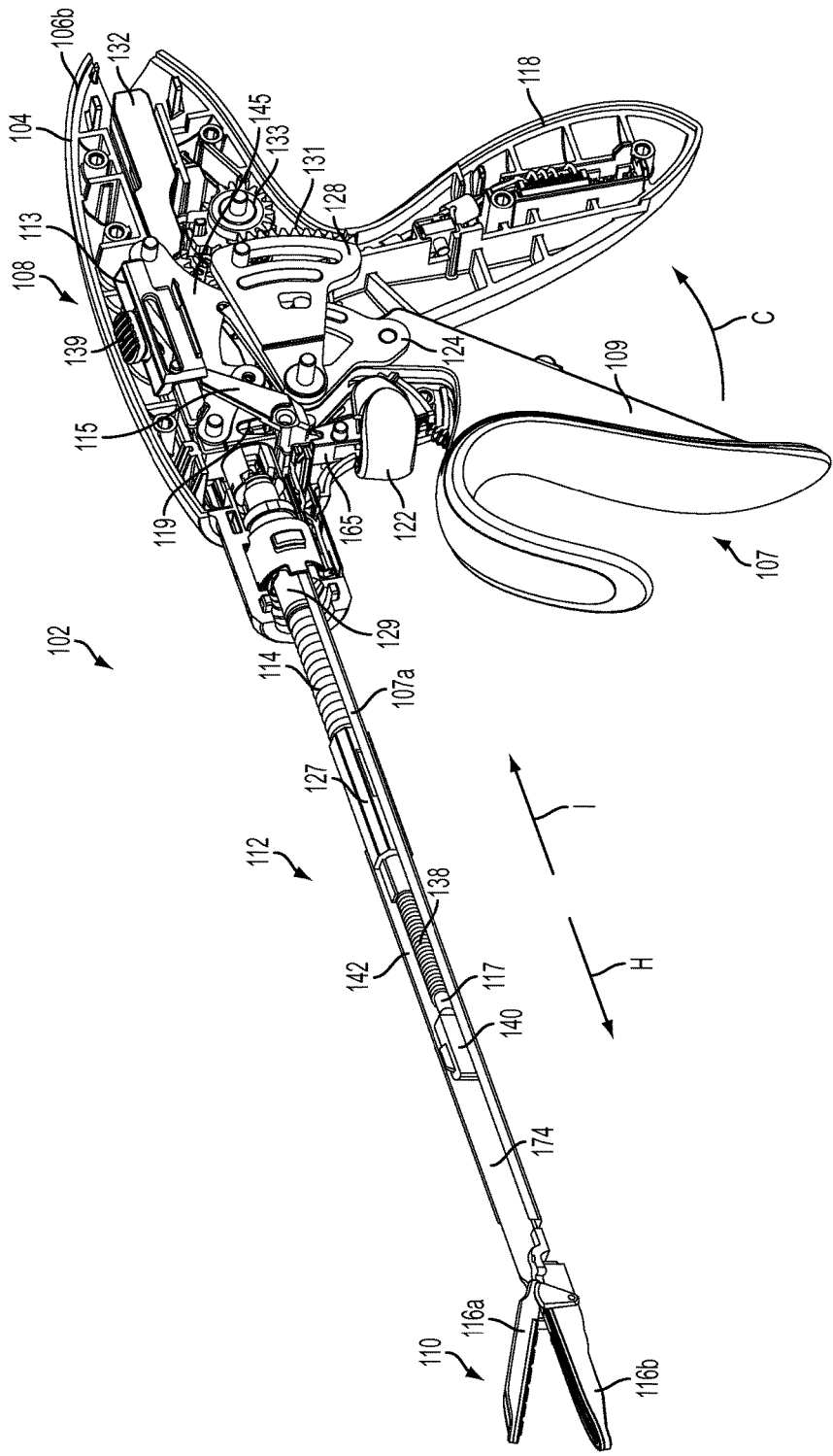
FIG. 2 is a perspective view of a handle assembly of the surgical instrument illustrated in FIG. 1 with the left handle housing shroud and several sheaths in the shaft assembly removed, according to one embodiment.

FIG. 2 is a perspective view of a handle assembly 104 of a surgical instrument 102 illustrated in FIG. 1, according to one embodiment, with the right housing shroud 106a and the outer and inner sheaths of the shaft assembly 112 removed to show some of the internal mechanisms. The left handle housing shroud 106b of the handle assembly 104 comprises the knife lockout disabling mechanism 108. The button 139 is located in the first "off" position A (A=distal relative to the clinician) within the slot 111 formed in the right handle housing shroud 106a. In the illustrated embodiment, position B (B=proximal relative to the clinician) corresponds to the second "on" position of the knife lockout disabling mechanism 108, where the knife lockout mechanism remains disabled until the button is switched back to position A. Accordingly, position A corresponds to the enabled state of the knife lockout mechanism and position B corresponds to the disabled state of the knife lockout mechanism. Stated differently, position A corresponds to the "off" state of the knife lockout disabling mechanism 108 and position B corresponds to the "on" state of the knife lockout disabling mechanism 108. When the knife lockout mechanism is in the disabled state, the energy button 122 may appear to be depressed to provide a visual indication to the clinician that the knife lockout mechanism has been disabled but without energizing the electrodes in the end effector 110 (FIG. 1). When the knife lockout mechanism is disabled, the knife may be fired at will without the need to apply electrosurgical energy to one or more electrodes in the end effector 110.

The trigger assembly 107 comprises the necessary components for closing the jaw members 116a, 116b and firing the cutting member or knife bands 174. The trigger assembly 107 comprises a trigger plate 124 and firing plate 128 operatively coupled to the trigger 109. Squeezing the trigger 109 in direction C towards the pistol grip 118 rotates the trigger plate 124 which operates the toggle clamp 145 to advance a yoke 132 and a closure actuator 129 distally to close the jaw members 116a, 116b of the end effector. Initial rotation of the trigger plate 124 also slightly rotates the firing plate 128. The firing plate 128 comprises a sector gear with a plurality of teeth 131 that engage and rotate a first pinion gear 133, which engages a second pinion gear 134 to advance a rack 136 (neither is shown in this view). A lock arm 157 (shown in FIGS. 22-24, 28, 32, 35, 38, 41, 44, for example) is operatively coupled to a lever arm 115, an unlock arm 119, and a lockout element 165. When the instrument 102 is in normal lockout mode, the lock arm 157 engages a notch 158 (shown in FIGS. 23-25, 38, 41, 44, and 45, for example) in the rack 136 to lock the rack 136 and prevent the rack 136 from moving distally (firing) no matter how hard the trigger 109 is squeezed.

The single trigger 109 closes the jaws in the first ~13 degrees of stroke. The trigger plate 124 is configured to interface with the toggle clamp 145 during rotation of the trigger 109 from an initial position to a first rotation, which is ~13 degrees of stroke, for example. The trigger plate 124 is operably coupled to the firing plate 128. In certain instances, the firing plate 128 may include a first slot 128a and a second slot 128b. The first slot 128a receives a drive pin 148 fixedly coupled to the trigger plate 124. The pin 148 slidably moves within the first slot 128a. Rotation of the trigger plate 124, while the pin 148 is slid ably received within the first slot 128a, drives rotation of the firing plate 128. The teeth 131 of the sector gear engage and rotate the first pinion 133, which in turn drives the second pinion 134, which drives the rack 136 distally to fire the cutting element, or knife, but only when the knife lockout is unlocked, released, or disabled.

The single trigger 109 fires the knife in the last ~29 degrees of stroke. Rotation of the trigger plate 124 beyond a predetermined rotation such as, for example, the first rotation, causes rotation of the firing plate 128. Rotation of the firing plate 128 deploys a cutting member within the end effector 110. For example, in the illustrated embodiment, the firing plate 128 comprises a sector gear operably coupled to a rack 136 through the first and second pinions 133, 134. The firing plate 128 comprises a plurality of teeth 131 configured to interface with the first pinion 133. Rotation of the firing plate 128 rotates the first and second pinions 133, 134, to drive the rack 136 distally. Distal movement of the rack 136 drives the cutting member actuator distally, causing deployment of the cutting member (e.g., knife) within the end effector 110.

The lockout is the stop in between the first stroke and the second stroke. Turning back now to the description of the lockout disabling mechanism 108, when the slider 113 button 139 portion is in located in position A, the lock arm 157 can be released by pressing or actuating the energy button 122 to rotate the lockout element 165, which rotates the unlock arm 119 to release the lock arm 157. Once the lock arm 157 is released, the rack 136 is enabled to advance distally and fire the knife by squeezing the trigger 109 in direction C further towards the pistol grip 118. As the trigger 109 is squeezed, the firing plate 128 rotates and drives the first pinion gear 133, which drives the second pinion gear 134 to drive the rack 136.

When the slider 113 button 139 is located in position B, the slider 113 rotates the lever arm 115, which rotates the unlock arm 119 to release the lock arm 157. While the button 139 is in position B, the rack 136 can be fired without the need to press energy button 122 to rotate the lockout element 165. A detent may be provided to hold the button in either position A or B. These and other features are described in more detail hereinbelow.

The shaft assembly 112 comprises a closure/jaw actuator and a firing/cutting member actuator. The closure/jaw actuator comprises a yoke 132 and toggle clamp 145 assembly operatively coupled to a closure actuator 129 which acts on a closure spring 114 coupled to a spring-to-bar interface element 127 and a closure bar 142. In one instance the closure bar 142 is operatively coupled to the jaw members 116a, 116b via at least one linkage. The firing/cutting member actuator comprises a rack 136 operatively coupled to a firing bar 117, which is slidably received within the closure actuator 129 and the closure spring 114. The firing bar 117 is coupled to a knife pusher block 140 and a flexible I-beam knife band 174 comprising multiple flexible bands fastened together and a cutting element at the distal end. Advancing the rack 136 in the distal direction advances the cutting element band 174 distally through a channel or slot formed in the jaw members 116a, 116b.

Figure 3:
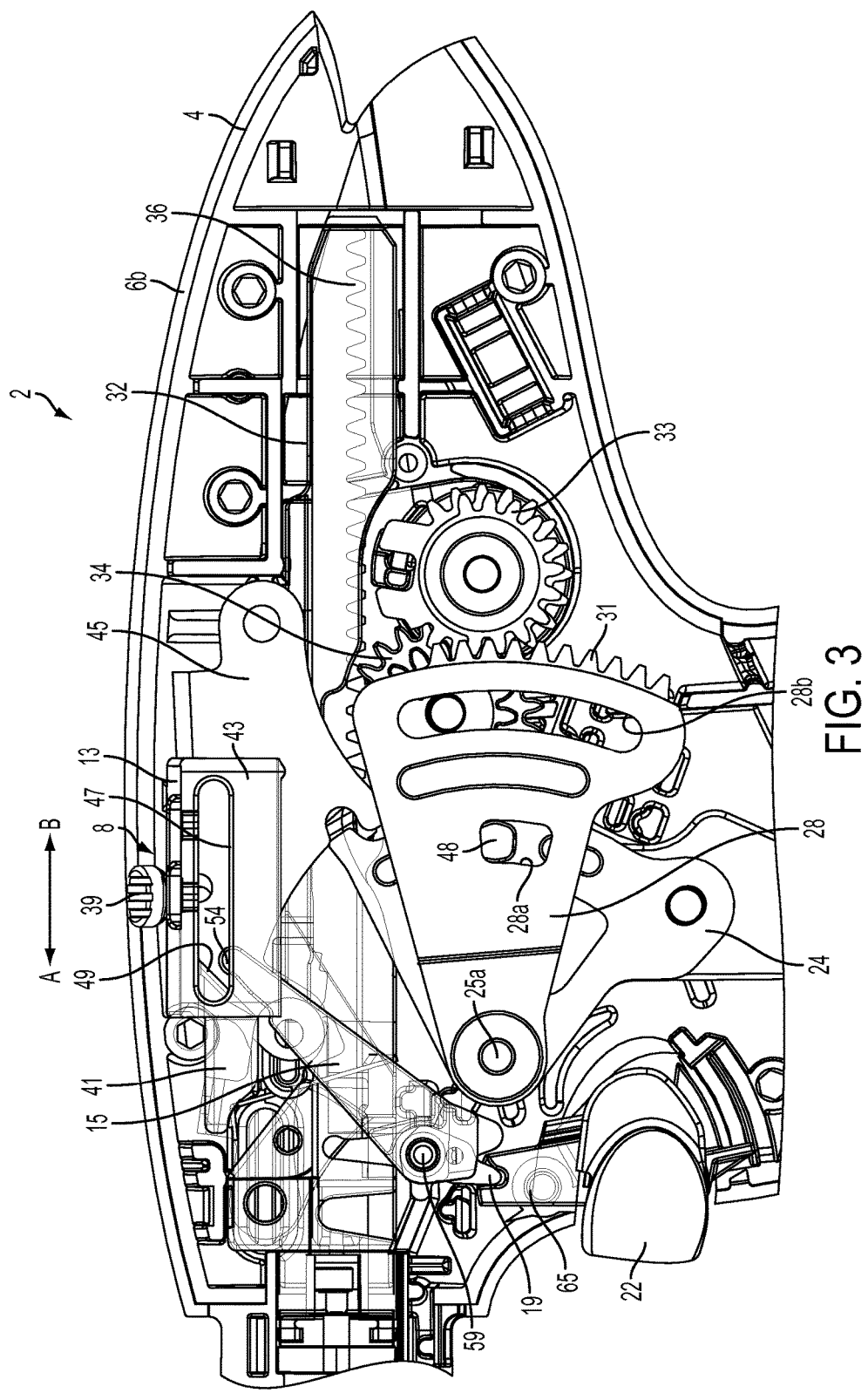
FIG. 3 is a side elevation view of a handle assembly of a surgical instrument, similar to the surgical instrument shown in FIGS. 1 and 2, with the left handle housing shroud removed, according to one embodiment.
Figure 4:
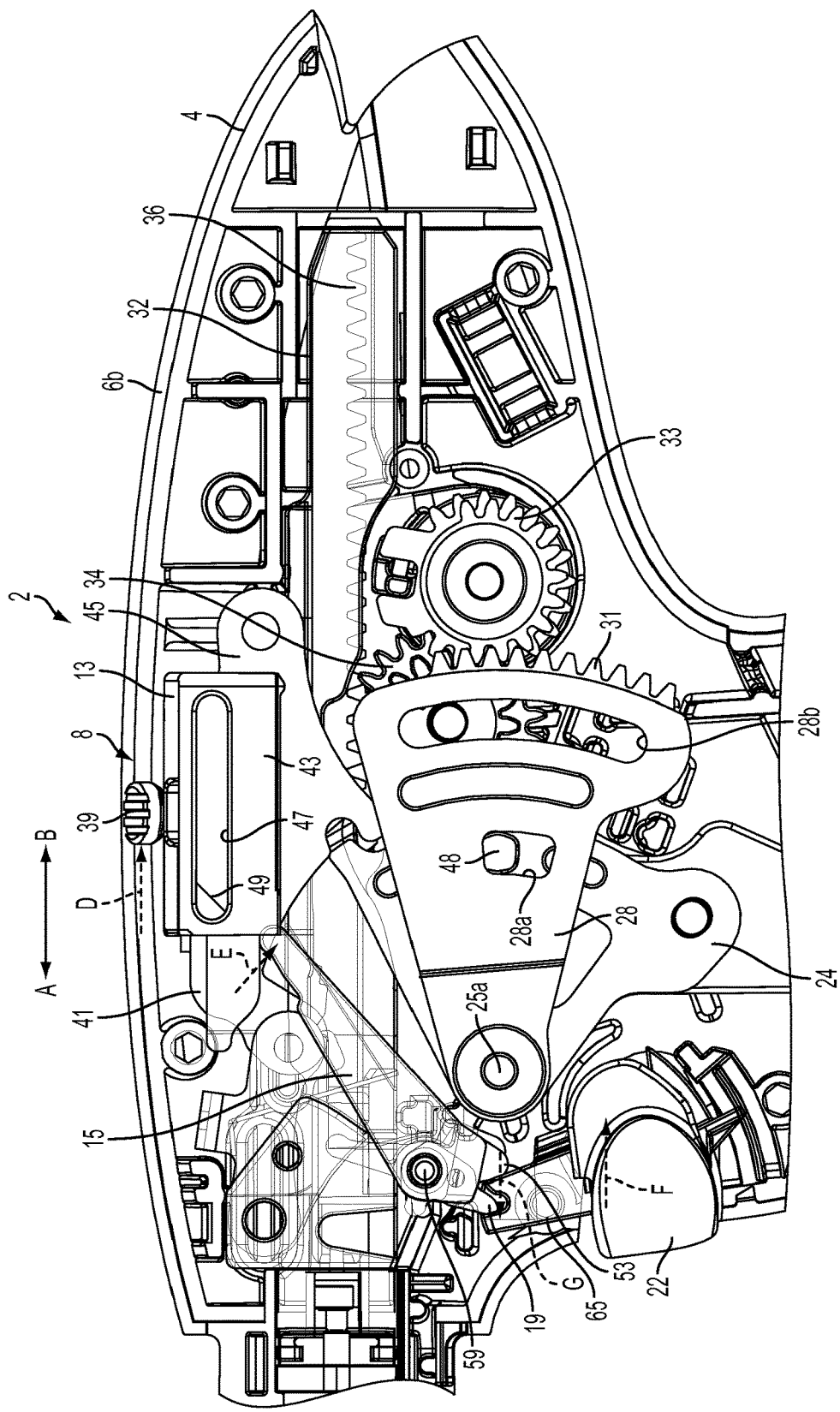
FIG. 4 is a side elevation view of the handle assembly of the surgical instrument shown in FIG. 3, according to one embodiment.

FIG. 3 is a side elevation view of a handle assembly 4 of a surgical instrument 2 similar to the surgical instrument 102 shown in FIGS. 1 and 2, with the left handle housing shroud removed to expose various mechanisms located within the handle assembly 4 and the knife lockout mechanism enabled. The handle assembly 4 comprises a plurality of components for actuating the surgical instrument 2, such as, for example, mechanism for affecting the closure of the jaw members of the end effector, deploying a cutting member (e.g., knife) within the end effector, and/or delivering energy to one or more electrodes coupled to the end effector. The knife lockout disabling mechanism 8 is configured to disable the knife lockout mechanism of the end effector. The knife lockout disabling mechanism 8 comprises a slider 13, a lever arm 15, and a button 39 operatively coupled to the slider 13. An unlock arm 19 is actuated by the lever arm 15 as the slider 13 is slidably translated from the first position A to the second position B as indicated in FIG. 4. While the slider 13 translates in a proximal direction B, a ramped or angled wall 49 formed within a body 43 portion of the slider 13 engages or contacts one end 51 of the lever arm 15 causing the lever arm 15 to rotate in a first direction E about a pivot point 59. The rotating lever arm 15 pushes the unlock arm 19 causing the unlock arm 19 to rotate in the same first direction. One end of the unlock arm 19 rotates the knife lockout element 65 in a second, opposite, direction and the other end of the unlock arm 19 rotates the lock arm 57 (not shown in this view, but shown in FIGS. 8 and 9) to unlock or disable the knife lockout function.

FIG. 4 is a side elevation view of the handle assembly 4 of the surgical instrument 2 shown in FIG. 3, with the left handle housing shroud removed to expose various mechanisms located within the handle assembly 4 and the knife lockout mechanism disabled, according to one embodiment. As shown in FIG. 4, the slider 13 has been slidably translated to the proximal position as indicated by arrow D. The lever arm 15 and the unlock arm 19 have been rotated in a the direction indicated by arrow G by the other end 53 of the lever arm 15 and the knife lockout element 65 has been rotated in a second, opposite, direction. The unlock arm 19 acts on the lock arm 57 to disable the knife lockout function. The energy button 22 is operatively coupled to the unlock arm 19. Thus, the energy button 22 will be in a depressed state as indicated by arrow F when the knife lockout element 65 has been disabled.

Figure 5:
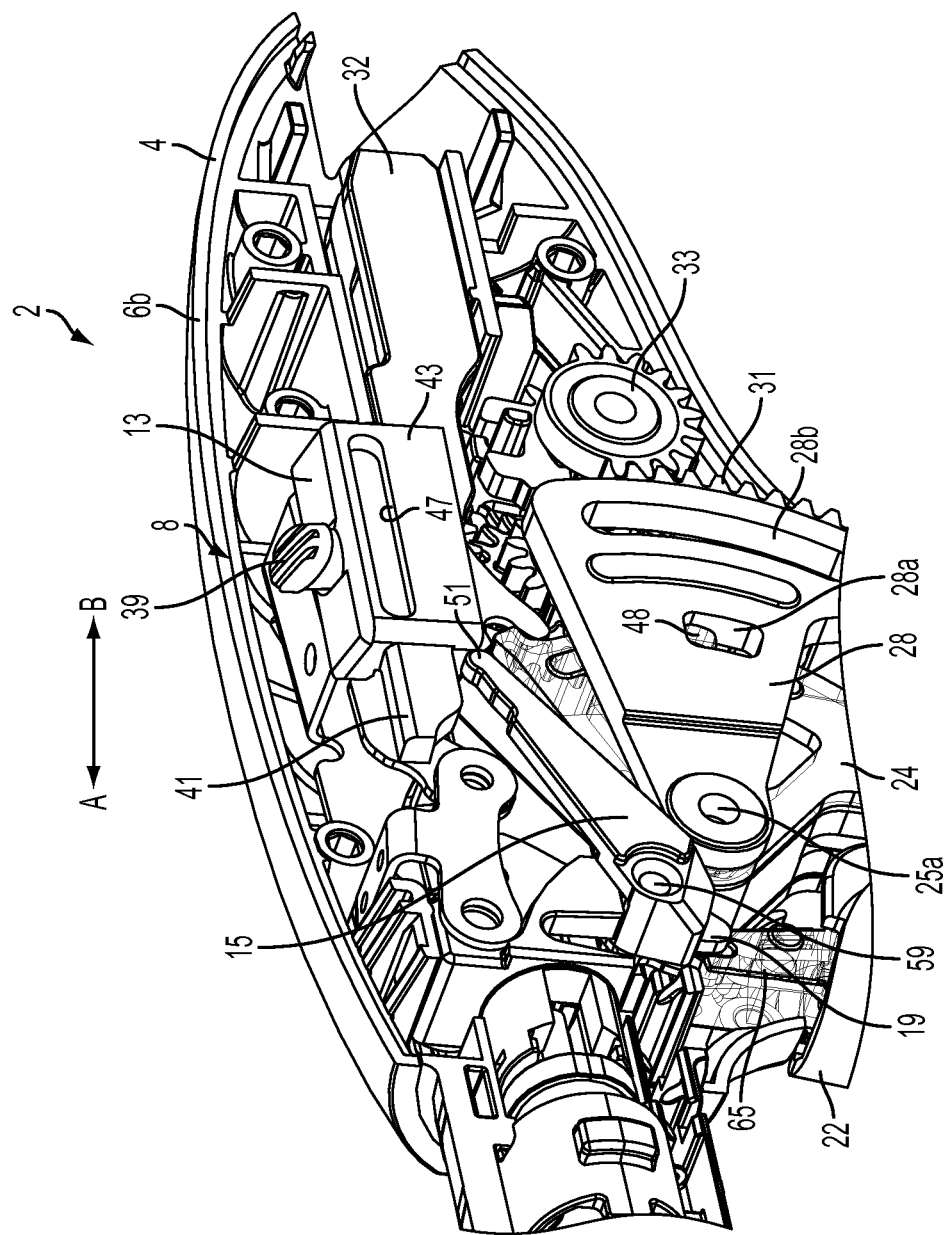
FIG. 5 is a perspective view of the handle assembly of the surgical instrument shown in FIG. 4, according to one embodiment.

FIG. 5 is a perspective view of the handle assembly 4 of the surgical instrument 2 shown in FIG. 4, with the left handle housing shroud removed to expose various mechanisms located within the handle assembly 4 and the knife lockout element 65 disabled, according to one embodiment. In various embodiments, the electrosurgical instrument 2 comprising a knife lockout disabling mechanism 8 configured to disable or override the knife lockout element 65 of the electrosurgical instrument 2. As shown win FIG. 5, the slider 13 has been slidably translated proximally in direction B to disable the knife lockout element 65 as described in connection with FIG. 4. The button 39 can be engaged by the clinician to slidably move the slider 13 back (proximally) and forth (distally) between several positions. In one embodiment, the slider 13 is configured to slidably move back and forth between the first and second positions A and B. The lever arm 15 is configured to pivot about the unlock arm 19 and to push in the energy button 22 when rotated. In one embodiment, the lever arm 15 is coupled to a ramped (or pivoting) slider 13 that forces the lever arm 15 to rotate in a first direction and force the unlock arm 19 to rotate in a second, opposite, direction. The unlock arm 19 rotates the lock arm 57 to unlock, disable, or override the knife lockout mechanism of the electrosurgical instrument 2. In one embodiment, the slider 13 includes features to lock the lever arm 15 in place once it is activated. A spring may be coupled to the energy button 22 to force the lever arm 15 and the slider 13 back to their start positions A or B once the energy button 22 is deactivated. In other words, in one embodiment, the slider 13 may be configured to be in the lock-OFF (lock defeated, disabled, etc.) or lock-ON (lock undefeated, enabled, etc.) position and the spring is configured to force the slider 13 back to its start position in the transition area. A longitudinal projection 41 extends distally from the body 43 of the slider 13.

Turning now to FIGS. 3-5, the knife lockout disabling mechanism 8 is coupled to one or more mechanisms for closing the jaw members of the end effector and deploying a cutting member (e.g., knife) therein. In one embodiment, when the trigger 9 is squeezed in direction C towards the pistol grip 18, the trigger 9 rotates the trigger plate 24 about a rotation point defined by a rotation pin 25a. Rotation of the trigger plate 24 to a first position causes a toggle clamp 45 to advance a yoke 32 and a closure actuator configured to transition the jaw members from an open position to a closed position. For example, in the illustrated embodiment, the toggle clamp 45 is operatively coupled to a yoke 32. The toggle clamp 45 is movably coupled to the trigger plate 24. Rotation of the trigger plate 24 also drives the yoke 32 distally. Distal movement of the yoke 32 compresses a closure spring 114, causing distal movement of the closure actuator. As previously discussed in connection with FIGS. 1 and 2, distal movement of the closure actuator compresses a closure spring. The closure spring is coupled to a closure bar via the spring-to-bar interface element. Accordingly, distal movement of the closure actuator causes the closure bar to pivotally move the first jaw member from an open position to a closed position with respect to the second jaw member, for example.

Rotation of the trigger plate 24 beyond a predetermined rotation such as, for example, the first rotation position, causes partial rotation of the firing plate 28. Rotation of the firing plate 28 deploys a cutting member within the end effector 10. For example, in the illustrated embodiment, the firing plate 28 comprises a sector gear operably coupled to a rack 36 through first and second pinions 33 and 34. The sector gear of the firing plate 28 comprises a plurality of teeth 31 configured to interface with the first pinion 33. The first pinion 33 drives the second pinion 34. Thus, rotation of the firing plate 28 rotates the pinions 33 and 34, driving the rack 36 distally. Distal movement of the rack 36 drives the cutting member actuator distally, causing deployment of the cutting member (e.g., knife) within the end effector 10. The rack 36, however, comprises at least one notch 58 configured to engage the lock arm 57. When the lock arm 57 engages the notch 58 in the rack 36, the rack 36 is prevented from firing distally. This is referred to as the lockout state. When the button 39 in position A, the energy button 22 must be depressed inwardly towards to pistol grip 18 to unlock the lock arm 57 and release the rack 36. A spring is provided behind the energy button 22 to balance out this force. When the button 39 in position B, the lockout mechanism is disabled by the lever arm 15 and the unlock arm 19 releasing the lock arm 57.

The trigger plate 24 is configured to interface with the toggle clamp 45 during rotation of the trigger 9 from an initial position to a first rotation position, for example. The trigger plate 24 is operably coupled to the firing plate 28. In certain instances, the firing plate 28 may include a first slot 28a and a second slot 28b. The first slot 28a receives a drive pin 48 coupled to the trigger plate 24. The drive pin 48 is slidably driven by the trigger plate 24 in the first slot 28a and drives the firing plate 28.

Rotation of the firing plate 28 by the drive pin 48 in the first slot 28a rotates the sector gear teeth 31, which engage and rotate the first pinion 33. The first pinion 33 rotates the second pinion 34. The second pinion 34 drives the rack 36 distally to fire the cutting element (e.g., knife), but only when the lock arm 57 is released or disabled from the notch 58 in the rack 32 either by locating the button 39 in position B or pressing the energy button 22 to release the lockout element 65.

FIG. 6 illustrates a detailed view of the knife lockout disabling mechanism 8 showing the slider 13, one end of the lever arm 15, and the button 39, according to one embodiment. The slider 13 comprises a body 43 defining a longitudinal slot 47 enabling the slider 13 to slidably translate in either direction A or B. In FIG. 6, the slider 13 is shown in the proximal position B, wherein the lock arm 57 is disabled allowing the rack 32 to move distally to drive the firing bar. A projection 41 extends longitudinally from the body 43 of the slider 13. At the distal end of the projection 41, a detent 21 feature provides tactile feedback to the clinician when locking and unlocking the knife lockout mechanism. The detent 21 feature also keeps the slider 13 in the unlocked position like a detent. An angled wall 49 (ramp) portion of the body 43 engages one end 51 of the lever arm 15.

Figure 6B:
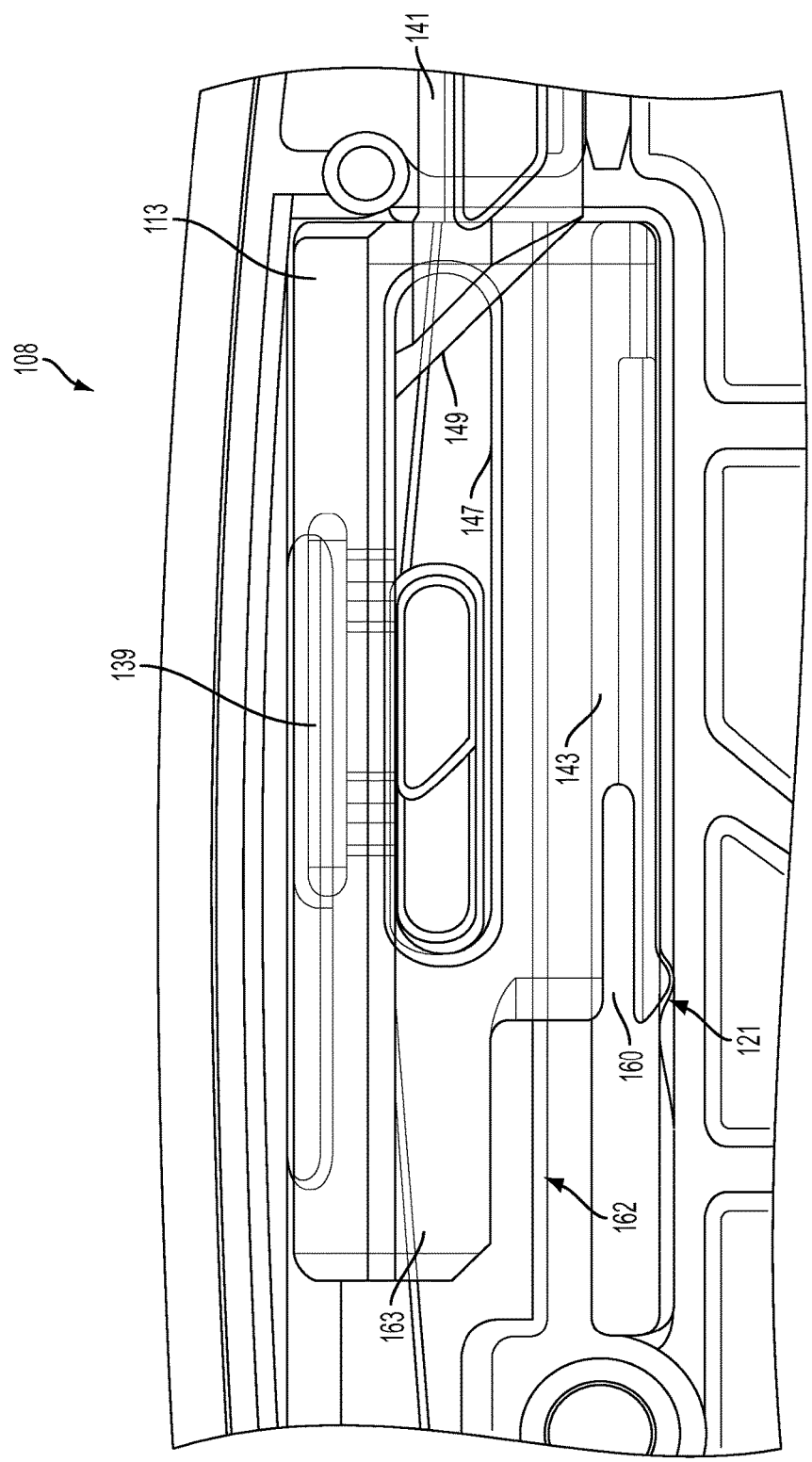
FIG. 6B is a detailed view of a knife lockout disabling mechanism showing a slider, a lever arm, and a button, according to one embodiment.
Figure 7:
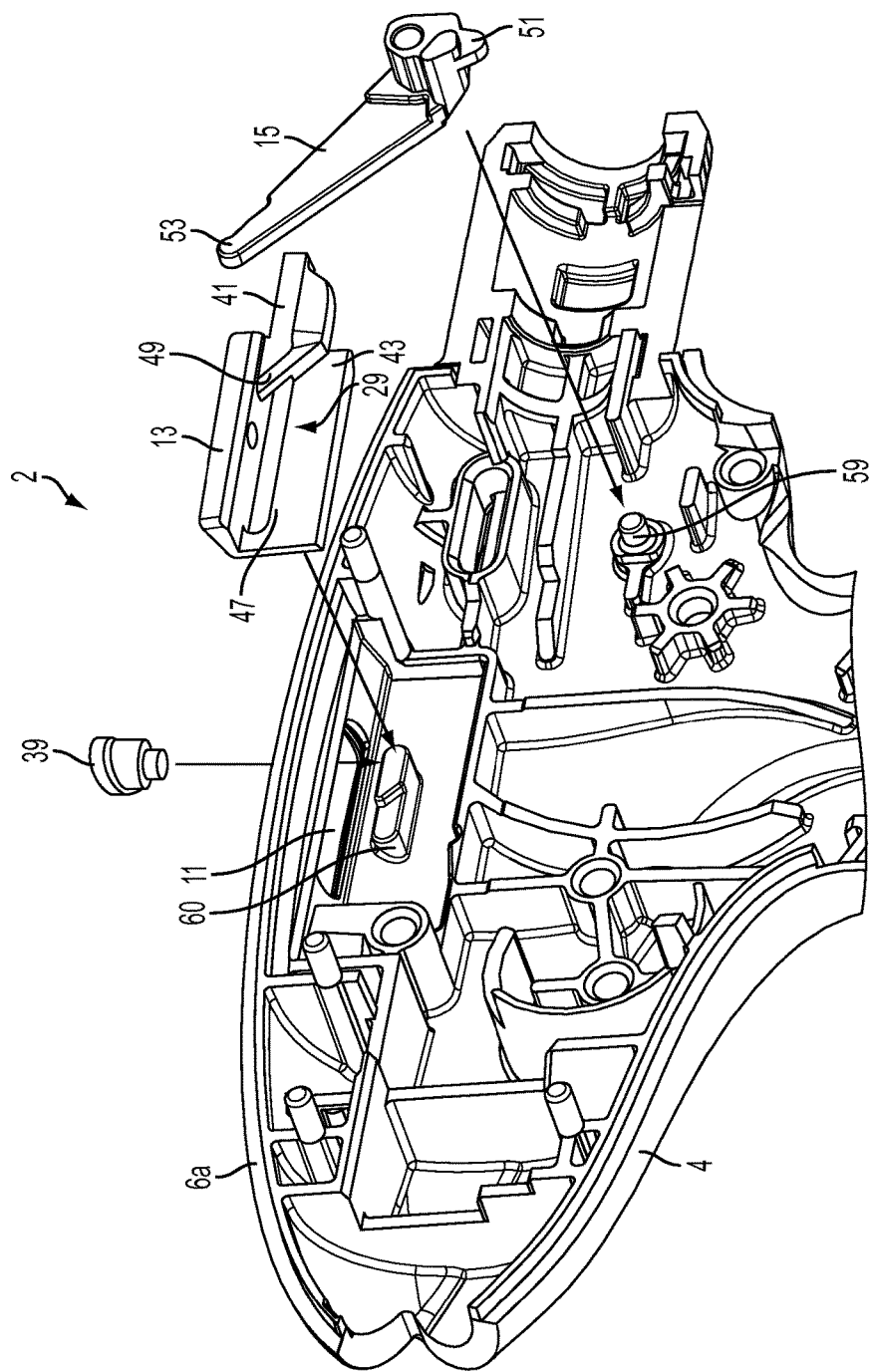
FIG. 7 is an exploded view of a handle assembly with the right handle housing shroud and various mechanisms located within the handle assembly removed, according to one embodiment.

FIG. 7 is an exploded view of the handle assembly 4 with the right handle housing shroud and various mechanisms located within the handle assembly 4 removed to more clearly show the components of the knife lockout disabling mechanism 8, according to one embodiment. As shown in FIG. 6, the slider 13 comprises a longitudinal slot 47 that is slidably movable over a longitudinal projection 60 formed on the left handle housing shroud 6a. The slot 11 provides an aperture for the button 39, operatively coupled to the slider 13, to slidably move between first and second positions (A and B). One end 53 of the lever arm 15 is pivotally mounted to a pivot point 27 formed on the left handle housing shroud 6a. Another end 51 of the lever arm 15 is received in a space 29 defined by the slider 13 body 43 and engages the ramp 49 when the slider is in position A.

Figure 8:
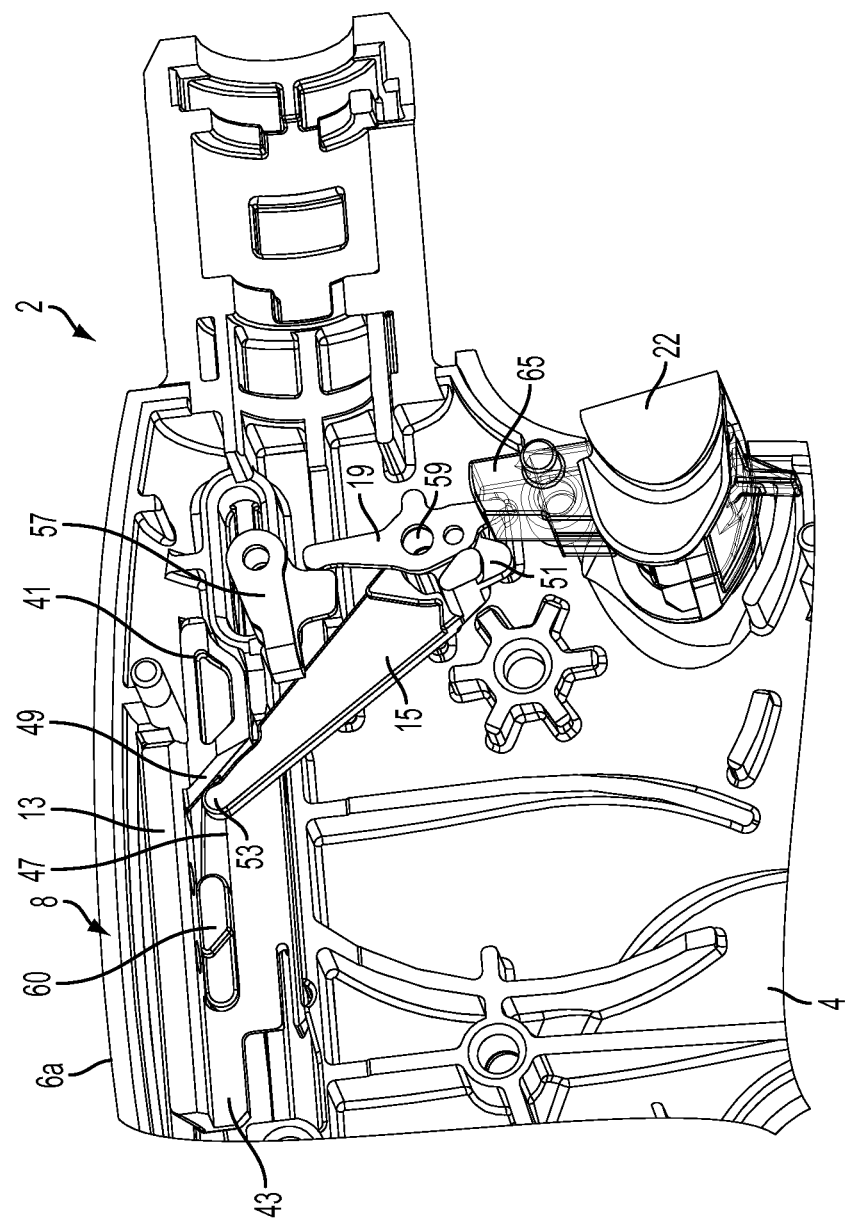
FIG. 8 is a perspective view of a handle assembly with the right handle housing shroud and various mechanisms located within the handle assembly removed, according to one embodiment.
Figure 9:
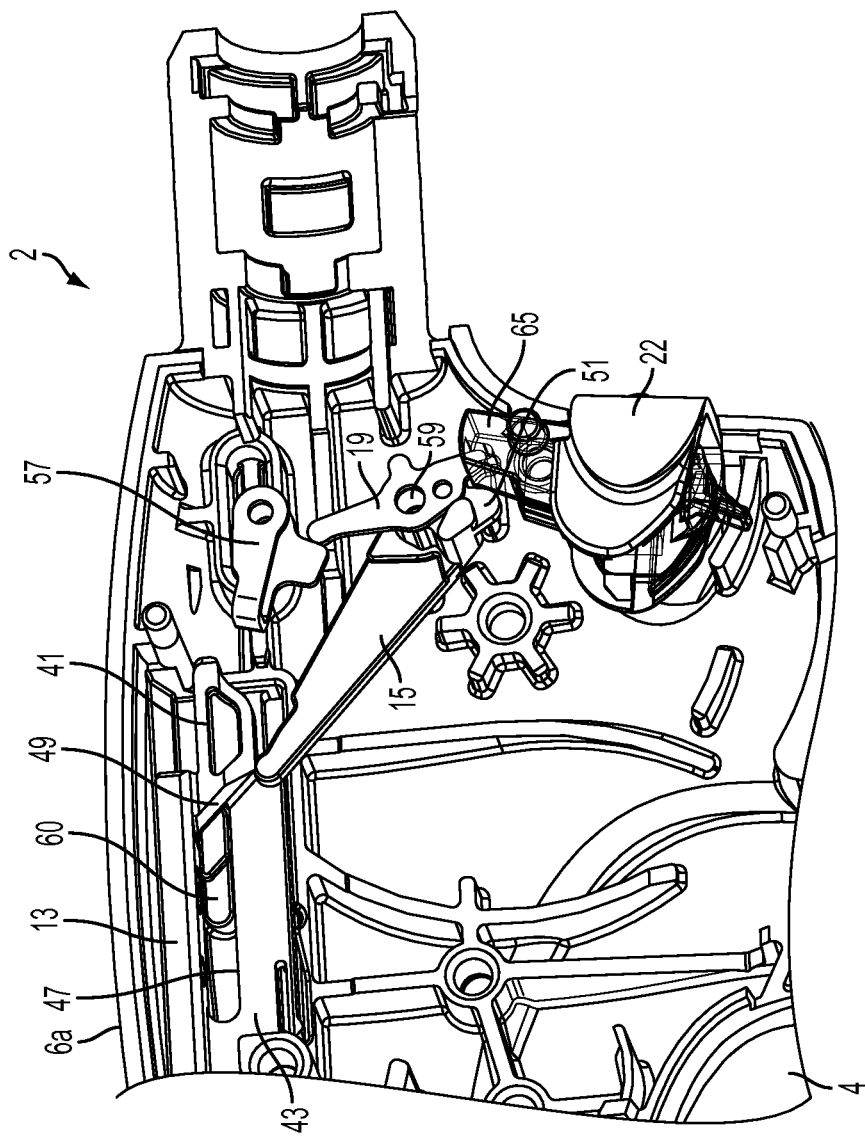
FIG. 9 is a perspective view of a handle assembly with the right handle housing shroud and various mechanisms located within the handle assembly removed, according to one embodiment.

FIGS. 8 and 9 are perspective views of the handle assembly 4 with the right handle housing shroud and various mechanisms located within the handle assembly 4 removed to more clearly show the components of the knife lockout disabling mechanism 8, according to one embodiment. As shown in FIG. 8, the knife lockout disabling mechanism 8 is in the locked state. The slider 13 is located in position A and one end of the lever arm 15 is abutting the ramp 49 wall formed in the slider 13 body 43. The ramp 49 engages one end 53 of the lever arm 15 to pivotally rotate the lever arm 15 as the slider 13 moves from position A, shown in FIG. 8, to position B, shown in FIG. 9. The lever arm 15 is configured to pivot the unlock arm 19 such that one end of the unlock arm 19 pushes in the energy button 22 when rotated as shown in FIG. 9 and the other end of the unlock arm 19 release the lock arm 57 to disable the knife lockout mechanism. As shown in FIG. 8, the lockout element 65 is shown in the locked position such that the lock arm 57 engages the notch 58 formed in the rack 32 to prevent the knife from firing. As shown in FIG. 9, when the unlock arm 19 is rotated in the second, opposite, direction, the lock arm 57 unlocks the knife lockout function to enable firing of the knife without actuating the energy button 22. Nevertheless, the energy button 22 is slightly pushed in to provide an indication that the lockout function has been disabled.

Figure 10:
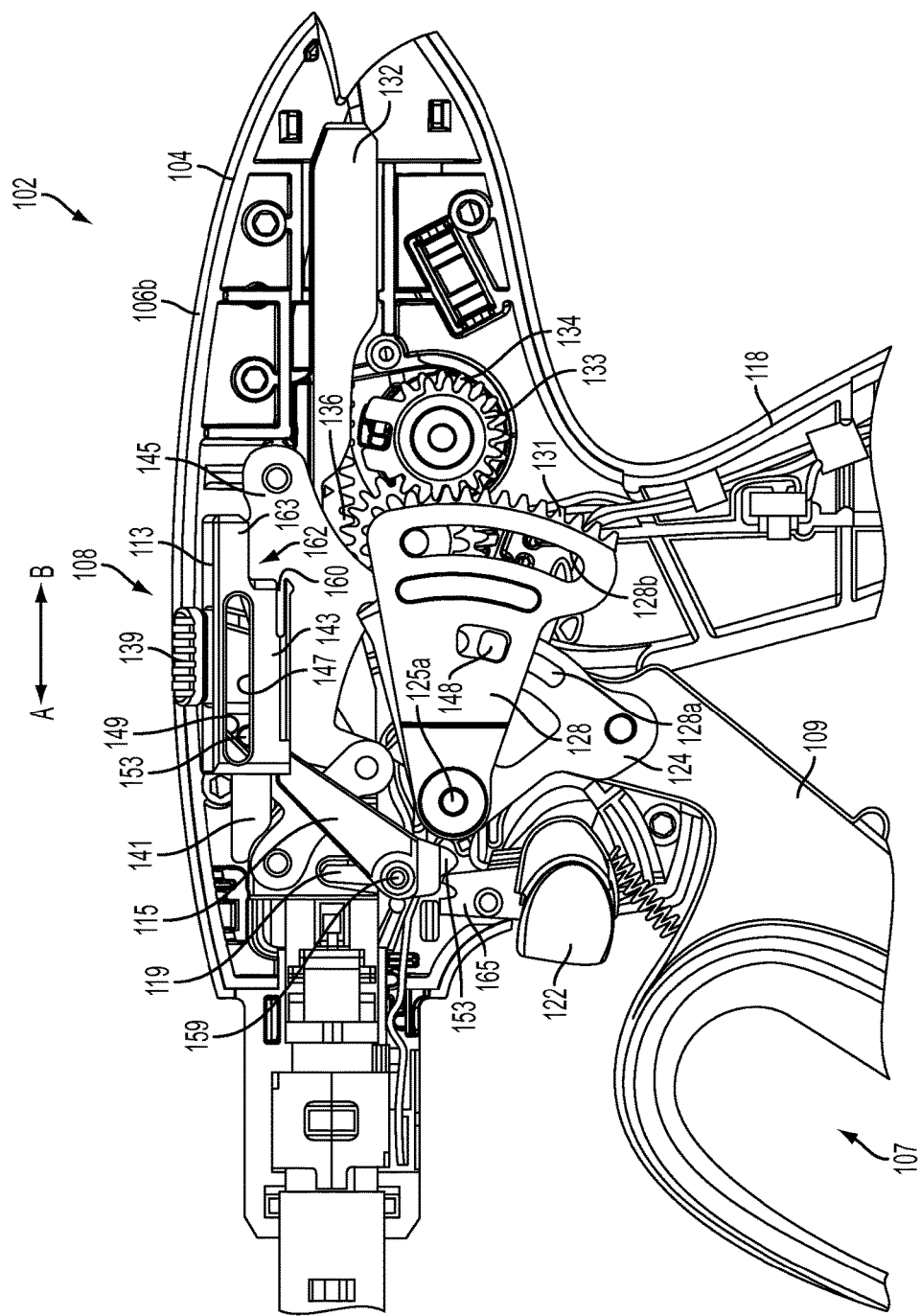
FIG. 10 is a side elevation view of a handle assembly of a surgical instrument, with the left handle housing shroud removed, according to one embodiment.

FIGS. 10-15 illustrate a knife lockout disabling mechanism according to another embodiment. FIG. 10 is a side elevation view of the handle assembly 104 of a surgical instrument 102, with the left handle housing shroud 106a removed to expose various mechanisms located within the handle assembly 104 and the knife lockout disabling mechanism 108 in the "off" position, according to one embodiment. The knife lockout disabling mechanism 108 comprises a slider 113, a button 139, and a lever arm 115. The slider 113 comprises a body 143 defining a longitudinal slot 147 wherein the slider 113 slidably translates in directions A and B by sliding the button 139. The slider 113 further comprises longitudinally extending projections 141, 163, where the second longitudinal projection 163 and the body 143 define a cutout portion 162. A ramped or angled wall 149 engages the end 153 of the lever arm 115. Thus, when the slider 113 moves from position A to position B, the ramp 149 engages the one end 153 of the lever arm 115 causing it to rotate in a first direction. The rotation of the lever arm 115 in the first direction causes one end of the unlock arm 119 to rotate in the same first direction to push on the knife lockout element 165 and the other end of the unlock arm 119 disengages the lock arm 157 (shown in FIGS. 22-24, 28, 32, 35, 38, 41, 44, for example) from the notch 158 (shown in FIGS. 23-25, 38, 41, 44, and 45, for example) in the rack 132. When the lock arm 57 is rotated out of the notch 58 it unlocks or disables the knife lockout function, thus enabling the cutting element to be fired by the rack 132.

As shown in FIG. 10, a slider 113 portion of the knife lockout disabling mechanism 108 has been slidably translated to a distal position by sliding the button 139 in the distal direction A. A lever arm 115 is configured to rotate in a first direction as indicated by arrow E when the slider 113 is slidably translated in the proximal direction B as indicated by arrow B. A unlock arm 119 is configured to rotate in the same first direction when one end 153 of the lever arm 115 pushes on the unlock arm 119 as the slider 113 is slidably translated in the proximal direction B. One end of the unlock arm 119 pushes on the knife lockout element 165 to cause it to rotate in an opposite second direction and the other end of the unlock arm 119 unlocks the lock arm 57 to disable the knife lockout function. The energy button 122 is operatively coupled to the unlock arm 119 and is shown in an undepressed state to show that the knife lockout mechanism is enabled.

Figure 11:
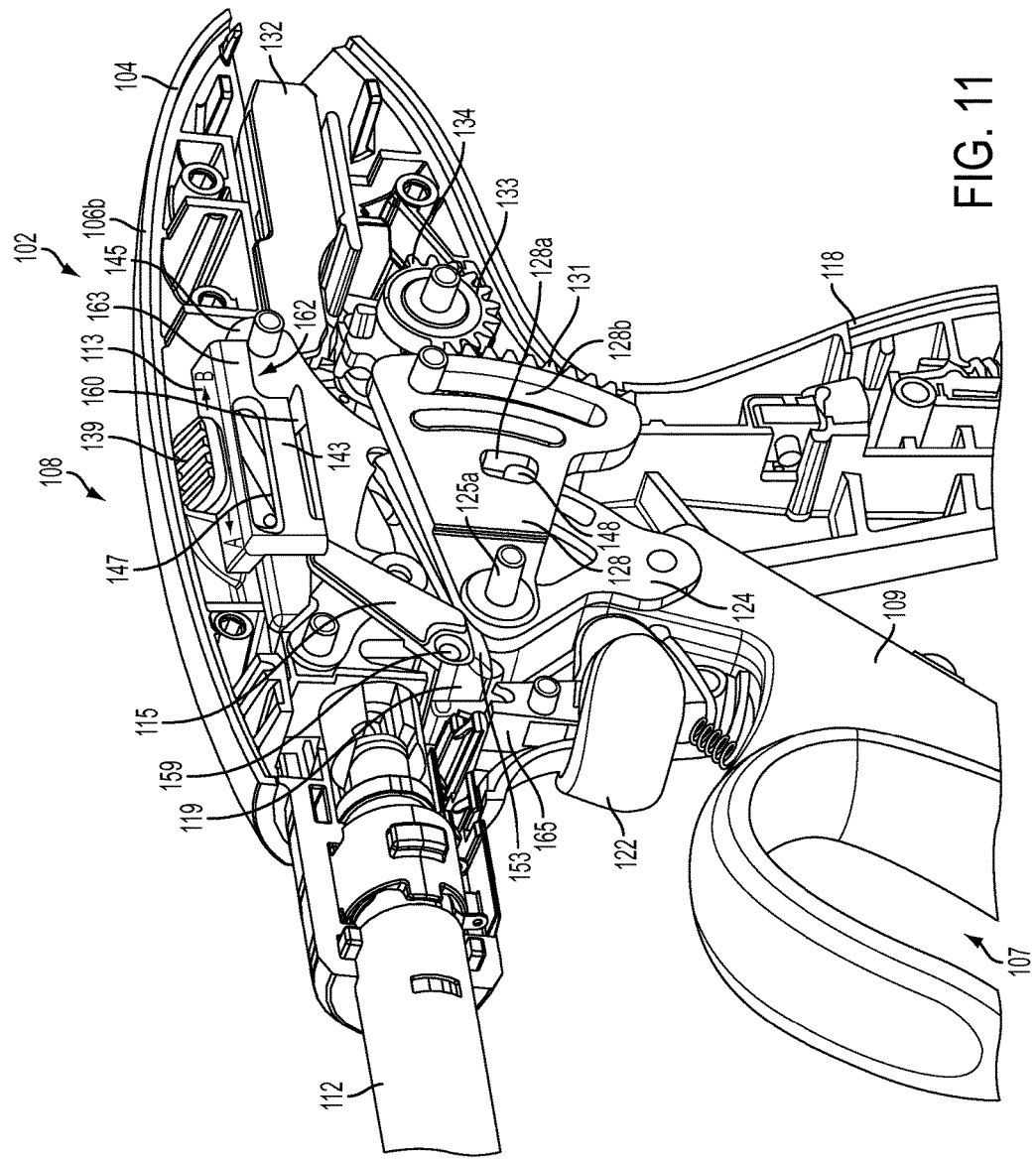
FIG. 11 is a perspective view of the handle assembly portion of the surgical instrument shown in FIG. 10, with the left handle housing shroud removed, according to one embodiment.

FIG. 11 is a perspective view of the handle assembly 104 of the surgical instrument 102 shown in FIG. 10, with the left handle housing shroud 106a removed to expose various mechanisms located within the handle assembly 104 and the knife lockout mechanism disabled, according to one embodiment. In various embodiments, the electrosurgical instrument 102 comprising a knife lockout disabling mechanism 108 configured to disable or override the knife lockout mechanism of the electrosurgical instrument 102. As shown win FIG. 11, the slider 113 is still in the distal position A such that the knife lockout mechanism is enabled as described in connection with FIG. 10. The button 139 can be engaged by the clinician to slidably move the slider 113 back (proximally) and forth (distally) between several positions. In one embodiment, the slider 113 is configured to slidably move back and forth between the first and second positions A and B. The lever arm 115 is configured to pivot about the unlock arm 119 and to push in the energy button 122 when rotated. In one embodiment, the lever arm 115 is connected to a ramped (or pivoting) slider 113 that forces the lever arm 115 to rotate in a first direction and force the unlock arm 119 to rotate in a second, opposite, direction to unlock, disable, or override the knife lockout mechanism of the electrosurgical instrument 102. In one embodiment, the slider 113 includes features to lock the lever arm 115 in place once it is activated. A spring may be coupled to the energy button 122 to force the lever arm 115 and the slider 113 back to their start positions A or B once the energy button 122 is deactivated. In other words, in one embodiment, the slider 113 is configured to be in the lock-off (lock defeated) or lock-on (lock undefeated) position and the spring is configured to force the slider 113 back to its start position in the transition area. A longitudinal projection 141 extends distally from the body 143 of the slider 113.

Figure 12:
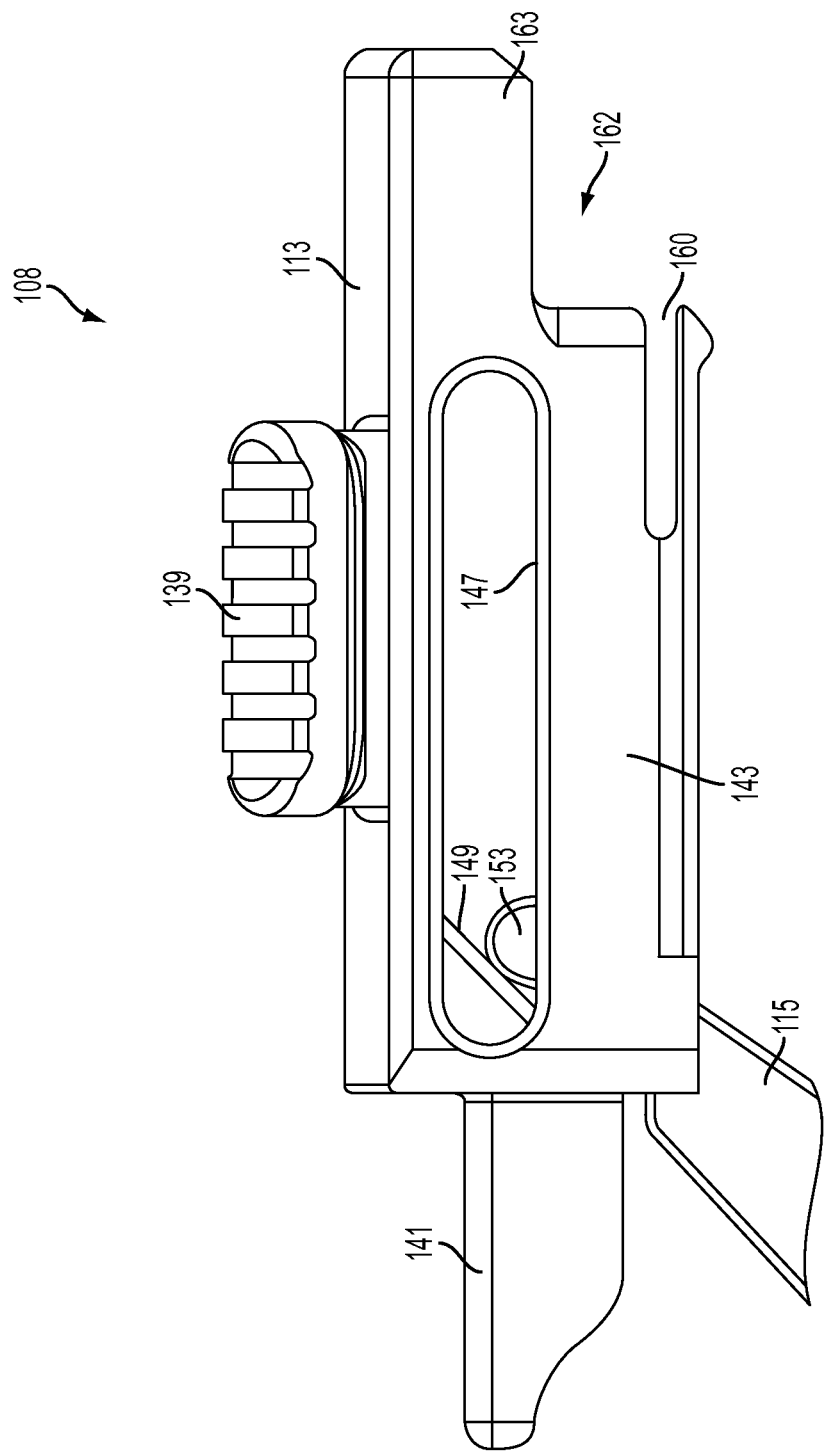
FIG. 12 is a detailed view of a knife lockout disabling mechanism showing a slider, a lever arm, and a button, according to one embodiment.

FIGS. 12 and 6B are detailed views of the knife lockout disabling mechanism 108 showing the slider 113, one end of the lever arm 115, and the button 139, according to one embodiment. The slider 113 comprises a body 143 defining a first longitudinal slot 147 that enables the slider 113 to slidably translate proximally and distally. A projection 141 extends longitudinally from the body 143 of the slider 113. At the distal end of the projection 141, a detent 121 feature provides tactile feedback to the clinician when locking and unlocking the knife lockout mechanism. The detent 121 feature also keeps the slider 113 in the unlocked position. An angled or ramped wall 149 portion of the body 143 engages one end 151 of the lever arm 115. A second longitudinal slot 160 and a cutout portion 162 defined by the second longitudinal projection 163 and the body 143 are provided on a proximal end of the slider 113.

As shown more particularly in FIG. 6B, the detent 121 is provided to the lock defeat OFF position so that the slider 113 will stay in place even when the lockout button 139 is pushed in. The detent 121 prevents the slider 113 from moving backwards when the energy button 122 is pressed to defeat the lockout. When the energy button 122 is depressed to defeat the lockout mechanism, the lockout defeat lever arm 115 moves with the energy button 122 and could cause the slider 113 to move freely with gravity or if the device is jolted. The detent 121 prevents the slider 113 from moving freely with gravity or if the device is jolted when the energy button 122 is depressed to defeat the lockout mechanism.

Figure 13:
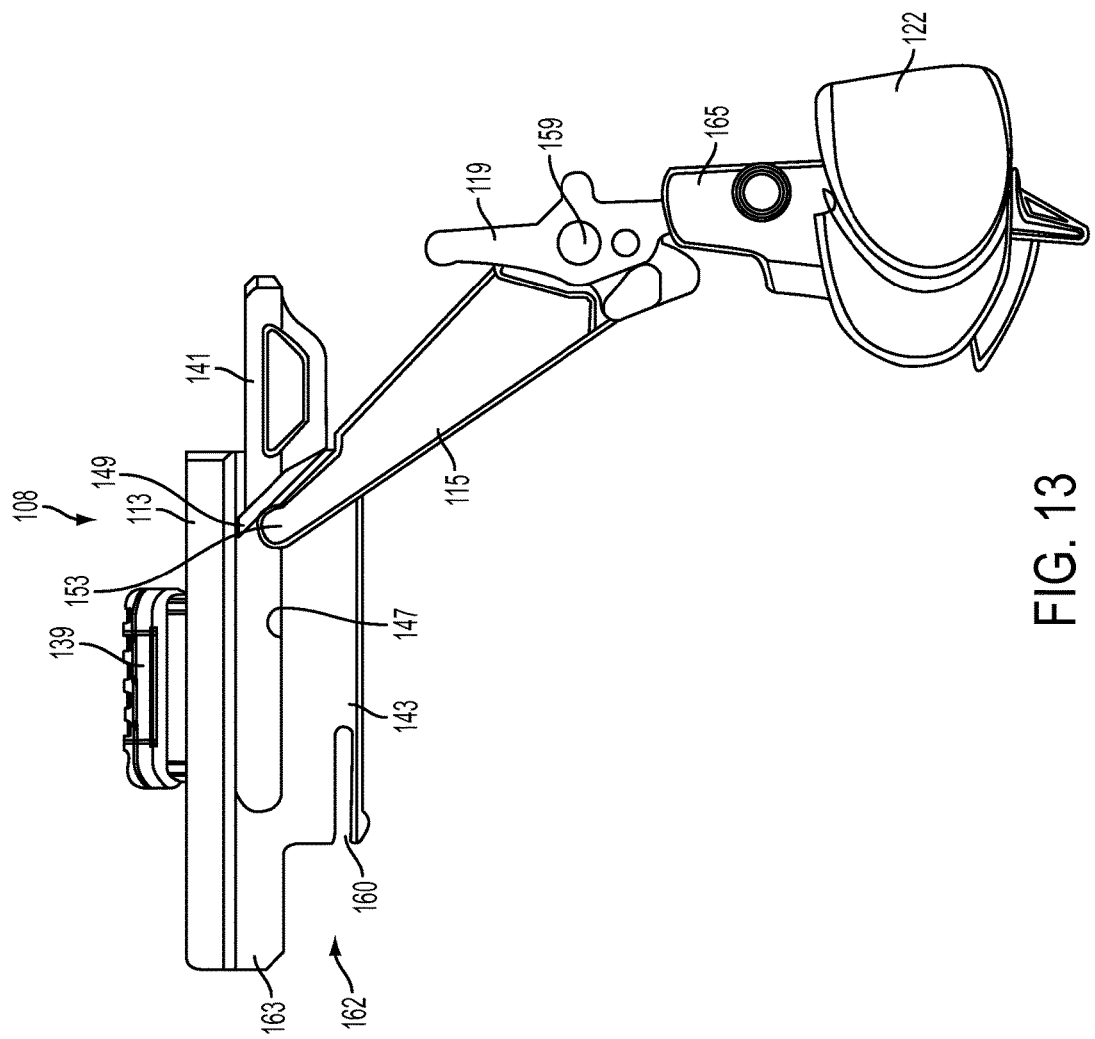
FIG. 13 is a side elevational view of a knife lockout disabling mechanism, according to one embodiment.

FIG. 13 is a side elevation view of the knife lockout disabling mechanism 108, according to one embodiment. The slider 113 is shown in the distal position corresponding to an enabled knife lockout mechanism. The button 139 is employed to slidably translate the slider 113 proximally and distally along the first longitudinal slot 147. The one end 151 of the lever arm 115 is shown resting on the ramped wall 149 portion of the slider 113 body 143. As shown, the lever arm 115 includes a notched portion 164 and defines a detent 121 to provide tactile feedback to the user regarding the state of the knife lockout mechanism. The lever arm 115 is rotatably coupled the unlock arm 119, which is rotatably coupled to the energy button 122.

Figure 14:
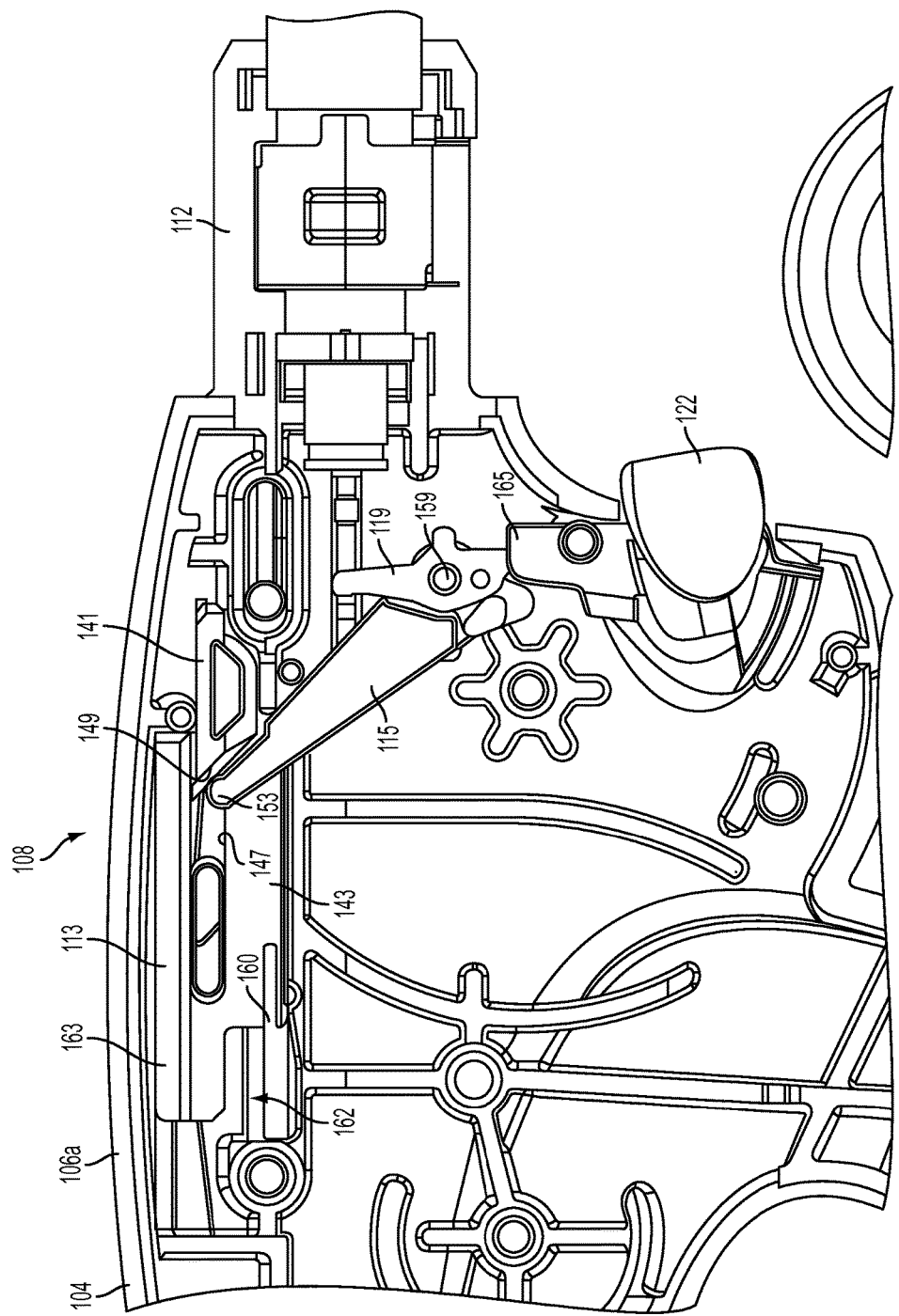
FIG. 14 is a side elevational view of the surgical instrument shown in FIG. 3 with the right handle housing shroud removed, according to one embodiment.
Figure 15:
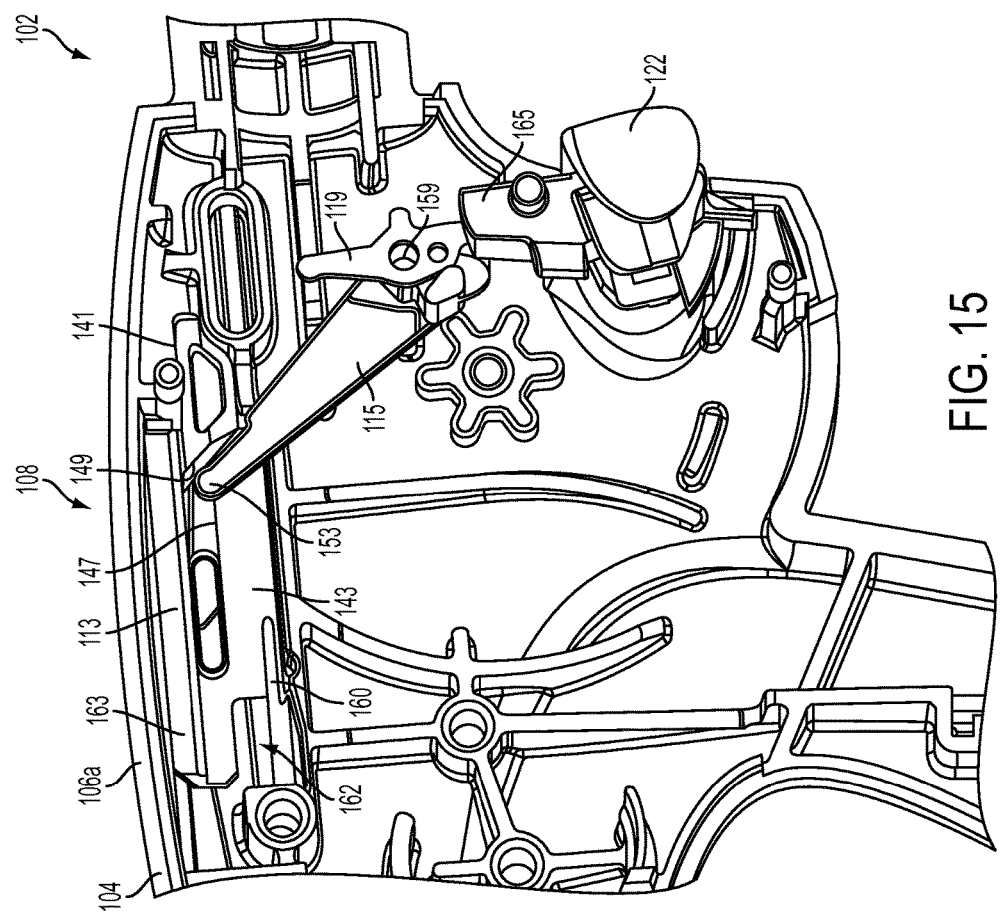
FIG. 15 is a perspective view of the surgical instrument shown in FIG. 3 with the right handle housing shroud removed, according to one embodiment.

FIGS. 14 and 15 provide additional views of the knife lockout disabling mechanism 108. FIG. 14 is a side elevational view of the surgical instrument 102 with the right handle housing shroud removed to expose various mechanisms located within the handle assembly 104 and the knife lockout mechanism enabled, according to one embodiment. FIG. 15 is a perspective view of the surgical instrument 102 with the right handle housing shroud removed to expose various mechanisms located within the handle assembly 104 and the knife lockout mechanism enabled, according to one embodiment.

With reference now to FIGS. 1, 2, 10, 11, 14, and 15, the knife lockout disabling mechanism 108 is coupled to one or more mechanisms for closing the jaw members 116a, 116b of the end effector 10 and deploying a cutting member (e.g., knife) therein. In one embodiment, when the trigger 109 is squeezed in direction C towards the pistol grip 118, the trigger 109 rotates the trigger plate 124 about a rotation point defined by a rotation pin 125a. Rotation of the trigger plate 124 to a first position causes a toggle clamp 145 to advance a yoke 132 and a closure actuator 129 configured to transition the jaw members 116a, 116b from an open position to a closed position. For example, in the illustrated embodiment, the toggle clamp 145 is operatively coupled to a yoke 132. The toggle clamp 145 is movably coupled to the trigger plate 124. Rotation of the trigger plate 124 also drives the yoke 132 distally. Distal movement of the yoke 132 compresses a closure spring 114, causing distal movement of the closure actuator 129. As previously discussed in connection with FIG. 2, distal movement of the closure actuator 112 compresses the closure spring 114. The closure spring 114 is coupled to the closure bar 142 via the spring-to-bar interface element 119. Accordingly, distal movement of the closure actuator 129 causes the closure bar 142 to pivotally move the first jaw member 116a from an open position to a closed position with respect to the second jaw member 116b, for example.

Rotation of the trigger plate 124 beyond a predetermined rotation such as, for example, the first rotation position, causes partial rotation of the firing plate 128. Rotation of the firing plate 128 deploys a cutting member within the end effector 110. For example, in the illustrated embodiment, the firing plate 128 comprises a sector gear operably coupled to a rack 136 through first and second pinions 133 and 134. The sector gear of the firing plate 128 comprises a plurality of teeth 131 configured to interface with the first pinion 133. The first pinion 133 drives the second pinion 134. Thus, rotation of the firing plate 128 rotates the first and second pinions 133 and 134 and drives the rack 136 distally. Distal movement of the rack 136 drives the cutting member actuator distally, causing deployment of the cutting member (e.g., knife) within the end effector 110. The rack 136, however, comprises at least one notch 58 configured to engage the lock arm 157. When the lock arm 157 engages the notch 58 in the rack 136, the rack 136 is prevented from firing distally. This is referred to as the lockout state. When the button 139 in position A, the energy button 122 must be depressed inwardly towards to pistol grip 118 to unlock the lock arm 57 and release the rack 136. When the button 139 in position B, the lockout mechanism is disabled by the lever arm 115 and the unlock arm 119 releasing the lock arm 157.

The trigger plate 124 is configured to interface with the toggle clamp 145 during rotation of the trigger 109 from an initial position to a first rotation position, for example. The trigger plate 124 is operably coupled to the firing plate 128. In certain instances, the firing plate 128 may include a first slot 128a and a second slot 128b. The first slot 128a receives a drive pin 148 coupled to the trigger plate 124. The drive pin 148 is slidably driven by the trigger plate 124 in the first slot 128a and drives the firing plate 128.

Rotation of the firing plate 128 by the drive pin 148 in the first slot 128a rotates the sector gear teeth 131 to rotate the first pinion 133. The first pinion 133 rotates the second pinion 134. The second pinion 134 drives the rack 136 distally to fire the cutting element (e.g., knife), but only when the lock arm 157 is released or disabled from the notch 158 in the rack 132 either by locating the button 139 in position B or pressing the energy button 122 to release the lockout element 165.

Figure 16:
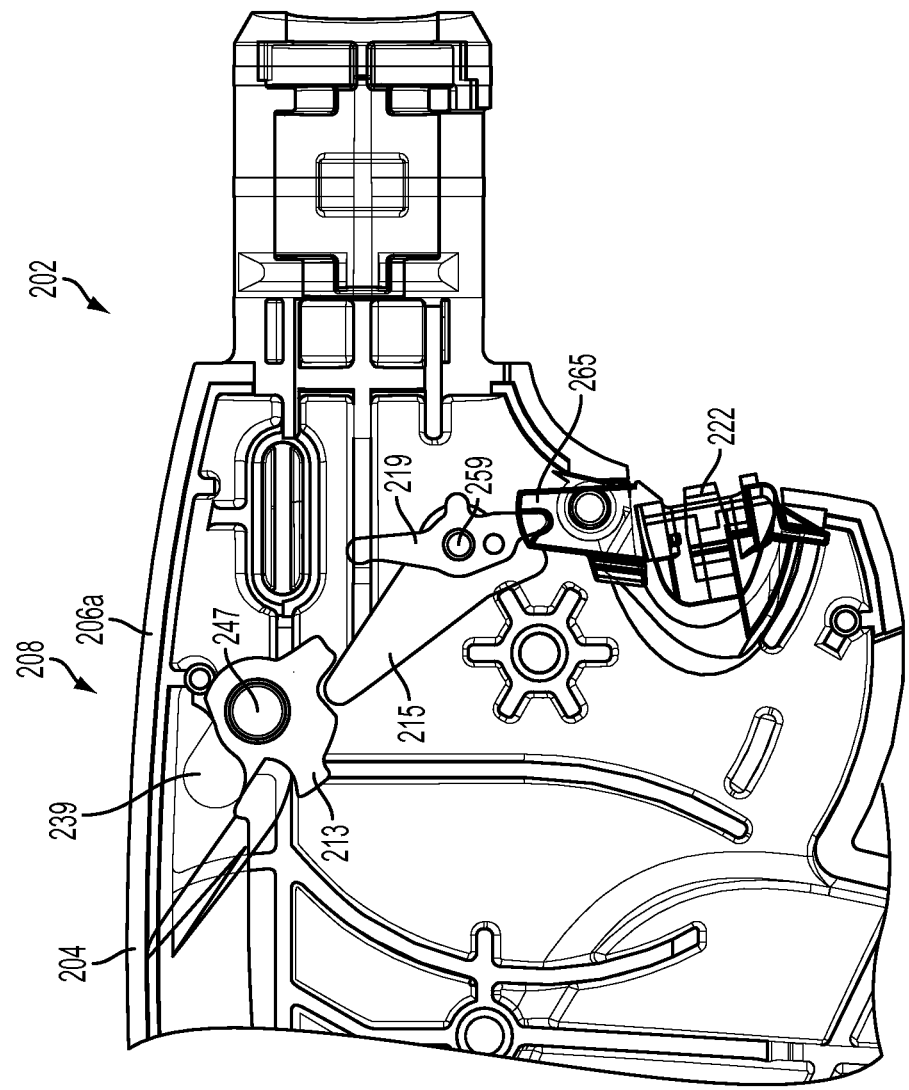
FIG. 16 is a side elevational view of the rotary knife lockout disabling mechanism for a surgical instrument where the knife lockout element is enabled, according to one embodiment.
Figure 17:
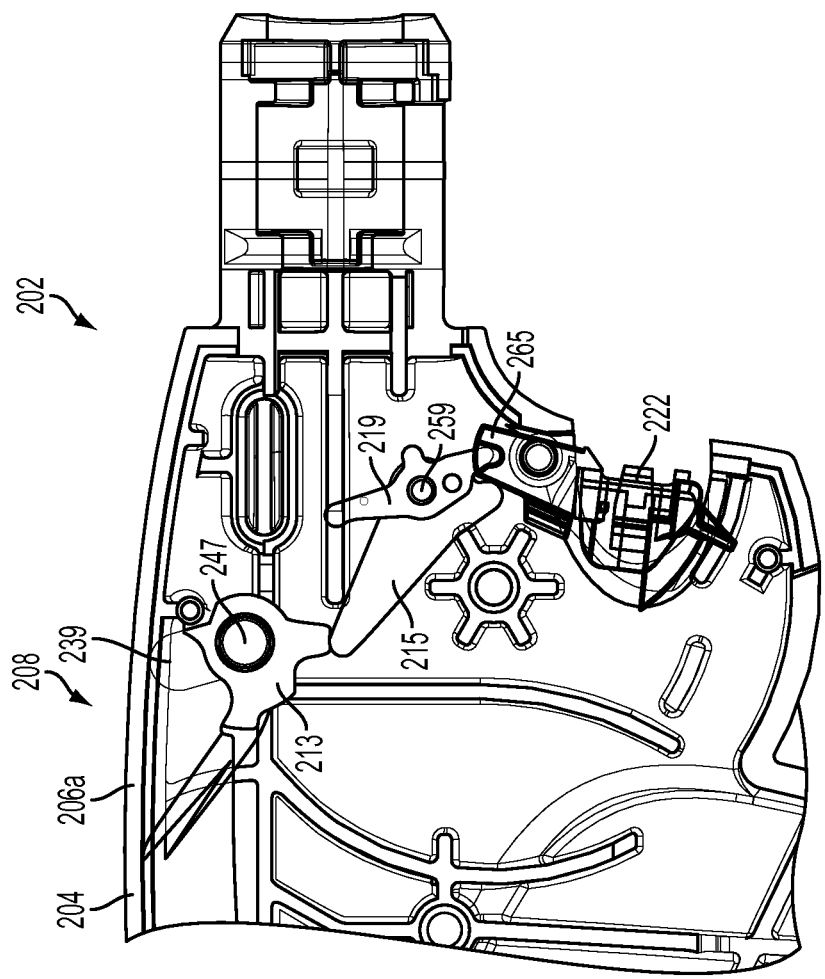
FIG. 17 is a side elevational view of the rotary knife lockout disabling mechanism for a surgical instrument where the knife lockout mechanism is disabled, according to one embodiment.

FIGS. 16 and 17 are side elevational views of a rotary knife lockout disabling mechanism 208 for a surgical instrument, according to one embodiment. FIG. 16 is a side elevational view of the rotary knife lockout disabling mechanism 208 for a surgical instrument where the knife lockout element 265 is enabled, according to one embodiment. FIG. 17 is a side elevational view of the rotary knife lockout disabling mechanism 208 for a surgical instrument where the knife lockout mechanism is disabled, according to one embodiment. As shown in FIGS. 16 and 17, in another embodiment, the knife lockout disabling mechanism 208 of the electrosurgical instrument 202 comprises a rotator 213, a lever arm 215, and a button 239 operatively coupled to the rotator 213 and is configured to disable, override, or otherwise turn off the knife lockout element 265 of the electrosurgical instrument 202. The button 239 can be engaged by the clinician to rotate the rotator 213 about a pivot point 247 between various positions. In one embodiment, the rotator 213 can be rotated about the pivot point 247 between two positions. The rotator 213 acts on the lever arm 215, which rotates a lock arm 219. The lock arm 219 rotates about a pivot point 259 and engages a surface of the lockout element 265 to rotate the lockout element 265 and thereby defeat the lockout mechanism of the electrosurgical instrument 202.

As shown in FIG. 16, the rotator 213 is positioned such that it can push on one end of the lever arm 215 when the rotator 213 is rotated in a first direction about the pivot point 247. The lever arm 215 and the lock arm 219 rotate about the pivot point 259 where the lock arm 219 rotates the lockout element 265 to the position shown in FIG. 17 to disable the knife lockout function. When the lever arm 215 is rotated about the pivot point 259 in the first direction, the lock arm 219 also rotates about the pivot point 259 in the same direction. The lock arm 219 then pushes on the lockout element 265 causing it to rotate in the opposite direction to unlock the knife lockout element 265, as shown in FIG. 17.

The above described knife lockout disabling mechanisms 8, 108, 208 provide several advantages over conventional electrosurgical devices with knife lockout mechanisms that cannot be disabled. For example, the lockout disabling mechanisms 8, 108, 208 according to the present disclosure can be configured to fit in a form factor of current electrosurgical instruments with only a change to one of the housing shrouds 6a, 6b, 106a, 106b, 206a, 206b. The lockout disabling mechanism 8, 108, 208 generally moves between two states (off or on). Thus, the button portion of the slider 13, 113 can be slidably translated and the rotator 213 can move rotatably between the two positions or states but not in any intermediate positions between the two states. In one embodiment, the button 39, 139, 239 can be retrofitted into some existing electrosurgical instruments and locks into place without requiring any additional or new components to lock it in position. The button 39, 139, 239 can be configured to employ a spring that is already provided for the energy button 22, 122, 222 as described herein. Also, either the slider or rotator is operatively coupled to the energy button such that when the knife lockout disabling mechanism is activated, it moves the energy button 22, 122, 222 inward to provide a visual and tactile clue that the knife lockout feature is turned off.

FIGS. 18-44 illustrate additional views of the surgical instrument 102 with the jaw members 116a, 116b, cutting member, and lockout mechanism in various modes of operation, according to one embodiment.

Figure 18:
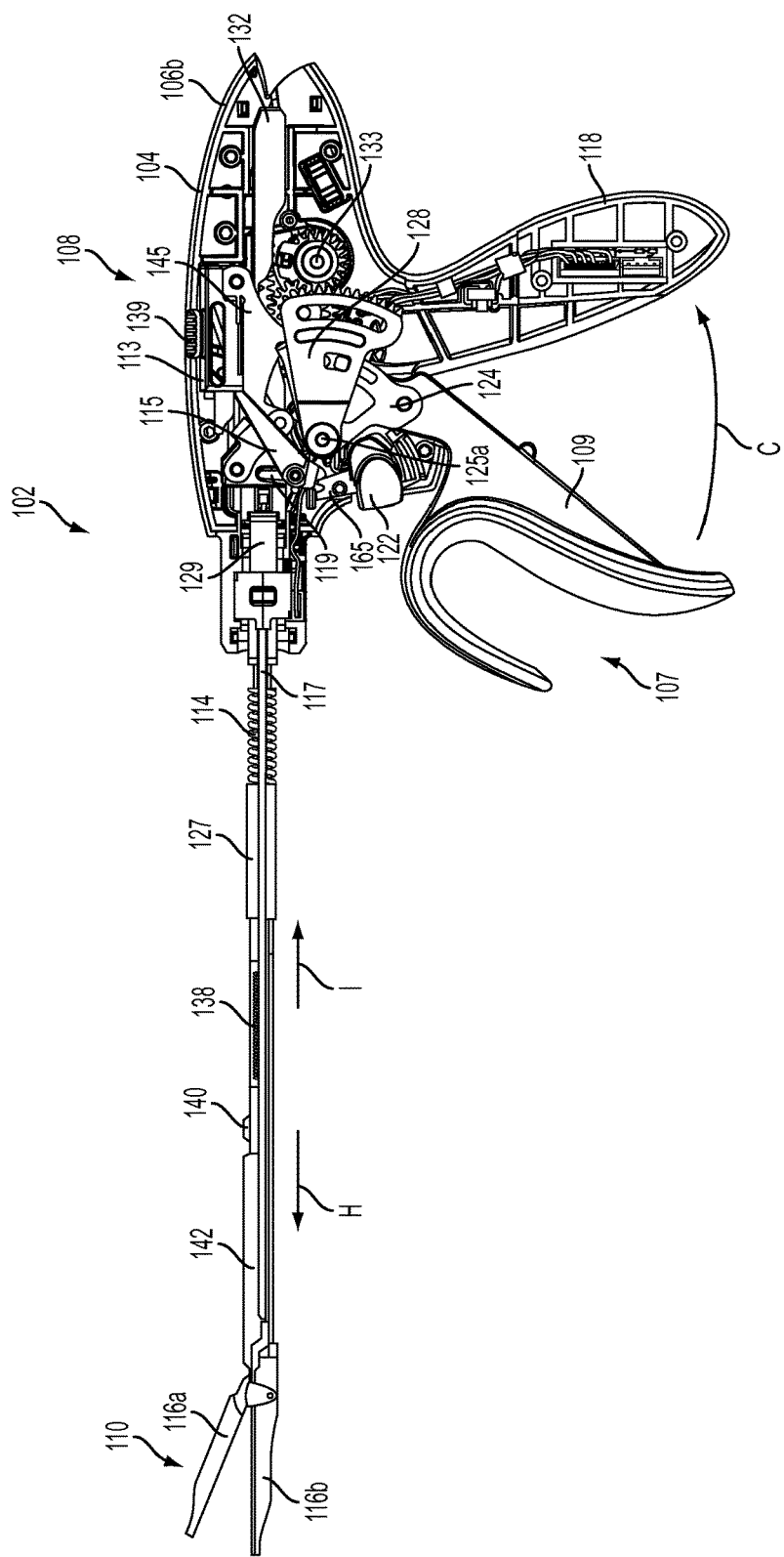
FIG. 18 is a side elevational view of the surgical instrument shown in FIGS. 1 and 2 with the left housing shroud removed, shaft assembly sheaths removed, the jaw fully open and the lockout defeat mechanism enabled, e.g., in the "ON" position, according to one embodiment.

FIGS. 18-25 illustrate the surgical instrument 102 shown in FIGS. 1 and 2 with the jaw 110 fully open and the lockout defeat mechanism 108 enabled, e.g., in the "ON" position. FIG. 18 is a side elevational view of the surgical instrument 102 shown in FIGS. 1 and 2 with the left housing 106a shroud removed, shaft assembly 112 sheaths removed, the jaw 110 fully open and the lockout defeat mechanism 108 enabled, e.g., in the "ON" position, according to one embodiment. Thus, the button 139 portion of the slider 113 is slidably moved proximally to locate it in the B position.

Figure 19:
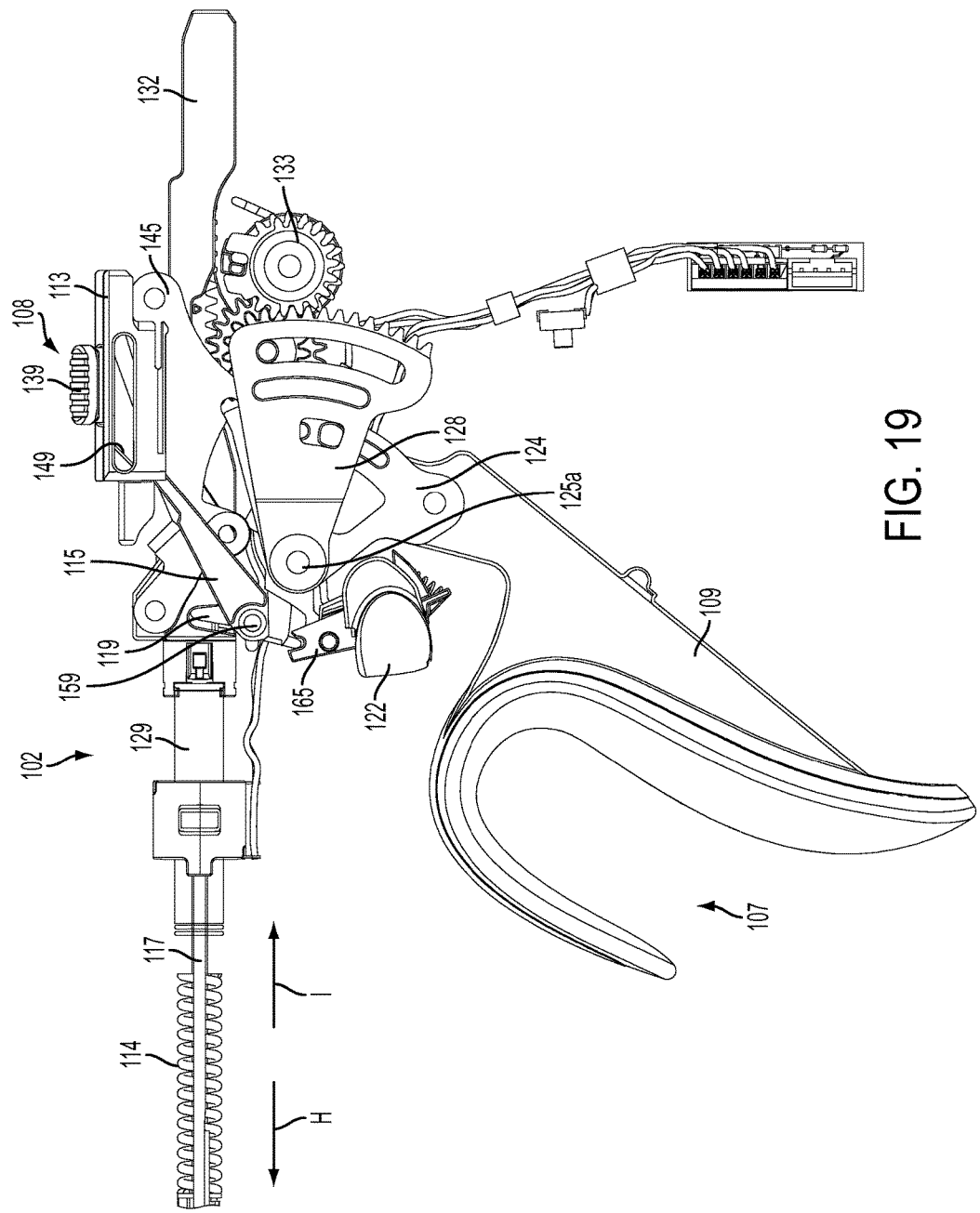
FIG. 19 is a side elevational view of the surgical instrument shown in FIG. 18 with the right housing shroud removed, according to one embodiment.
Figure 20:
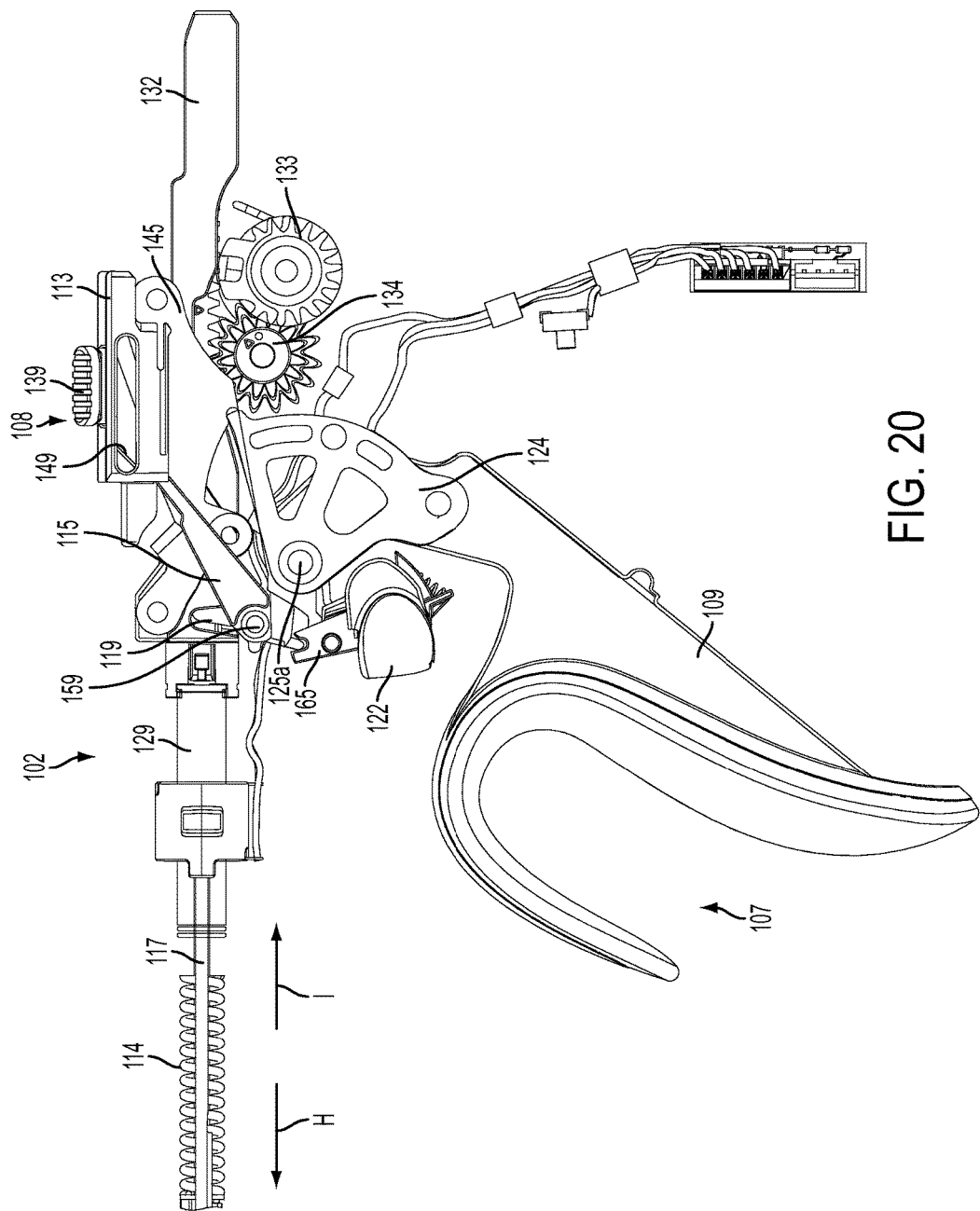
FIG. 20 is a side elevational view of the surgical instrument shown in FIG. 19 with the firing plate removed, according to one embodiment.
Figure 21:
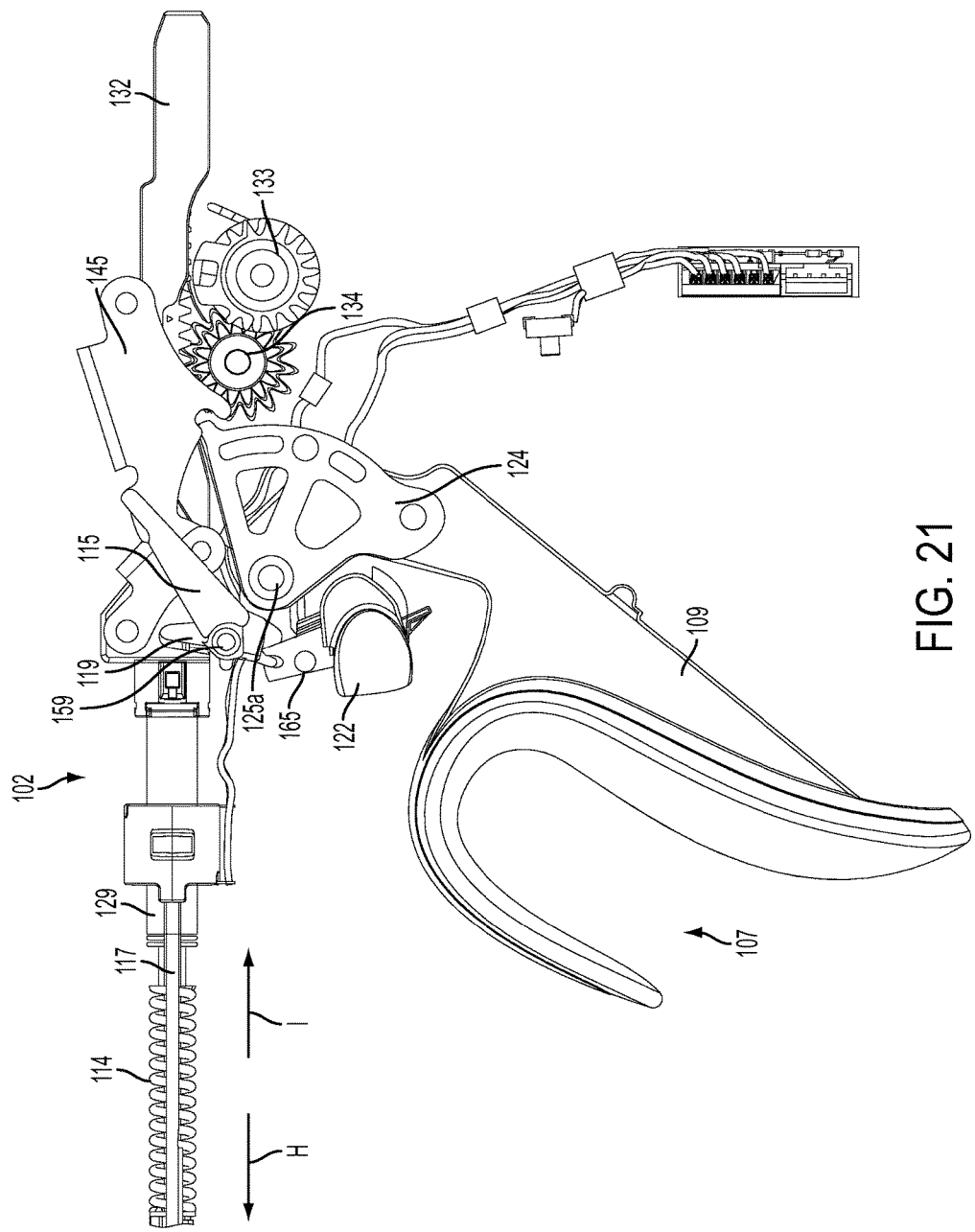
FIG. 21 is a side elevational view of the surgical instrument shown in FIG. 20 with the lockout defeat mechanism slider removed, according to one embodiment.
Figure 22:
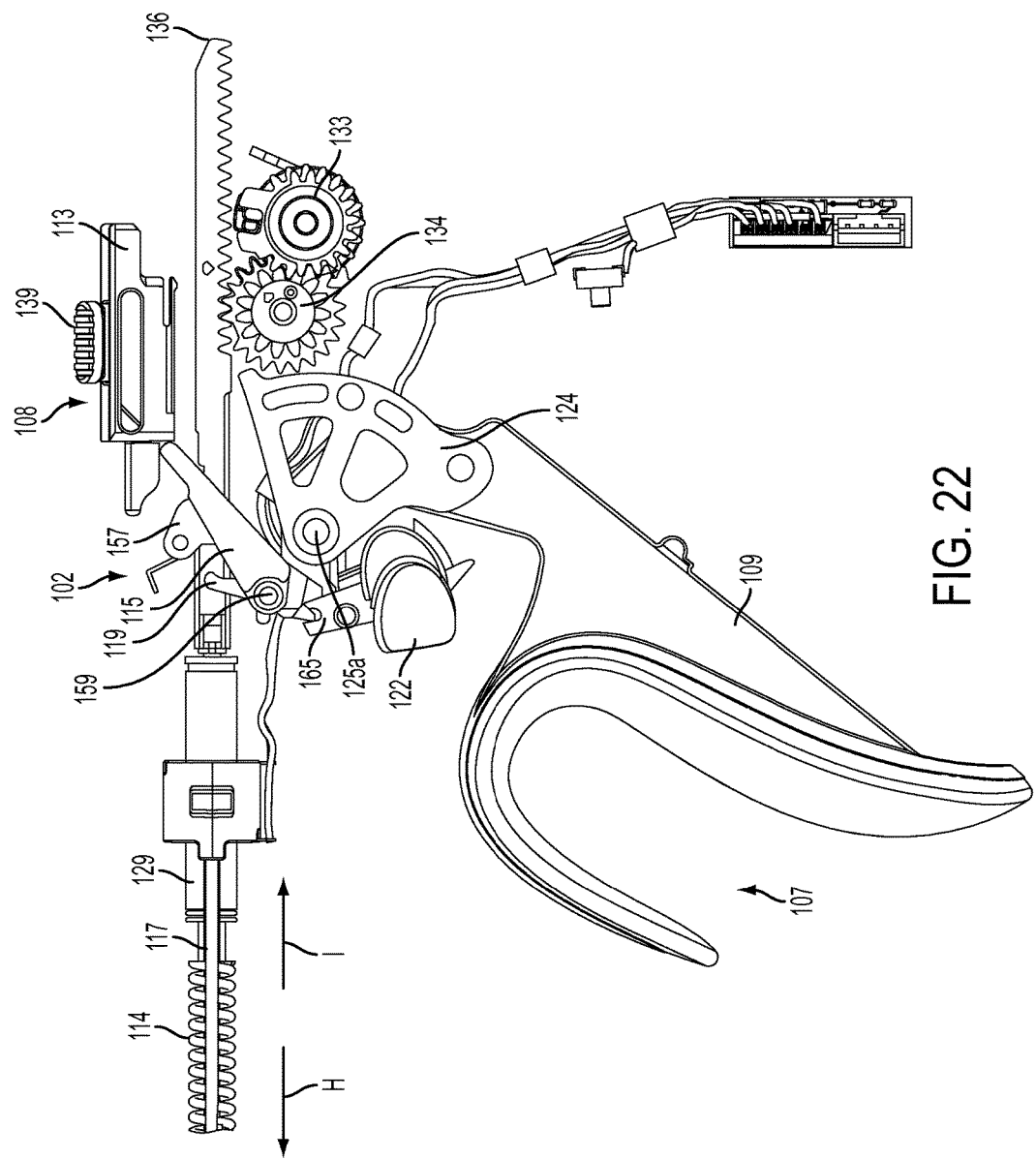
FIG. 22 is a side elevational view of the surgical instrument shown in FIG. 20 with the toggle clamp and yoke removed, according to one embodiment.
Figure 23:
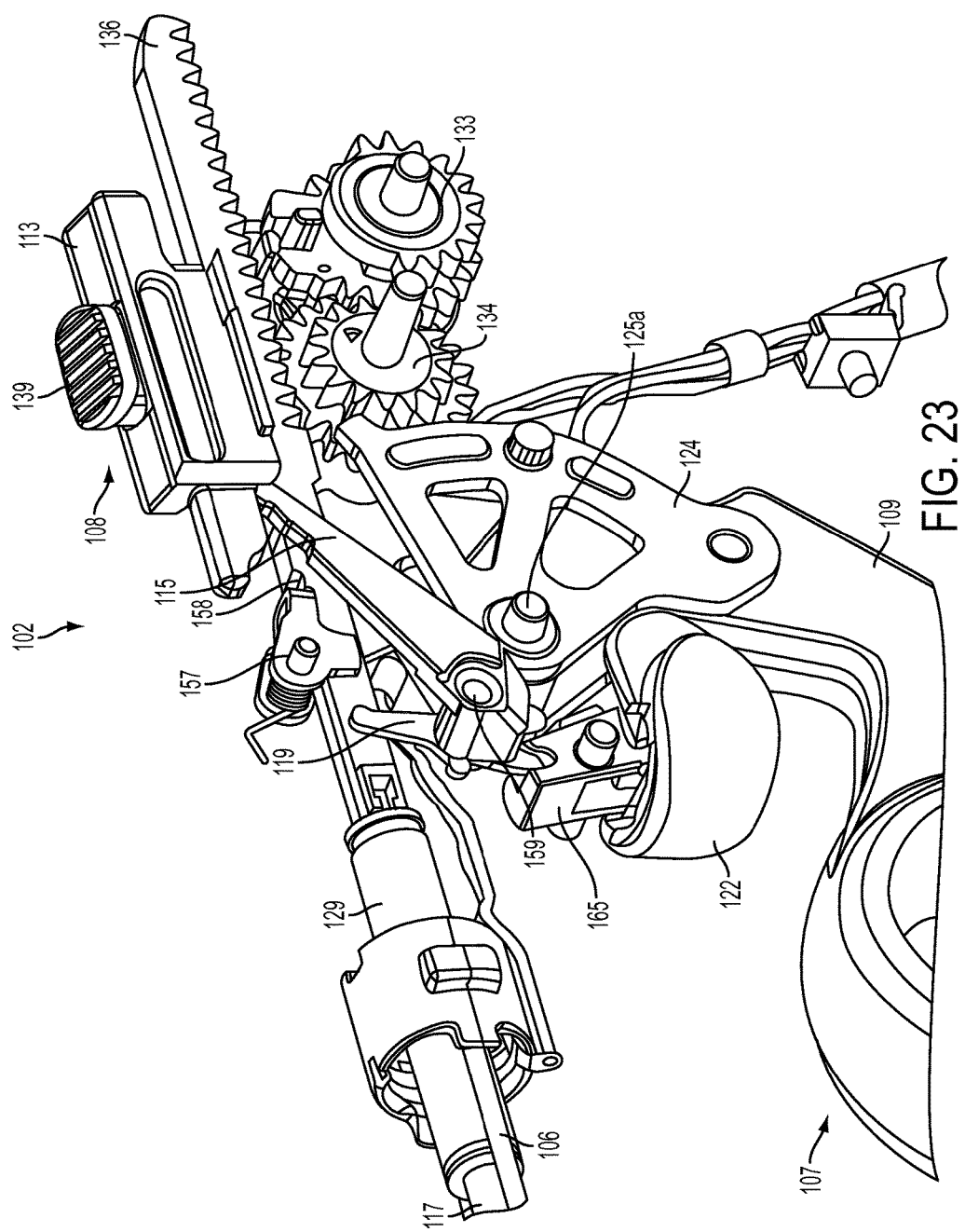
FIG. 23 is a partial perspective view of the surgical instrument shown in FIG. 22, according to one embodiment.
Figure 24:
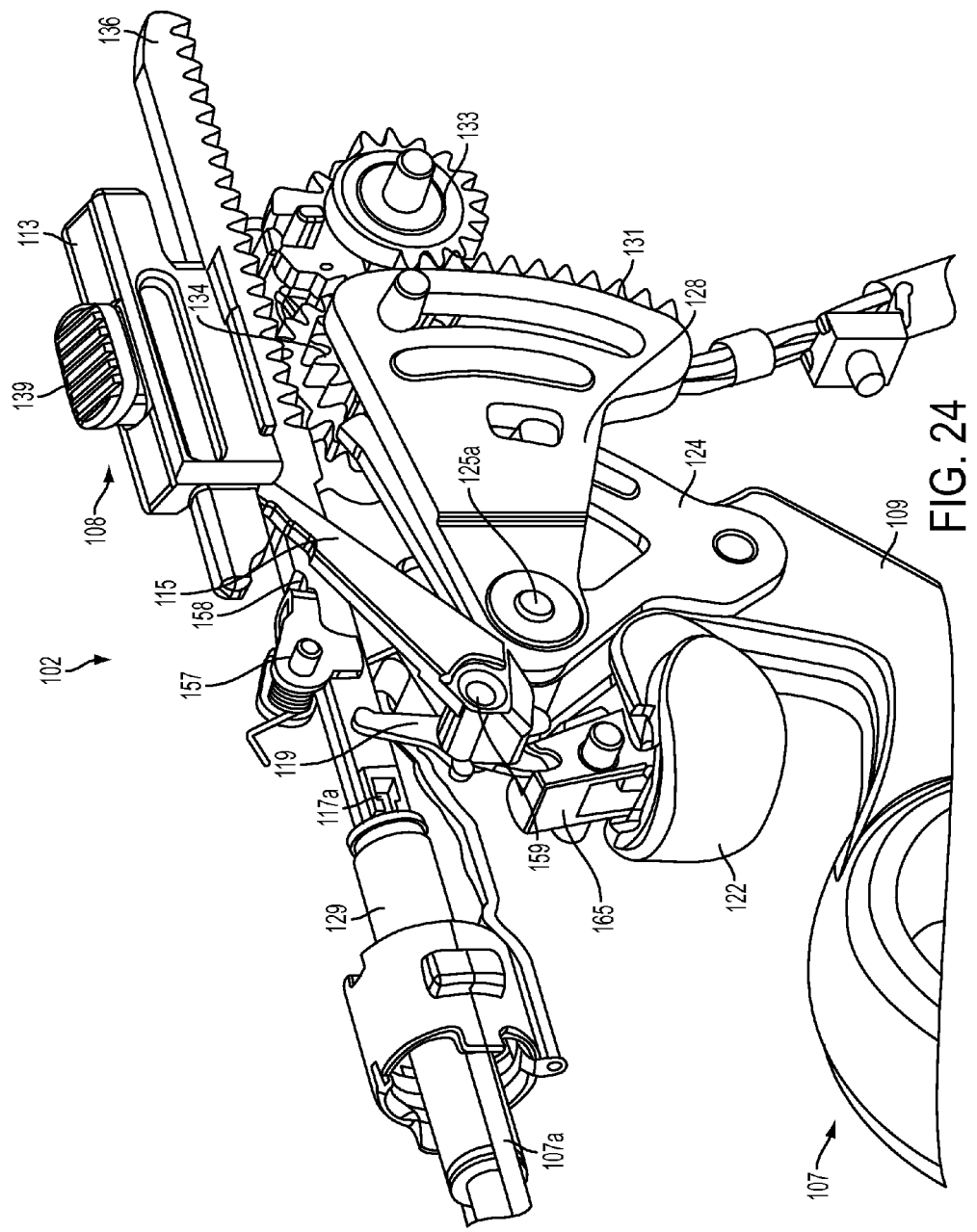
FIG. 24 is a partial perspective view of the surgical instrument shown in FIG. 23 with the firing plate replaced, according to one embodiment.
Figure 25:
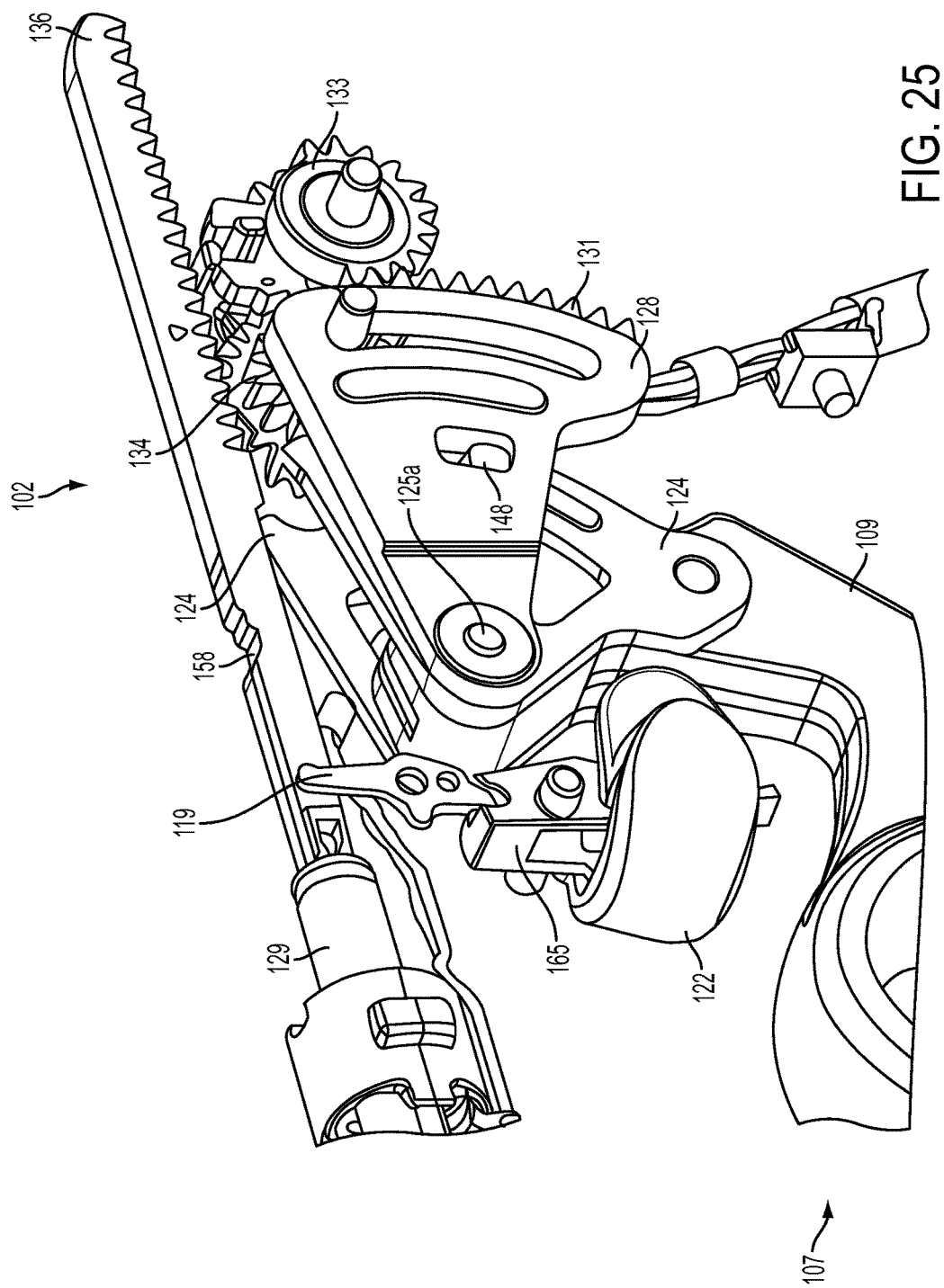
FIG. 25 is a partial perspective view of the surgical instrument shown in FIG. 24 with the lockout defeat mechanism slider, lever arm, and lock arm removed, according to one embodiment.

FIG. 19 is a side elevational view of the surgical instrument 102 shown in FIG. 18 with the right housing shroud 106b removed, according to one embodiment. The trigger 109 is located in the maximum distal position and the trigger plate 124 is engaged with the toggle clamp 145 and yoke 132, which are located in the maximum proximal position to set the jaws 110 in the fully open position. The slider 113 is set to the maximum proximal "B" position where the ramp 149 has rotated the lever arm 115. The lever arm 115 rotates the unlock arm 119 clockwise and the lockout element 165 counterclockwise to enable the lockout defeat mechanism 108. The lockout element 165 also depresses the energy button 122 to indicate that the lockout defeat mechanism 108 enabled in the "ON" position. This view also shows the position of the firing plate 128 sector gear meshed with the first pinion 133 prior to firing the cutting element. FIG. 20 is a side elevational view of the surgical instrument shown in FIG. 19 with the firing plate 128 removed, according to one embodiment. This view illustrates the position of the trigger 109 relative to the trigger plate 124, the toggle clamp 145, and the yoke 132. This view also shows the first pinion 133 meshed with the second pinion 134 which located behind the firing plate 128. FIG. 21 is a side elevational view of the surgical instrument 102 shown in FIG. 20 with the lockout defeat mechanism slider 113 removed, according to one embodiment, to better illustrate the position of the toggle clamp 145 when the jaws 110 are fully open. FIG. 22 is a side elevational view of the surgical instrument 102 shown in FIG. 20 with the toggle clamp 145 and the yoke 132 removed, according to one embodiment. This view shows the position of the rack 136 and the lock arm 157 relative to the position of the slider 113. In addition, this view shows the second pinion 134 meshed with the rack 136 when the cutting element has not yet been fired. FIG. 23 is a partial perspective view of the surgical instrument 102 shown in FIG. 22, according to one embodiment, which more clearly shows the lock arm 157 located in the notch 158 formed on top of the rack 136. When the unlock arm 119 is in the indicated position, as the toggle clamp 145 and yoke move in the distal direction, the unlock arm 119 acts on the lock arm 157 to disengage the lock arm 157 from the notch 158 in the rack 136 to defeat the lockout mechanism. Therefore, the rack 136 is able to advance distally when the firing plate 128 is rotated by the trigger 109. FIG. 24 is a partial perspective view of the surgical instrument shown in FIG. 23 with the firing plate 128 replaced, according to one embodiment, to show the relative position of the firing plate 128, the first and second pinions 133, 134 and the rack 136 prior to firing the cutting element. FIG. 25 is a partial perspective view of the surgical instrument 102 shown in FIG. 24 with the lockout defeat mechanism slider 113, lever arm 115, and lock arm 157 removed, according to one embodiment, to show the notch 158 or slot formed on top of the rack 136. As previously discussed, the lock arm 157 engages the notch 158 to prevent the rack 136 from advancing distally to fire the cutting element in response to the squeezing the trigger 109.

Figure 26:
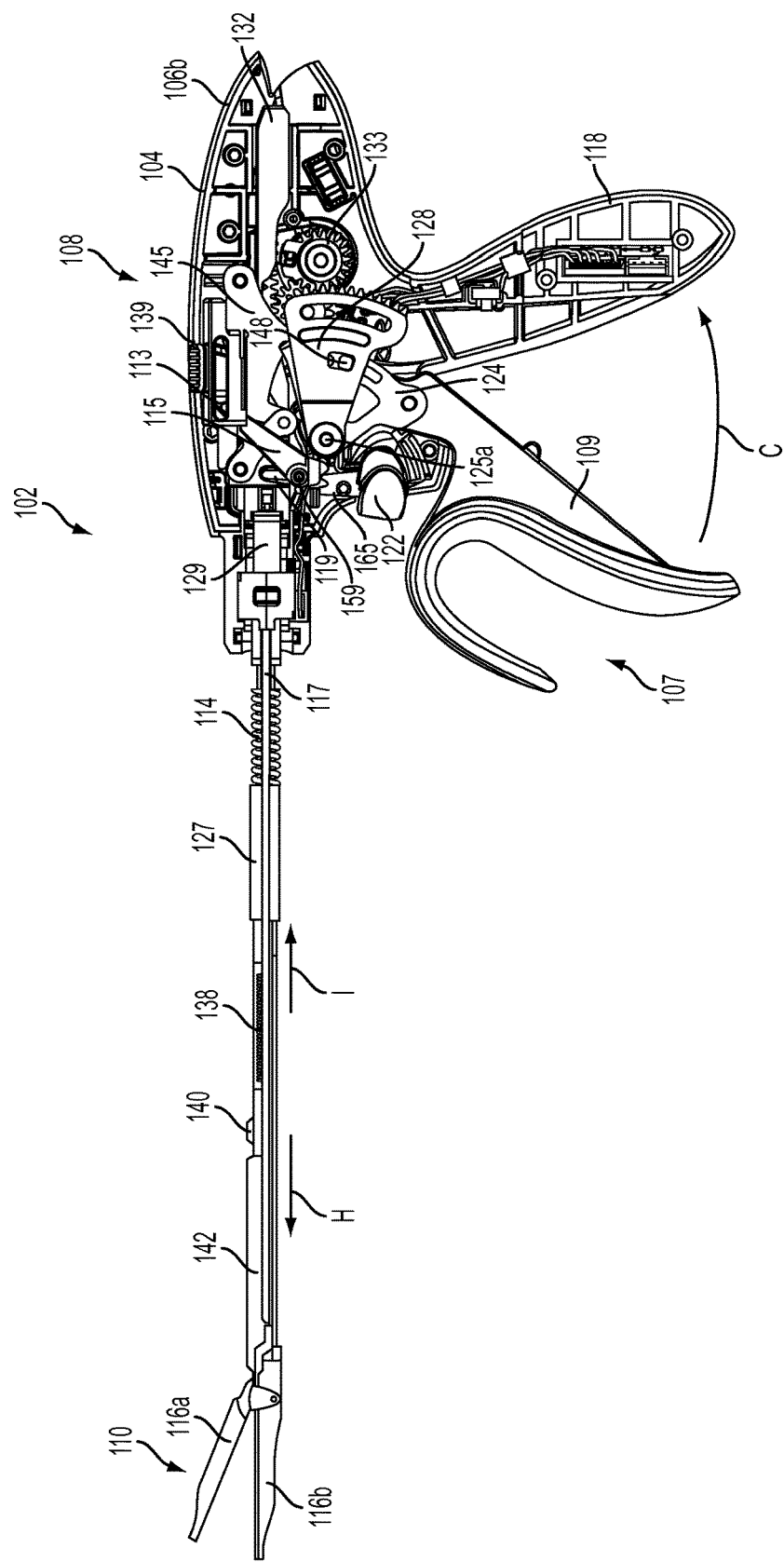
FIG. 26 is a side elevational view of the surgical instrument shown in FIGS. 1 and 2 with the left housing shroud removed, shaft assembly sheaths removed, the jaw fully open and the lockout defeat mechanism disabled, e.g., in the "OFF" position, according to one embodiment.
Figure 27:
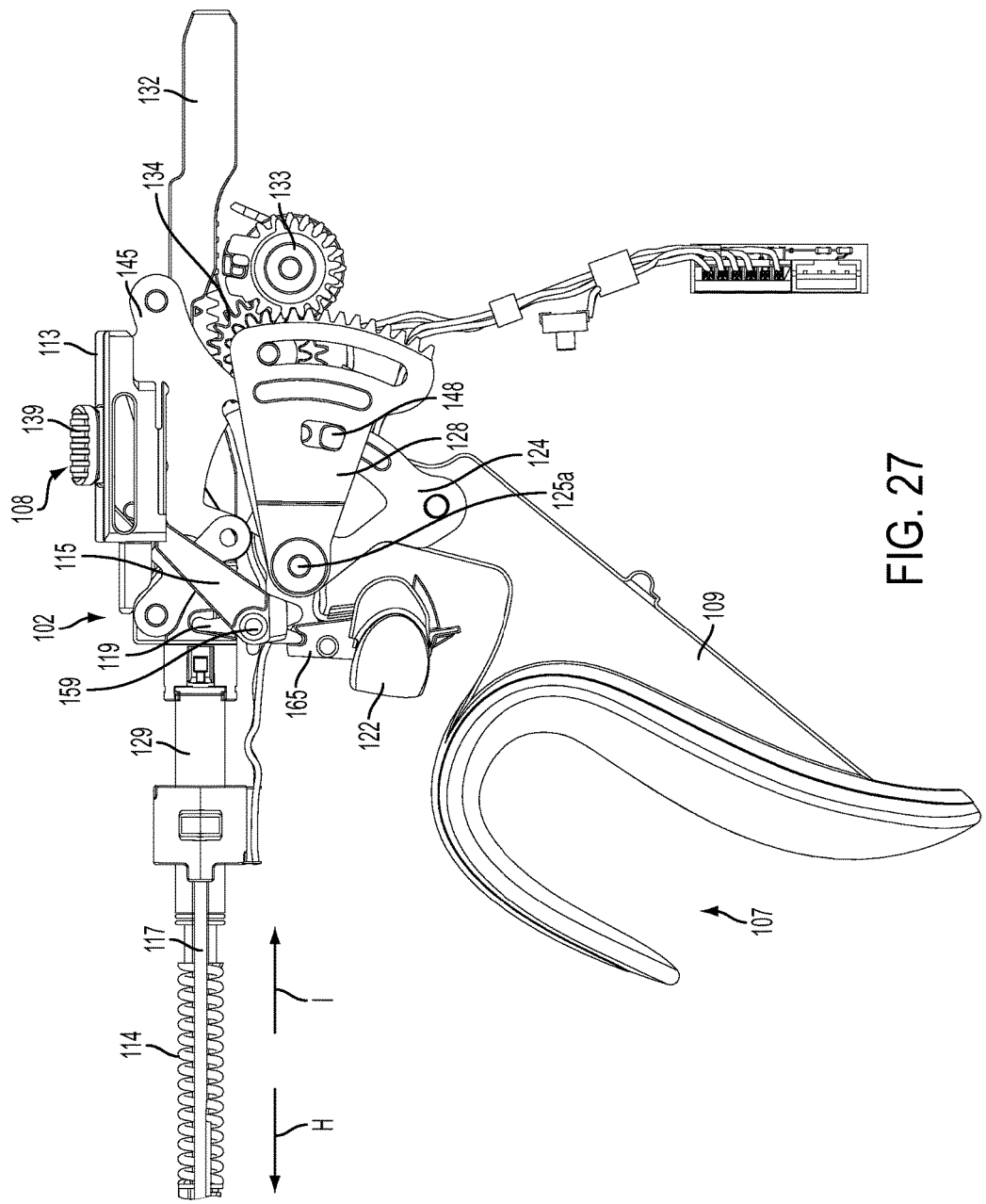
FIG. 27 is a side elevational view of the surgical instrument shown in FIG. 26 with the right housing shroud removed, according to one embodiment.
Figure 28:
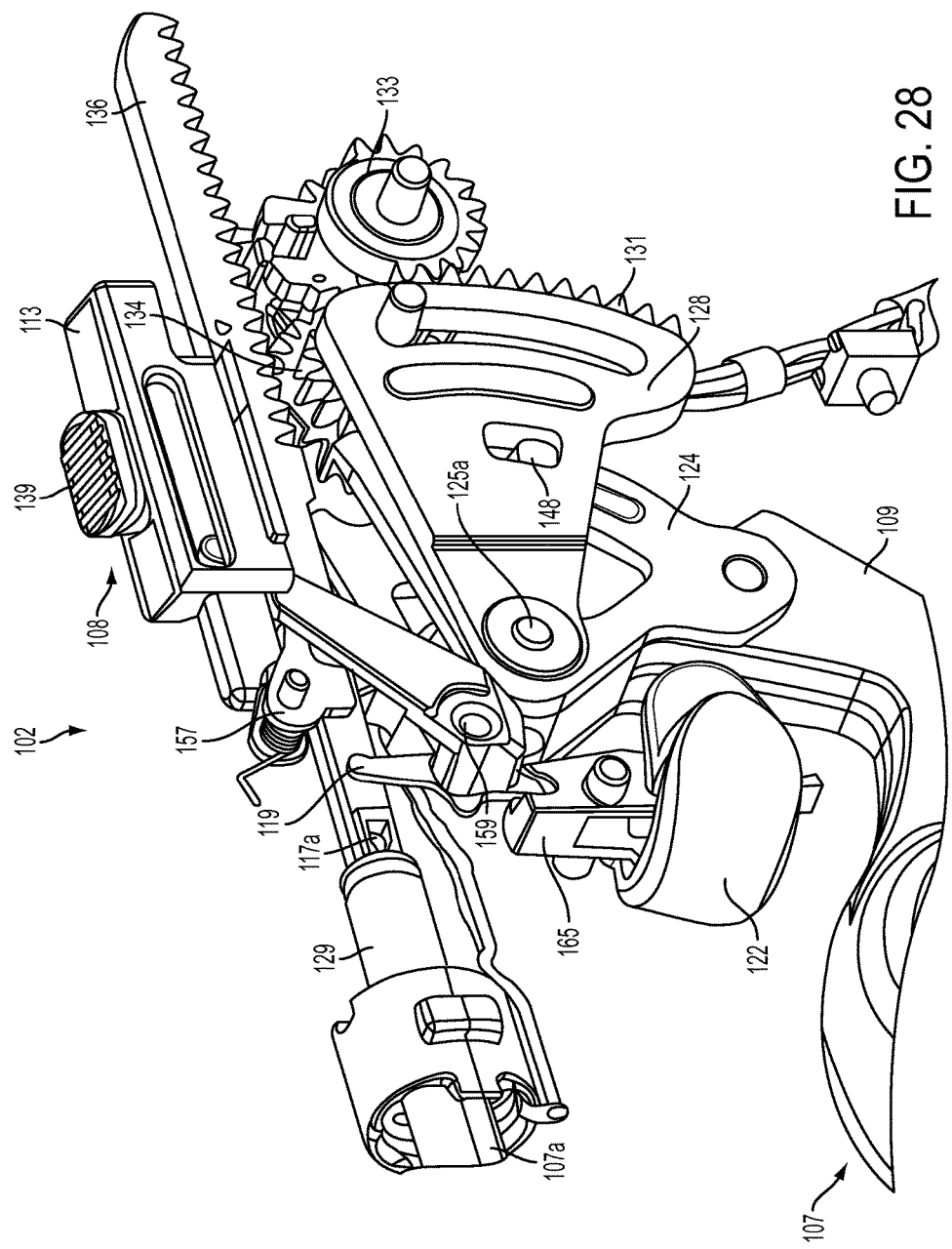
FIG. 28 is a partial perspective view of the surgical instrument shown in FIG. 27 with the toggle clamp and yoke removed, according to one embodiment.

FIGS. 26-28 illustrate the surgical instrument 102 shown in FIGS. 1 and 2 with the jaw 110 fully open and the lockout defeat mechanism 108 disabled, e.g., in the "OFF" position. FIG. 26 is a side elevational view of the surgical instrument 102 shown in FIGS. 1 and 2 with the left housing shroud 106a removed, shaft assembly 112 sheaths removed, the jaw 110 fully open and the lockout defeat mechanism 108 disabled, e.g., in the "OFF" position, according to one embodiment. Thus, the button 139 portion of the slider 113 is slidably moved distally to locate it in the A position. FIG. 27 is a side elevational view of the surgical instrument 102 shown in FIG. 26 with the right housing shroud 106b removed, according to one embodiment. The trigger 109 is located in the maximum distal position and the trigger plate 124 is engaged with the toggle clamp 145 and yoke 132, which are located in the maximum proximal position to set the jaws 110 in the fully open position. The slider 113 is set to the maximum distal "A" position. The lever arm 115 holds the unlock arm 119 and the lockout element 165 in a substantially vertical position to disable the lockout defeat mechanism 108 and enable the lockout mechanism. This view also shows the position of the firing plate 128 sector gear meshed with the first pinion 133 prior to firing the cutting element. FIG. 28 is a partial perspective view of the surgical instrument 102 shown in FIG. 27 with the toggle clamp 145 and yoke 132 removed, according to one embodiment. As shown, the unlock arm 119 is located in a substantially vertical position. Accordingly, as the toggle clamp 145 and the yoke 132 slide distally, the lock arm 157 will not contact the unlock arm 119 and the lock arm 157 remains engaged with the notch 158 in the rack 136. In this configuration, the lockout mechanism is enabled and to fire the rack 136, the energy button 122 must be depressed to rotate the lockout element 165 counterclockwise to rotate the unlock arm 119 clockwise and in response rotate the lock arm 157 counterclockwise to disengage it from the notch 158 in the rack 136.

Figure 29:
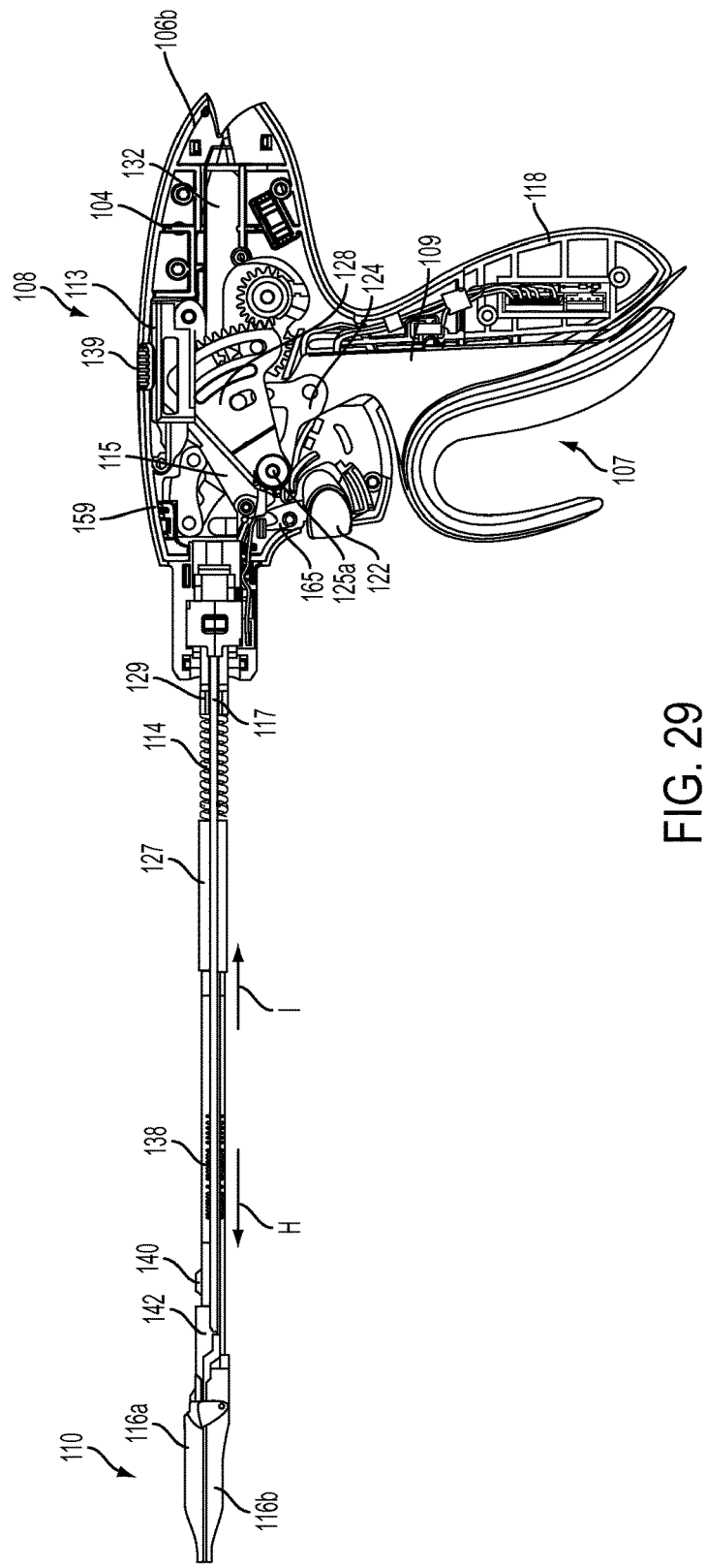
FIG. 29 is a side elevational view of the surgical instrument shown in FIGS. 1 and 2 with the left housing shroud removed, shaft assembly sheaths removed, the jaw fully closed, knife fully fired, and the lockout defeat mechanism enabled, e.g., in the "ON" position, according to one embodiment.
Figure 30:
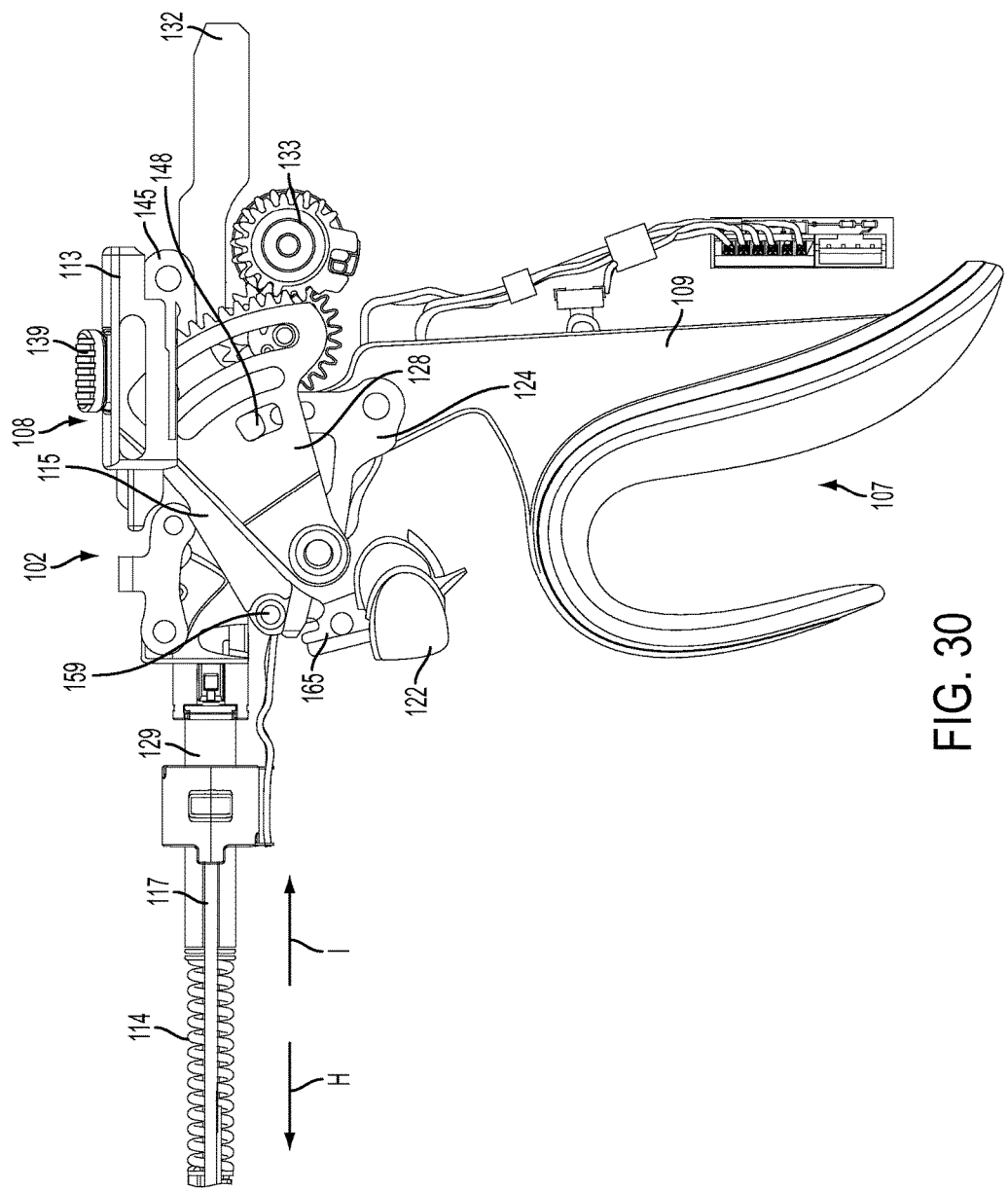
FIG. 30 is a side elevational view of the surgical instrument shown in FIG. 29 with the right housing shroud removed, according to one embodiment.
Figure 31:
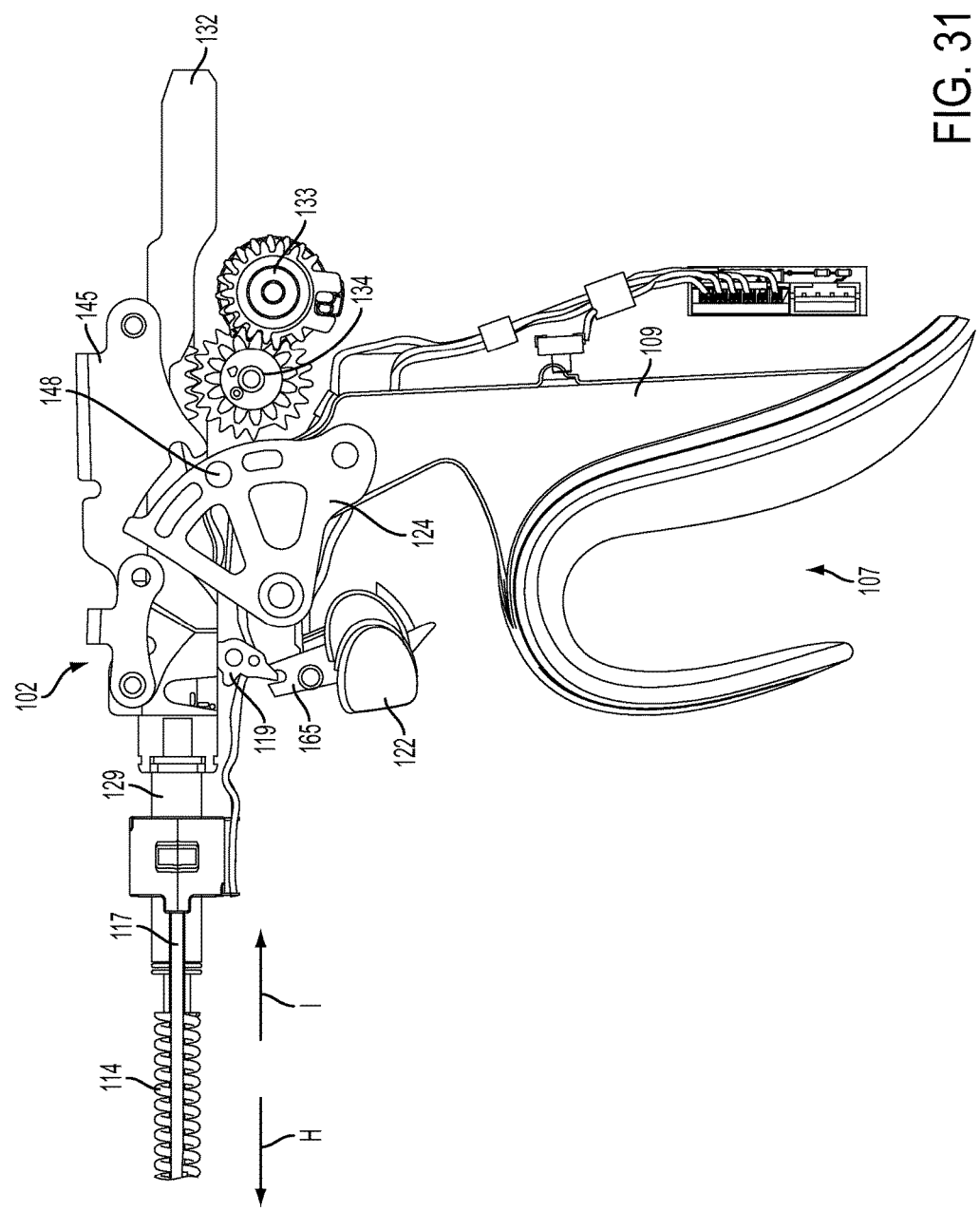
FIG. 31 is a side elevational view of the surgical instrument shown in FIG. 30 with the lockout defeat mechanism slider, lever arm, and firing plate removed, according to one embodiment.
Figure 32:
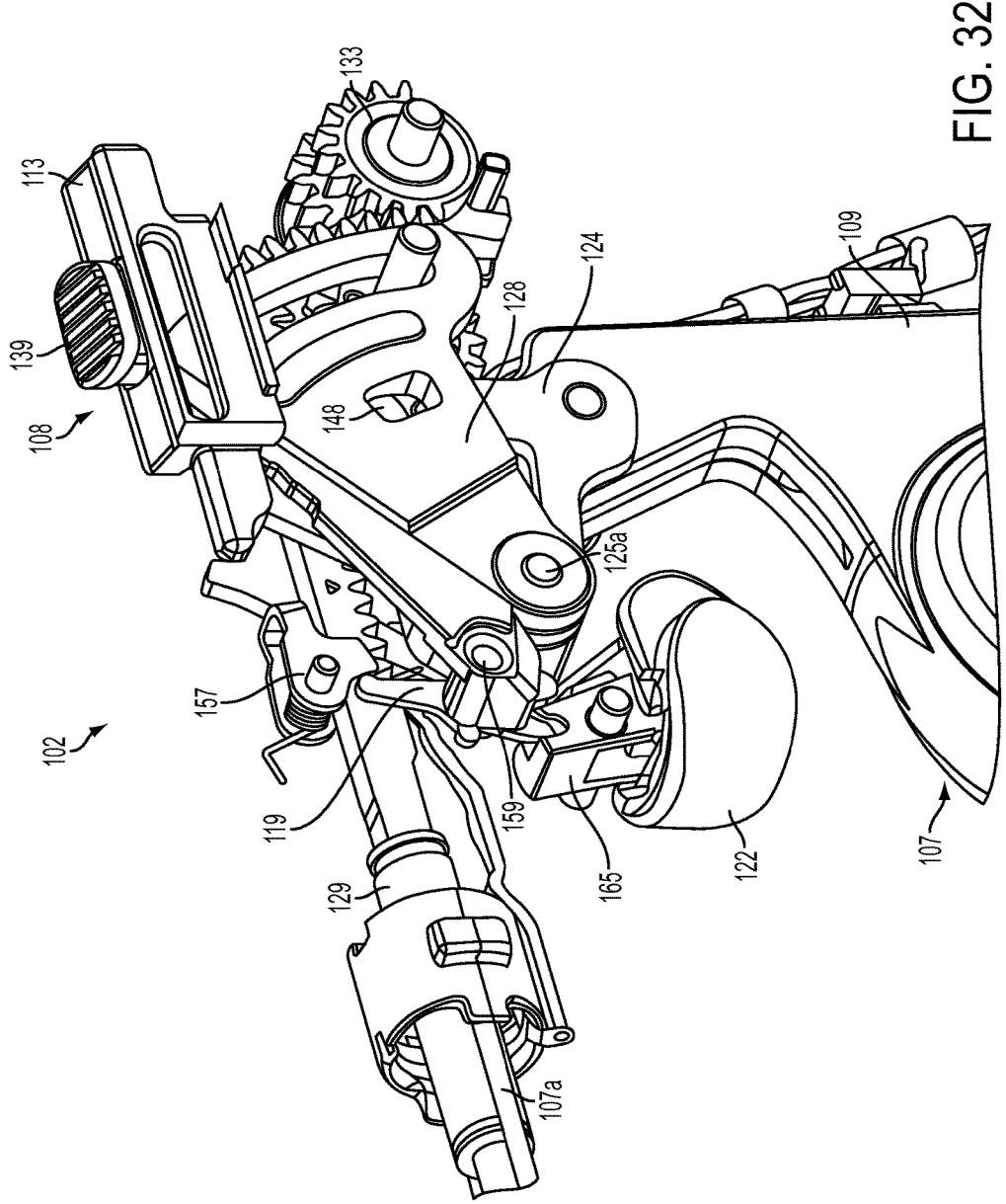
FIG. 32 is a partial perspective view of the surgical instrument shown in FIG. 30, according to one embodiment.

FIGS. 29-32 illustrate the surgical instrument 102 shown in FIGS. 1 and 2 with the jaw 110 fully closed, knife fully fired, and the lockout defeat mechanism 108 enabled, e.g., in the "ON" position. FIG. 29 is a side elevational view of the surgical instrument 102 shown in FIGS. 1 and 2 with the left housing shroud 106a removed, shaft assembly 112 sheaths removed, the jaw 110 fully closed, knife fully fired, and the lockout defeat mechanism 108 enabled, e.g., in the "ON" position, according to one embodiment. FIG. 30 is a side elevational view of the surgical instrument 102 shown in FIG. 29 with the right housing shroud 106b removed, according to one embodiment. As shown, the trigger 109 is squeezed fully proximally in direction C to straighten the toggle clamp 145 and advance the yoke 132 distally in direction H to push on the closure actuator and close the jaws 110. Further, the firing plate 128 is shown fully rotated in the counterclockwise to fully fire the knife. As previously discussed, the slider 113 has been slidably moved proximally in direction I to position B to rotate the lever arm 115 and the unlock arm 119 clockwise to rotate the lockout element 165 counterclockwise in response. When the slider 113 is located in position B, the unlock arm 119 will unlock, e.g., disengage, the lock arm 157 from the notch 158 to enable the rack 136 to move proximally in direction I in response to the firing plate 128 rotating counterclockwise while engaged to the first pinion 133. The first pinion 133 rotates clockwise and which in turn rotates the second pinion 134 counterclockwise to drive the rack 136 distally in direction H to drive the firing bar 117 and the knife distally in direction H. FIG. 31 is a side elevational view of the surgical instrument 102 shown in FIG. 30 with the lockout defeat mechanism slider 113, lever arm 119, and firing plate 128 removed, according to one embodiment, to show the position of trigger plate 124, toggle clamp 145, and yoke 132 when the jaws 110 are in the fully closed position. FIG. 32 is a partial perspective view of the surgical instrument 102 shown in FIG. 30, according to one embodiment. In this view, the unlock arm 119 is shown engaged with the lock arm 157 to release the lock arm 157 from the notch 158 in the rack 136 to enable the rack 136 to slide distally in direction H and fire the knife.

Figure 33:
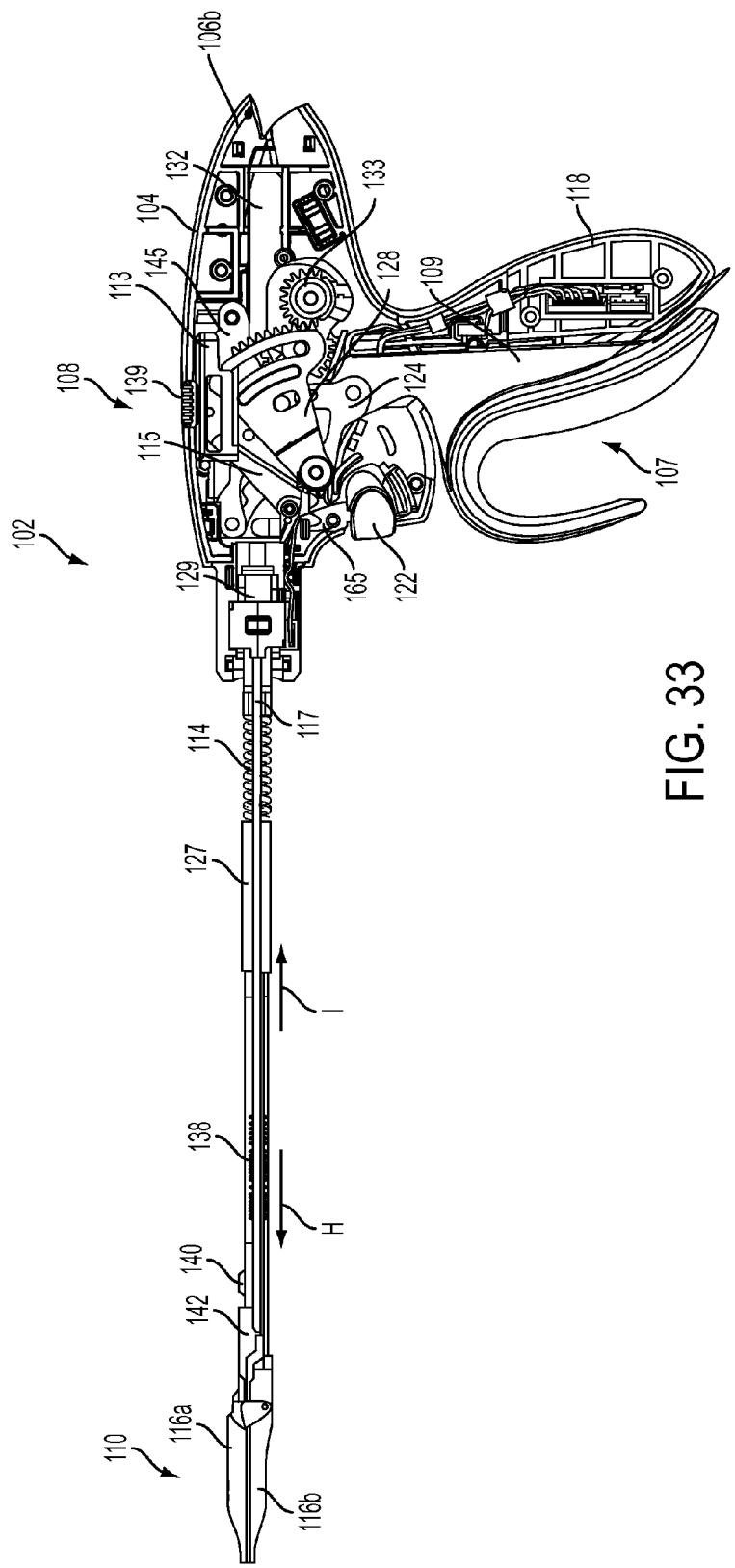
FIG. 33 is a side elevational view of the surgical instrument shown in FIGS. 1 and 2 with the left housing shroud removed, shaft assembly sheaths removed, jaw fully closed, knife fully fired, and lockout defeat mechanism disabled, e.g., in the "OFF" position, according to one embodiment.
Figure 34:
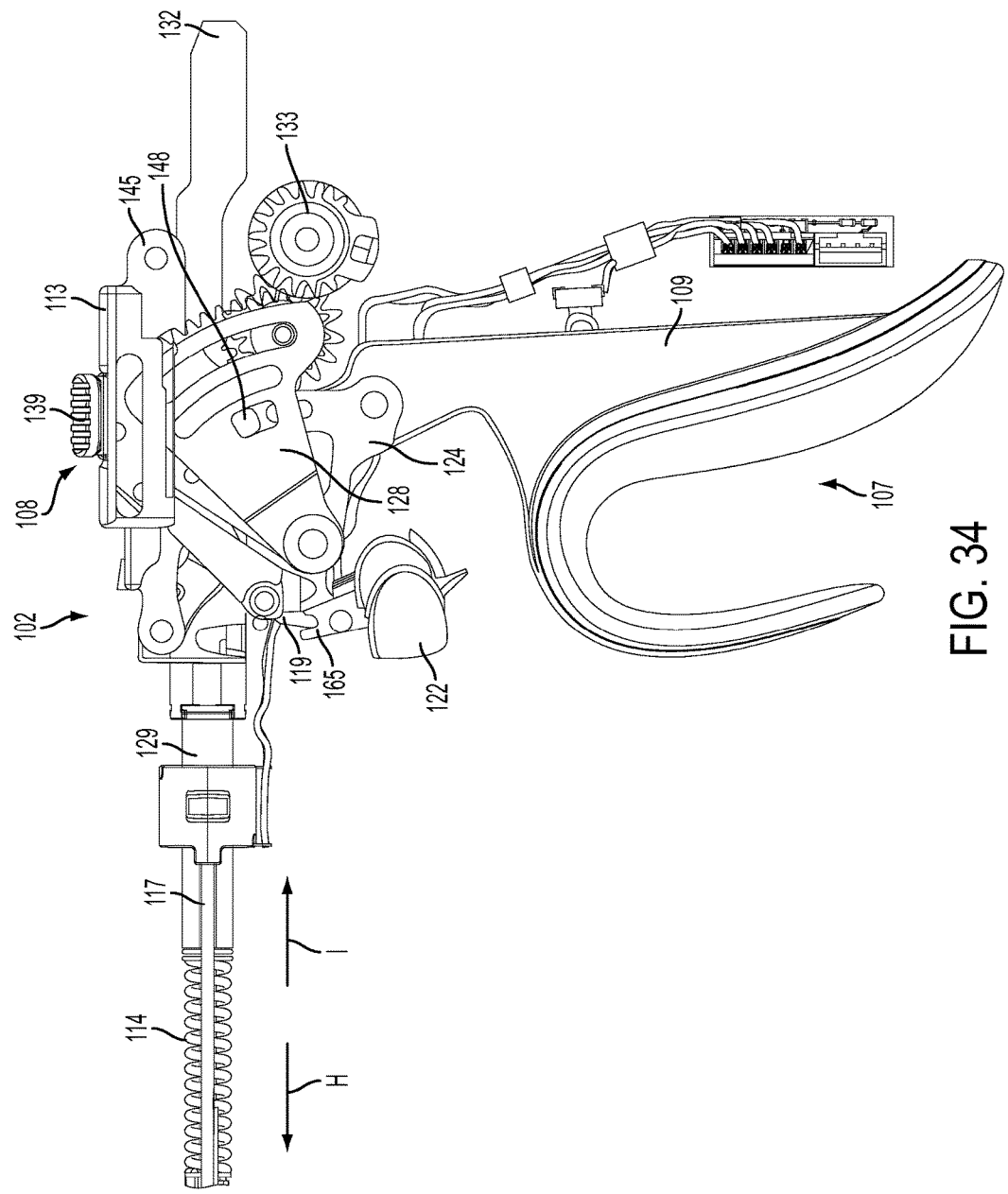
FIG. 34 is a side elevational view of the surgical instrument shown in FIG. 33 with the right housing shroud removed, according to one embodiment.
Figure 35:
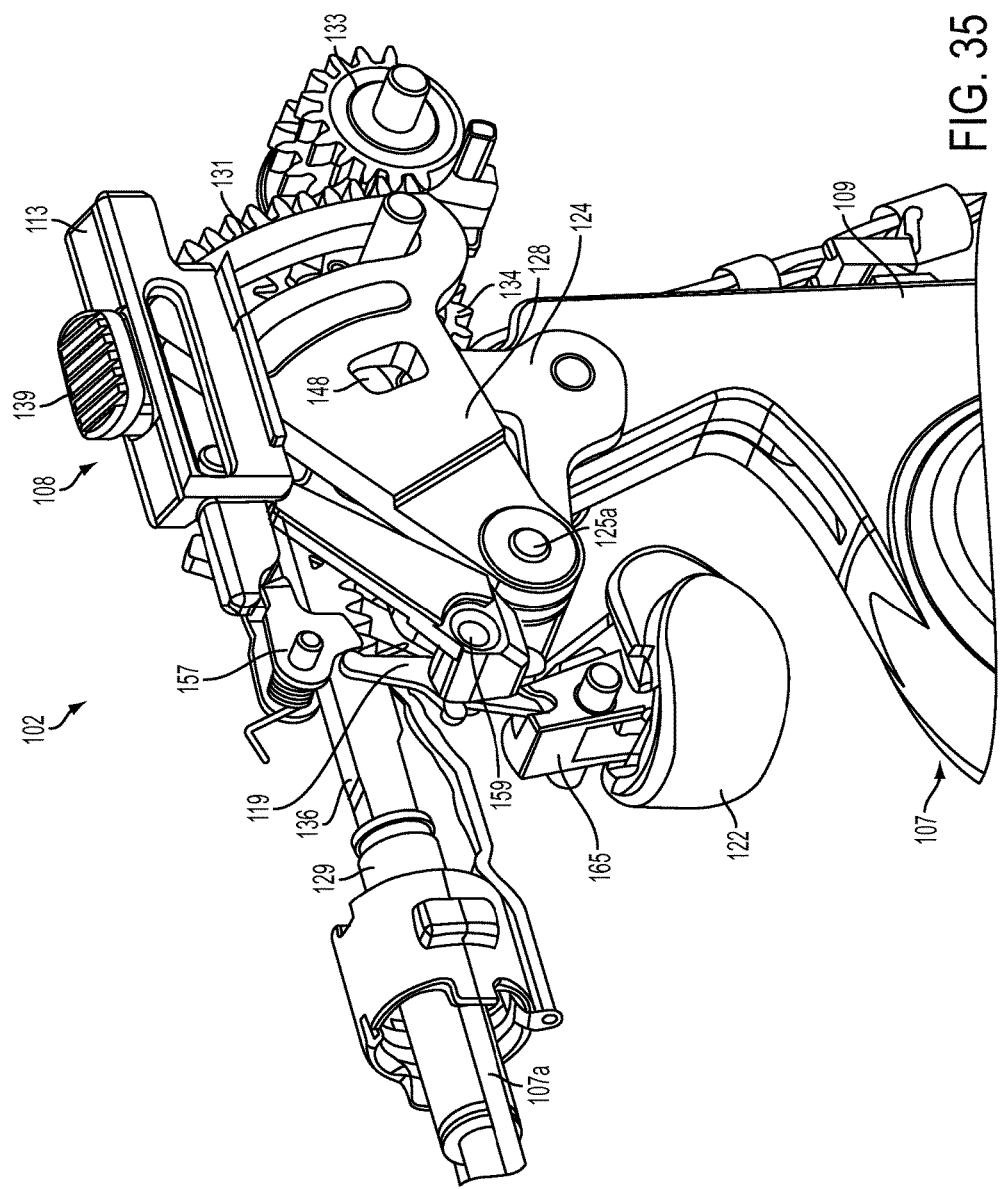
FIG. 35 is a partial perspective view of the surgical instrument shown in FIG. 34, according to one embodiment.

FIGS. 33-35 illustrate the surgical instrument 102 shown in FIGS. 1 and 2 with the jaw 110 fully closed, knife fully fired, and the lockout defeat mechanism 108 disabled, e.g., in the "OFF" position. FIG. 33 is a side elevational view of the surgical instrument shown in FIGS. 1 and 2 with the left housing shroud removed, shaft assembly sheaths removed, the jaw fully closed and the lockout defeat mechanism disabled in the "OFF" position, according to one embodiment. FIG. 34 is a side elevational view of the surgical instrument 102 shown in FIG. 33 with the right housing shroud 106b removed, according to one embodiment. Thus, the button 139 portion of the slider 113 is slidably moved distally to locate it in the A position. To fully close the jaw 110, the trigger 109 is squeezed in direction C to rotate the trigger plate 124 fully counterclockwise to straighten the toggle clamp 145 and advanced the yoke 132. To fully fire the knife while the lockout defeat mechanism 108 disabled, e.g., in the "OFF" position (in other words, the lockout mechanism is enabled) the energy button 122 must be depressed to rotate the lockout element 165 counterclockwise and rotate the unlock arm 119 clockwise to kick the lock arm 157 out of the notch 158 in the rack 136 and unlock the lockout mechanism. Once the lockout mechanism in unlocked, the trigger 109 can be fully squeezed in direction C to rotate the firing plate 128 counterclockwise. This rotates the first pinion 133 clockwise, the second pinion 134 counterclockwise, and the rack 136 is driven distally to fire the firing bar 117 distally in direction H to fire the knife 174 and the I-beam member 216. FIG. 35 is a partial perspective view of the surgical instrument 102 shown in FIG. 34, according to one embodiment. This view shows the energy button 122 depressed to rotate the lockout element 165 counterclockwise, which in turn rotates the unlock arm 119 clockwise to unlock the unlock arm 119 unlocking the lock arm 157 and enabling the rack 136 to fire the firing bar 117 and the knife.

Figure 36:
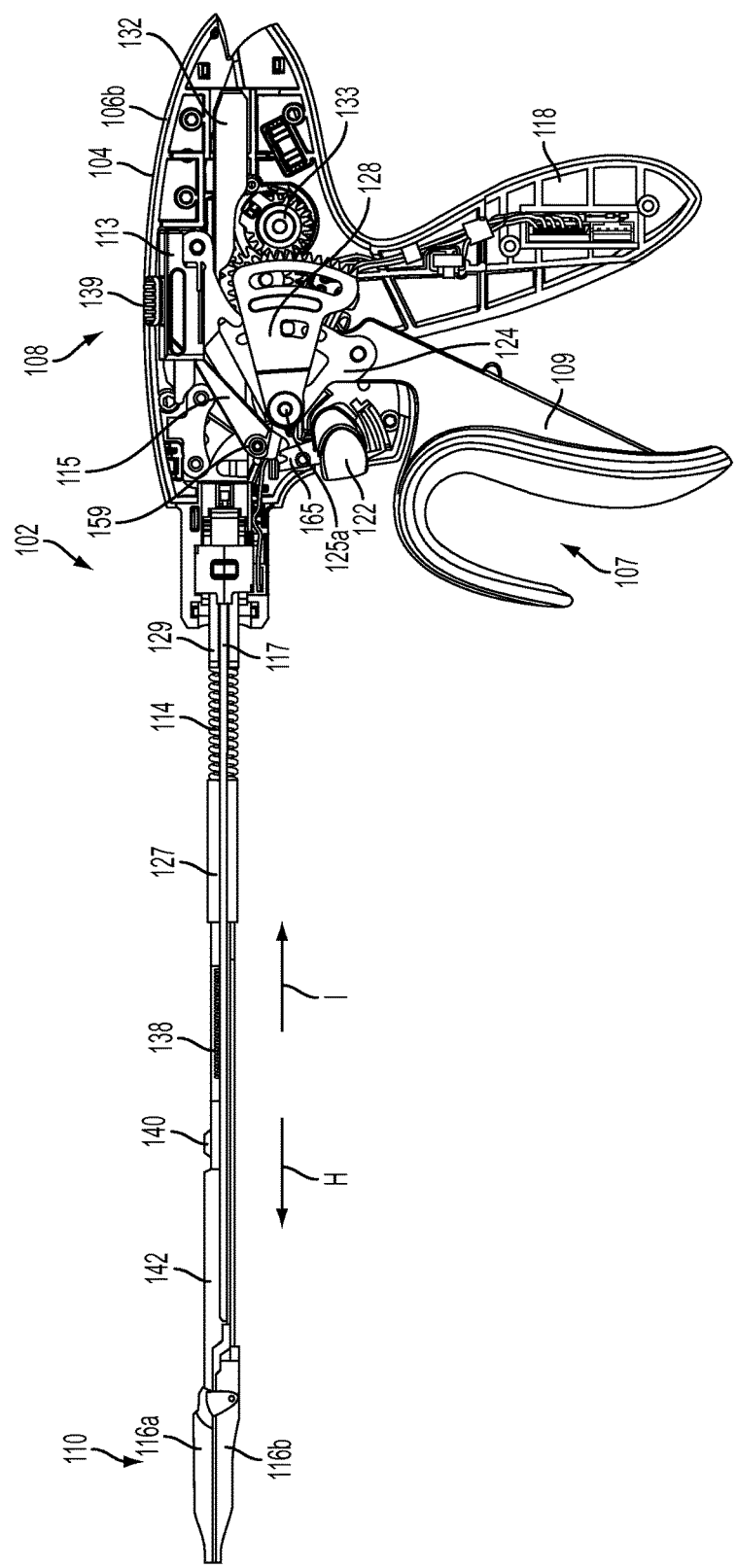
FIG. 36 is a side elevational view of the surgical instrument shown in FIGS. 1 and 2 with the left housing shroud removed, shaft assembly sheaths removed, jaw clamped, and the lockout defeat mechanism enabled, e.g., in the "ON" position, according to one embodiment.
Figure 37:
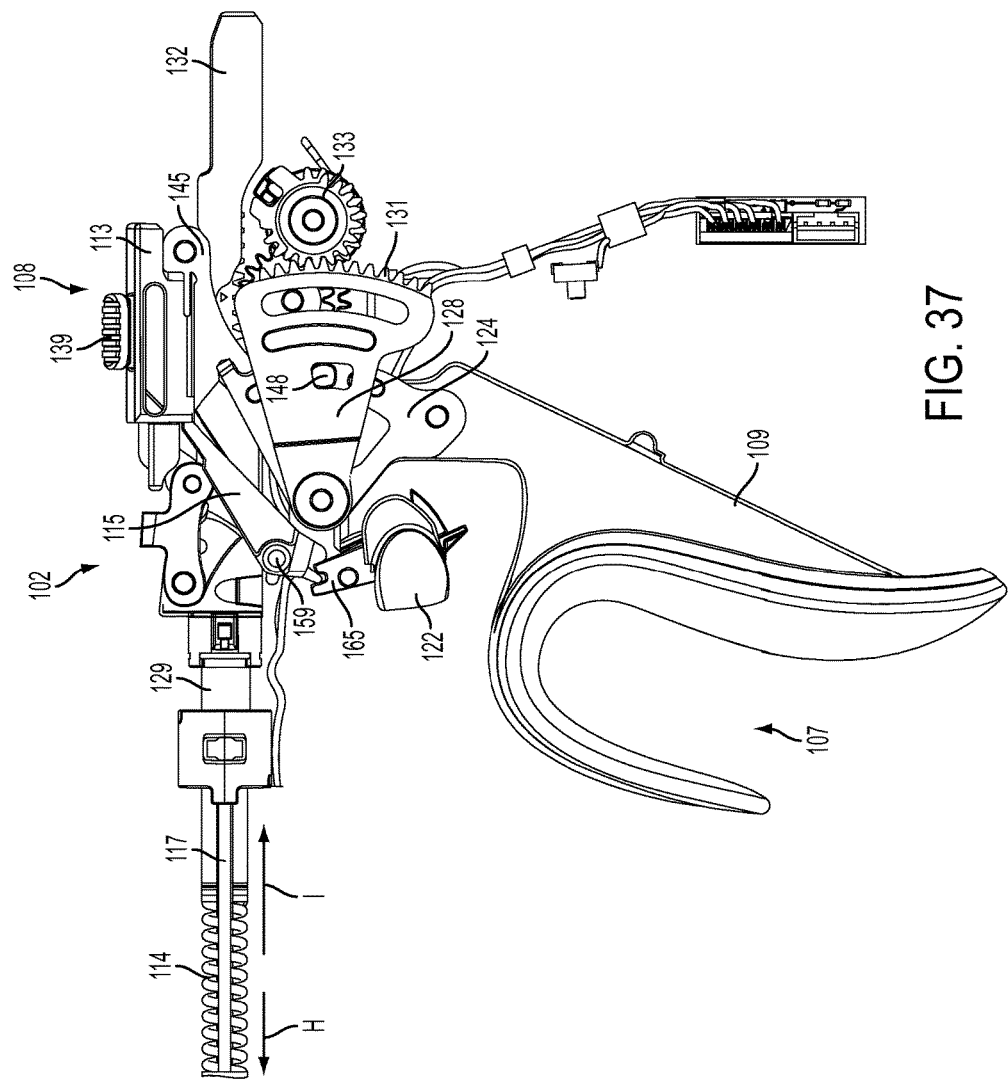
FIG. 37 is a side elevational view of the surgical instrument shown in FIG. 36 with the right housing shroud removed, according to one embodiment.
Figure 38:
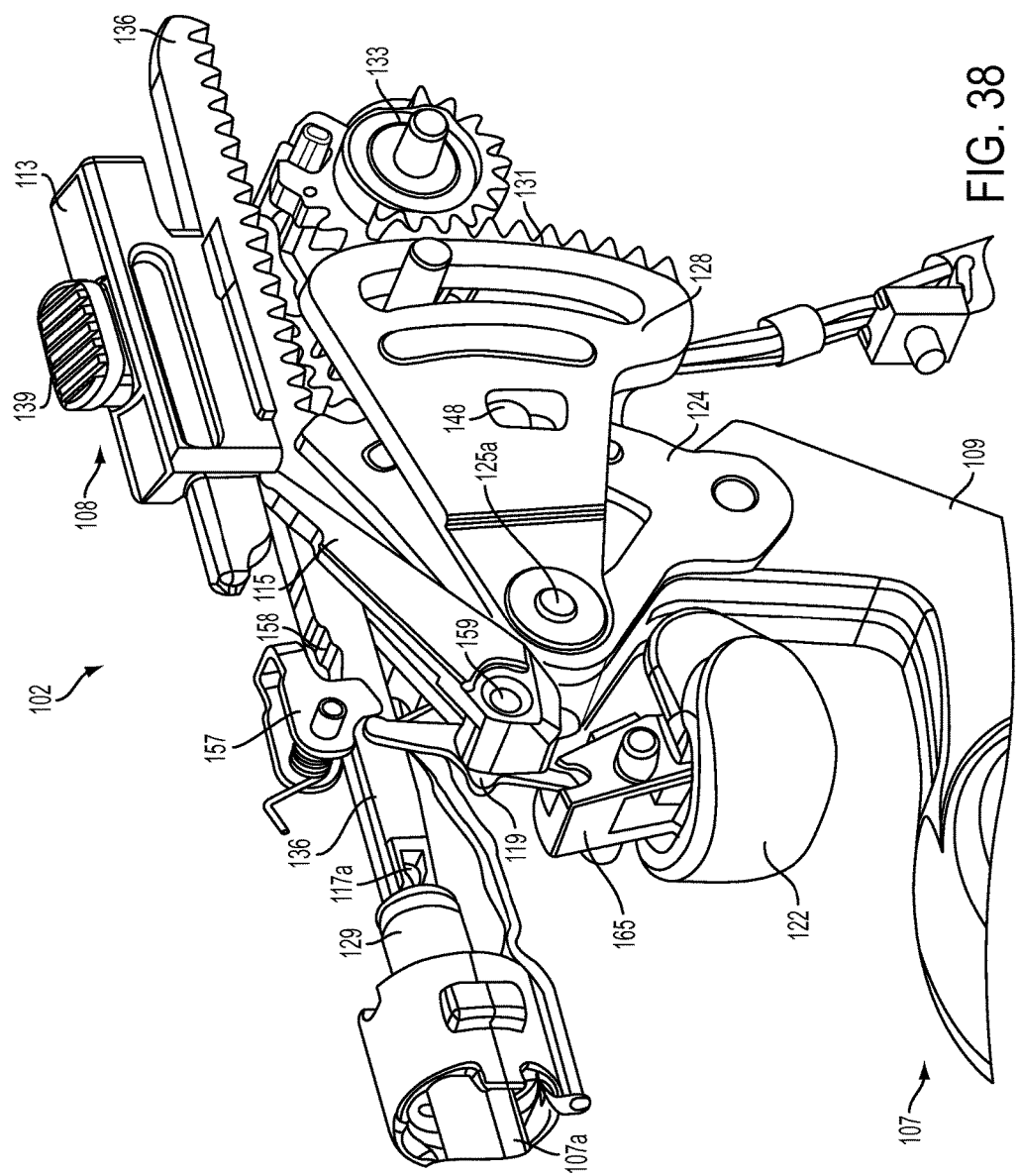
FIG. 38 is a partial perspective view of the surgical instrument shown in FIG. 37, according to one embodiment.

FIGS. 36-38 illustrate the surgical instrument 102 shown in FIGS. 1 and 2 with the jaw 110 fully closed or clamped and the lockout defeat mechanism 108 enabled, e.g., in the "ON" position. FIG. 36 is a side elevational view of the surgical instrument 102 shown in FIGS. 1 and 2 with the left housing 106a shroud removed, shaft assembly 112 sheaths removed, the jaw 110 clamped and the lockout defeat mechanism 108 enabled, e.g., in the "ON" position, according to one embodiment. FIG. 37 is a side elevational view of the surgical instrument 102 shown in FIG. 36 with the right housing shroud 106b removed, according to one embodiment. In this view, the jaw 110 has been fully clamped but the knife has not yet been fired. Thus, the trigger plate 124 is fully rotated counterclockwise to straighten the toggle clamp 145 and drive the yoke 132 distally in direction H. Since the knife 174 has not been fired, the trigger 109 has not been fully squeezed and the firing plate 128 has not been rotated to actuate the rack 136. FIG. 38 is a partial perspective view of the surgical instrument 102 shown in FIG. 37, according to one embodiment. With the lockout defeat mechanism 108 enabled, e.g., in the "ON" position, when the jaw 110 is clamped, the lock arm 157 is unlocked by the unlock arm 119 when the toggle clamp 145 and the yoke 132 are advanced distally in direction H. As shown, the lock arm 157 has been disengaged from the notch 158 in the rack 136 to enable the rack 136 to drive the firing bar 117 and the knife without the need to first depress the energy button 122.

Figure 39:
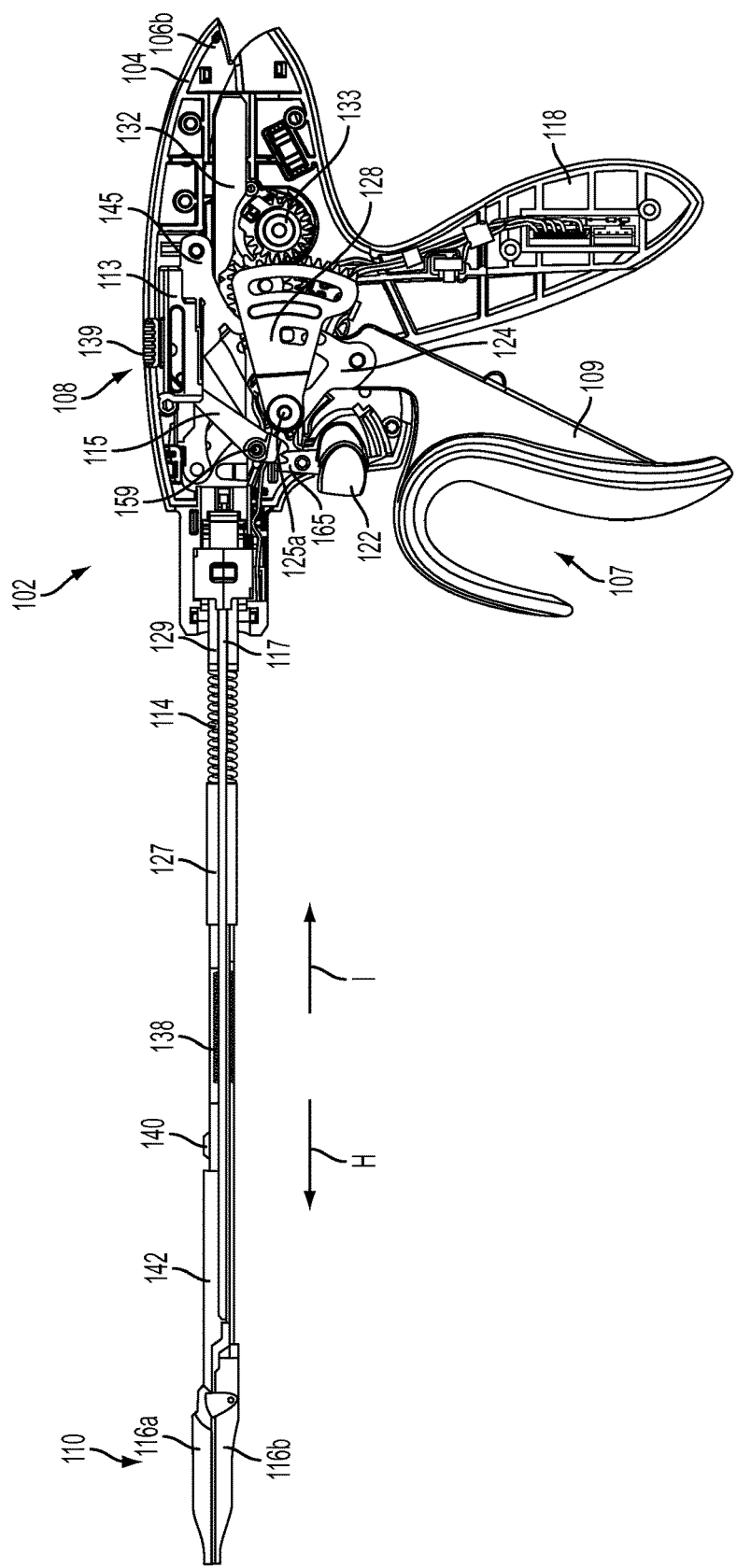
FIG. 39 is a side elevational view of the surgical instrument shown in FIGS. 1 and 2 with the left housing shroud removed, shaft assembly sheaths removed, jaw clamped and the lockout defeat mechanism disabled, e.g., in the "OFF" position, according to one embodiment.
Figure 40:
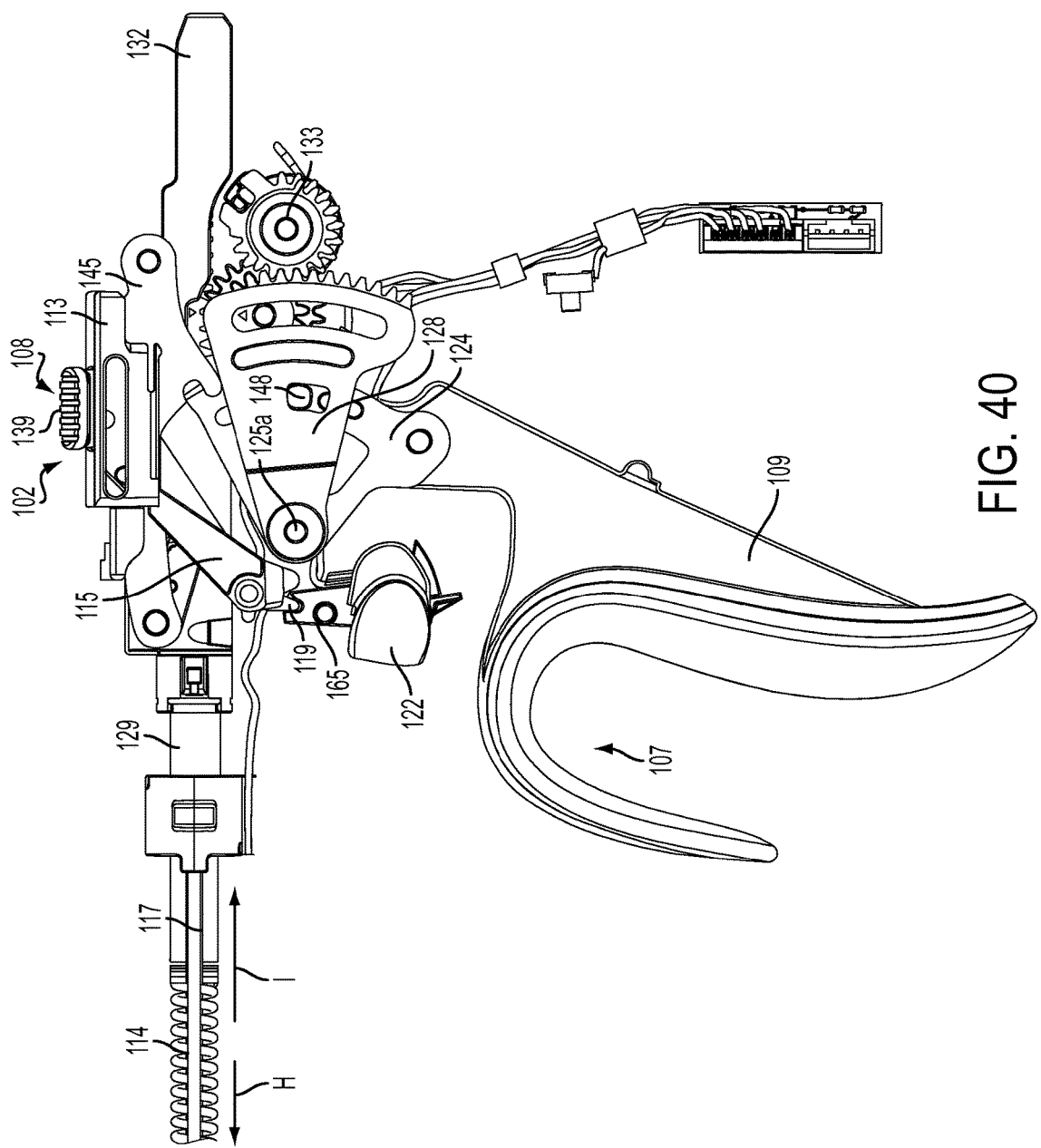
FIG. 40 is a side elevational view of the surgical instrument shown in FIG. 39 with the right housing shroud removed, according to one embodiment.
Figure 41:
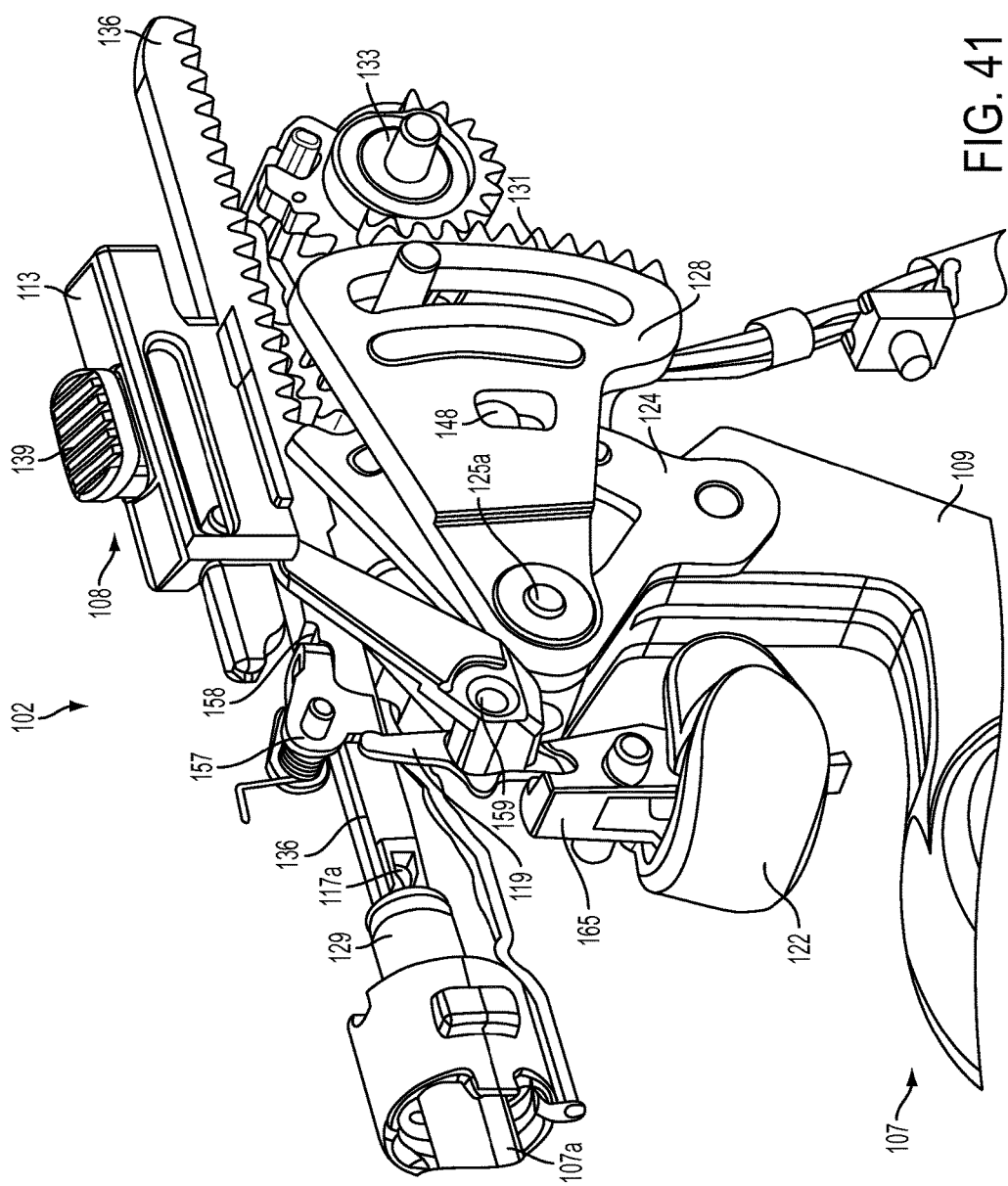
FIG. 41 is a partial perspective view of the surgical instrument shown in FIG. 40, according to one embodiment.

FIGS. 39-41 illustrate the surgical instrument 102 shown in FIGS. 1 and 2 with the jaw 110 fully closed clamped position and the lockout defeat mechanism 108 disabled, e.g., in the "OFF" position. FIG. 39 is a side elevational view of the surgical instrument 102 shown in FIGS. 1 and 2 with the left housing shroud 106a removed, shaft assembly 112 sheaths removed, the jaw 110 clamped and the lockout defeat mechanism 108 disabled, e.g., in the "OFF" position, according to one embodiment. FIG. 40 is a side elevational view of the surgical instrument 102 shown in FIG. 39 with the right housing shroud 106b removed, according to one embodiment. In this view, the jaw 110 has been fully clamped but the knife has not yet been fired. Thus, the trigger plate 124 is fully rotated counterclockwise to straighten the toggle clamp 145 and drive the yoke 132 distally in direction H. Since the knife has not been fired, the trigger 109 has not been fully squeezed and the firing plate 128 has not been rotated to actuate the rack 136. FIG. 41 is a partial perspective view of the surgical instrument 102 shown in FIG. 40, according to one embodiment. With the lockout defeat mechanism 108 disabled, e.g., in the "OFF" position, when the jaw 110 is clamped, the lock arm 157 is located in the notch 158 formed in the rack 136 to prevent the rack 136 from advancing distally in direction H. As shown, the energy button 122 has not been depressed to unlock the lockout mechanism, thus when the toggle clamp 145 and the yoke 132 are advanced distally in direction H, the unlock arm 116 is positioned substantially vertically relative to the lock arm 157 and cannot disengage it from the notch 158. As shown, the lock arm 157 is still engaged in the notch 158 formed of the rack 136 to disable the rack 136 from driving the firing bar 117 and the knife without first depressing the energy button 122 to unlock the lockout mechanism.

Figure 42:
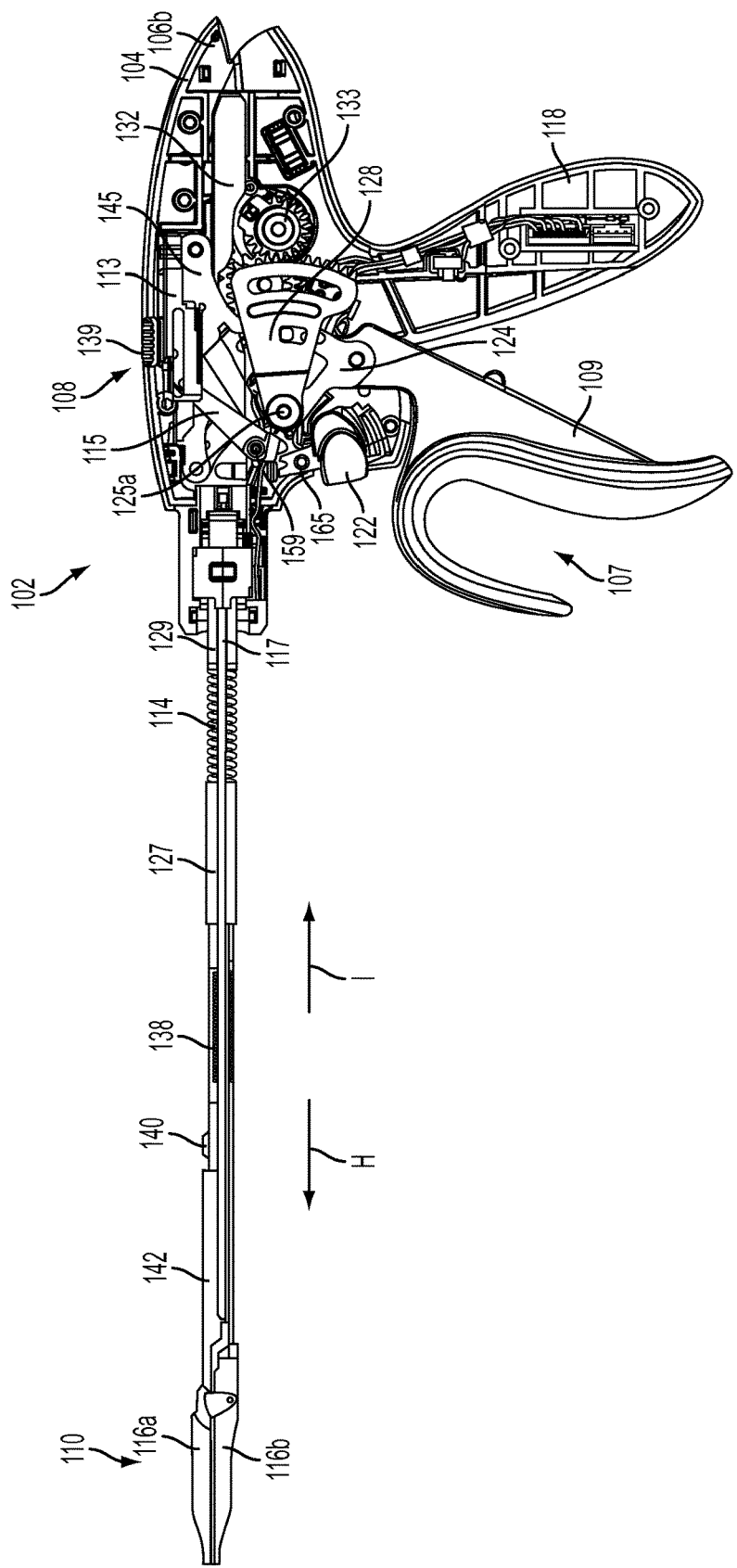
FIG. 42 is a side elevational view of the surgical instrument shown in FIGS. 1 and 2 with the left housing shroud removed, shaft assembly sheaths removed, jaw clamped and the energy button thrown to unlock the lockout mechanism, according to one embodiment.
Figure 43:
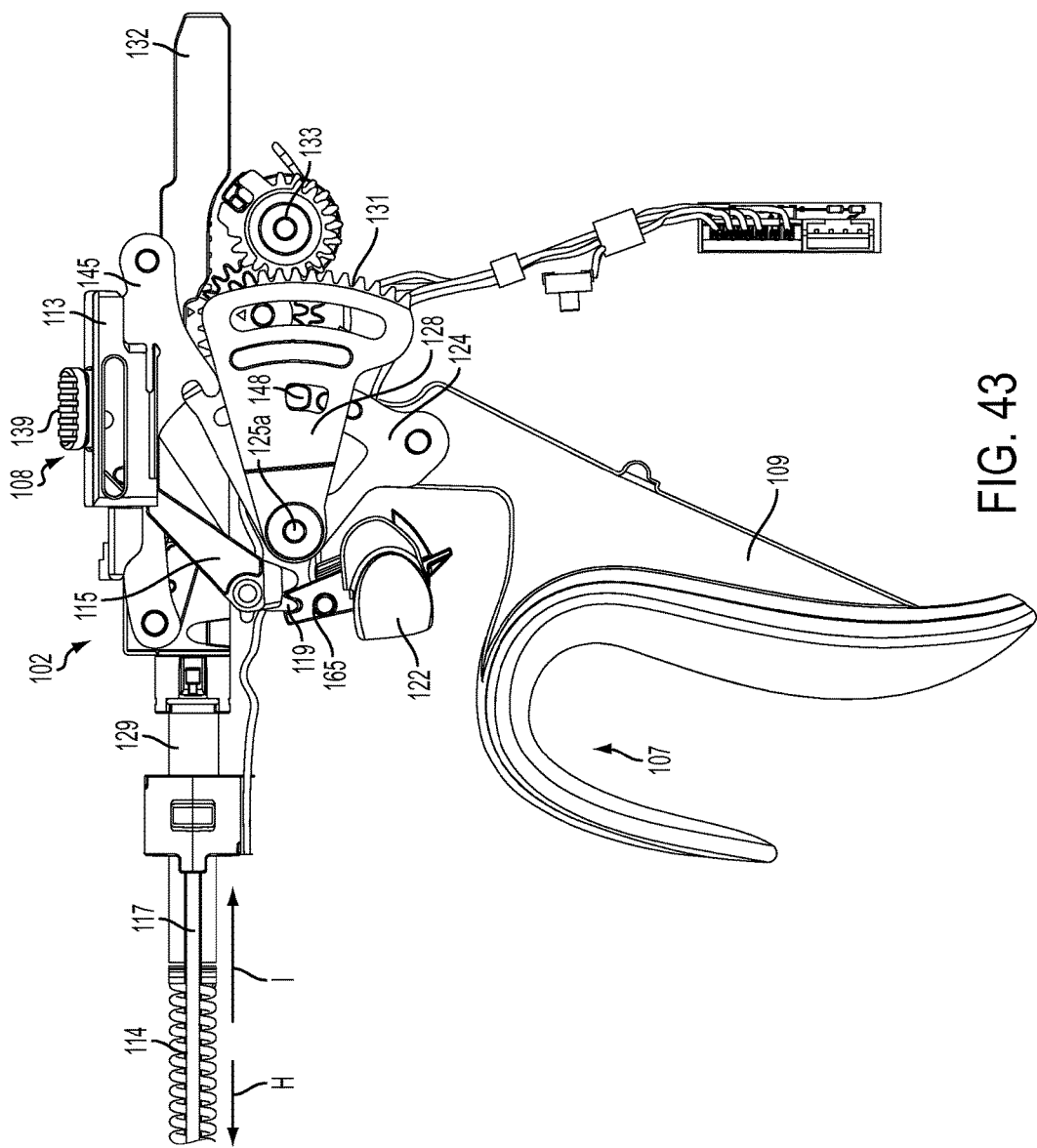
FIG. 43 is a side elevational view of the surgical instrument shown in FIG. 42 with the right housing shroud removed, according to one embodiment.
Figure 44:
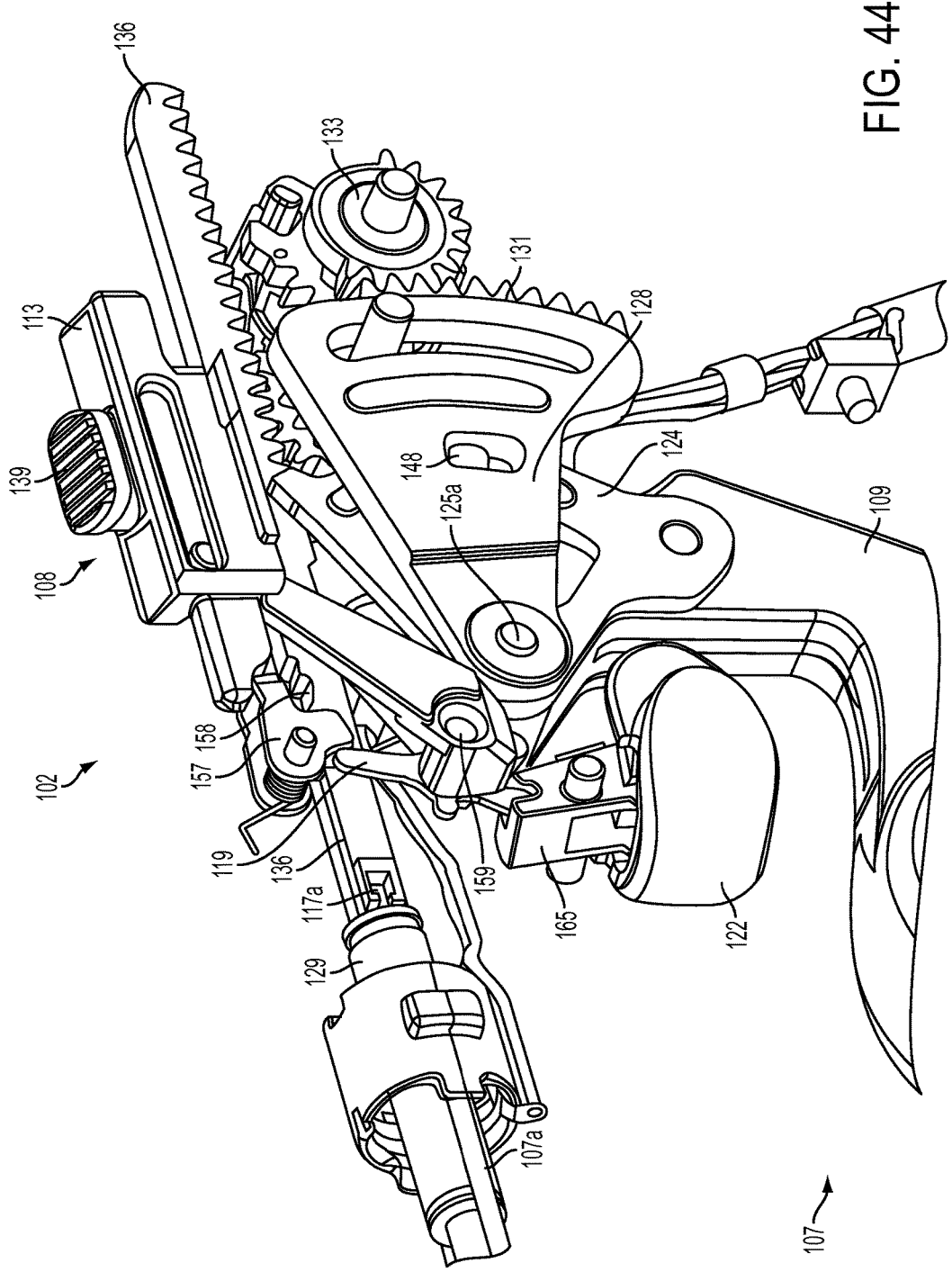
FIG. 44 is a partial perspective view of the surgical instrument shown in FIG. 43, according to one embodiment.

FIGS. 42-44 illustrate the surgical instrument 102 shown in FIGS. 1 and 2 with the jaw 110 clamped and the energy button 122 thrown to unlock the lockout mechanism. FIG. 42 is a side elevational view of the surgical instrument 102 shown in FIGS. 1 and 2 with the left housing shroud 106a removed, shaft assembly 112 sheaths removed, the jaw 110 clamped and the energy button 122 thrown to unlock the lockout mechanism, according to one embodiment. FIG. 43 is a side elevational view of the surgical instrument 102 shown in FIG. 42 with the right housing shroud 106b removed, according to one embodiment. As shown, the trigger plate 128 has been rotated counterclockwise by the trigger 109. The firing plate 128, however, has not been actuated. The energy button 122 has been thrown or depressed to unlock the lockout mechanism. FIG. 44 is a partial perspective view of the surgical instrument 102 shown in FIG. 43, according to one embodiment. As shown, the lock arm 157 has been disengaged from the notch 158 formed in the rack 136 to enable the rack to advance distally in direction H when the trigger 109 is fully squeezed in direction C to actuate the firing plate 128.

Figure 45:
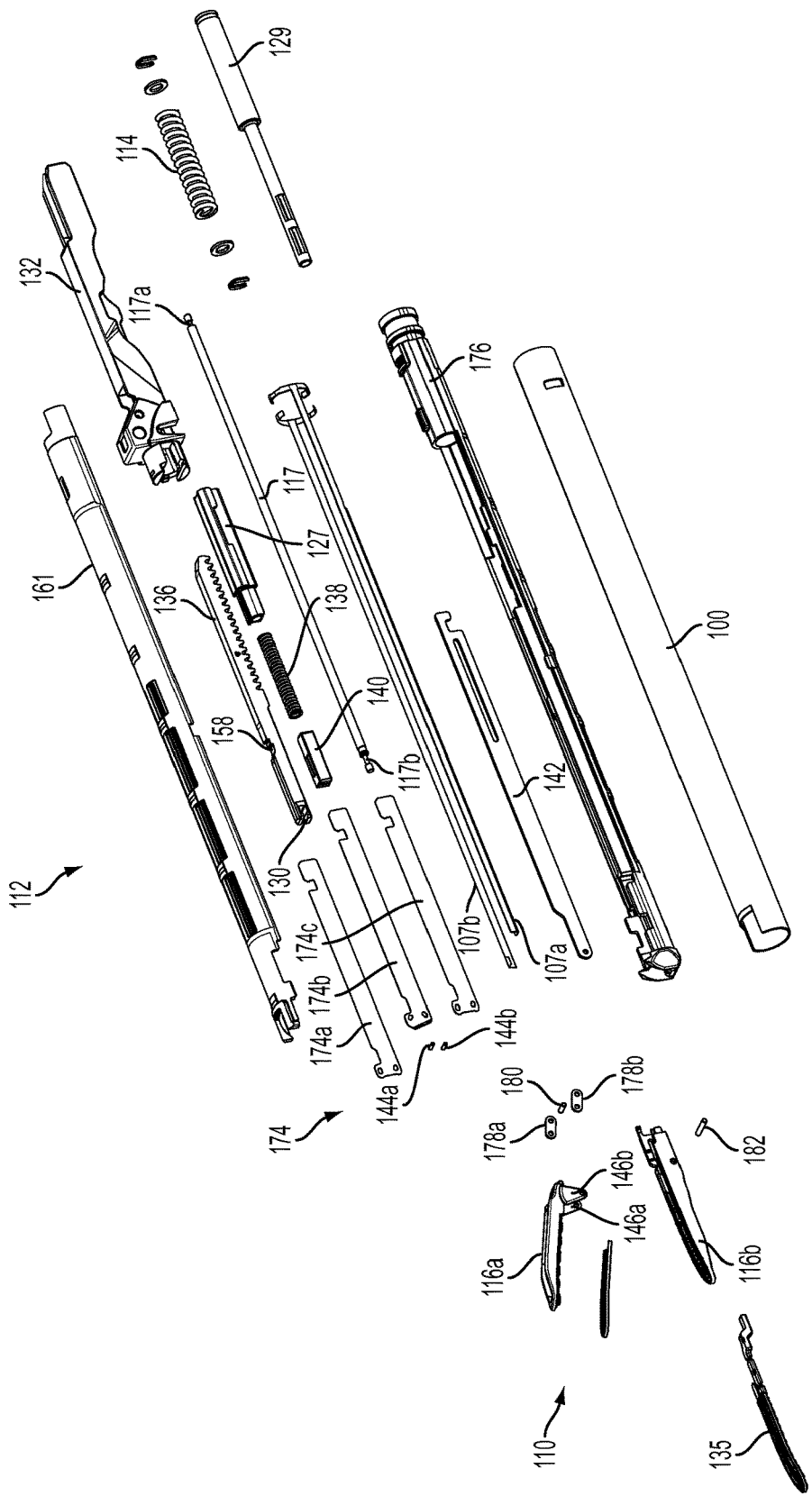
FIG. 45 is an exploded view of the shaft assembly, end effector, yoke, and rack portions of the surgical instrument shown in FIGS. 1 and 2, according to one embodiment.
Figure 46:
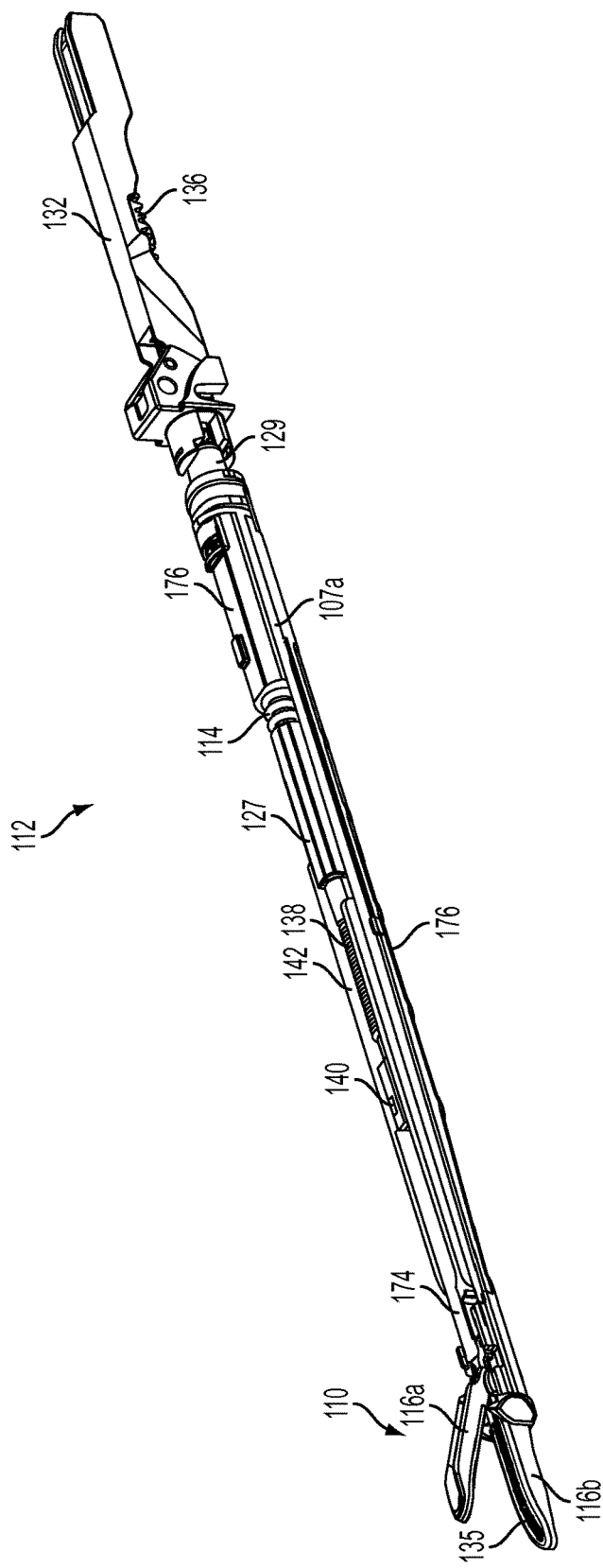
FIG. 46 is a perspective view of the shaft assembly, end effector, yoke, and rack shown in FIG. 45 in the assembled state, according to one embodiment.

FIG. 45 is an exploded view of the shaft assembly 112, end effector 110, yoke 132, and rack 136 portions of the surgical instrument shown in FIGS. 1 and 2, according to one embodiment. FIG. 46 is a perspective view of the shaft assembly 112, end effector 110, yoke 132, and rack 136 in the assembled state according to one embodiment showing the functional components. With reference now to FIGS. 45-46, the shaft assembly 112 comprises an outer tube 100 which contains or houses the various functional components of the shaft assembly 112. An electrically insulative nonconductive tube 176 is slidably received within the outer tube 100. A clamp tube 161 is attached to the non conductive tube 176. The functional components of the shaft assembly 112 are slidably contained within the within the nonconductive tube 176 whereas the conductive elements 107a, 107b employed to supply electrical energy to the end effector 110 electrodes 135 are located outside the nonconductive tube 176. A closure actuator 129 is coupled to the distal end of the yoke 132. The closure actuator 129 comprises a proximal portion and a distal portion. The distal portion of the closure actuator 129 is sized to be received within a closure spring 114. The proximal portion of the closure actuator 129 is sized to compress the closure spring 114. The closure spring 114 is coupled to a closure bar 142 through a spring to bar interface element 127. The distal end 172 of the closure bar 142 is operatively coupled to the jaws 116a, 116b by a pin 180 and closure linkages 178a, 178b. The jaws 116a, 116b are pivotally coupled by a pin 182 and rotatable support structures 146a, 146b formed in the top jaw 116a. The closure actuator 129 is coupled to the distal end of the yoke 132, which is operatively coupled to the toggle clamp 145 (FIG. 10, for example). As previously described, the toggle clamp 145 is movably coupled to the trigger plate 124 (FIG. 10), for example. Rotation of the trigger plate 124 straightens the toggle clamp 145 to drive the yoke 132 distally. Distal movement of the yoke 132 causes distal movement of the closure actuator 129 to compress the closure spring 114 and drive the closure bar 142. Distal movement of the closure actuator 129 pivotally moves the first jaw member 116a from an open position to a closed position with respect to the second jaw member 116b, for example.

A firing bar 117 comprises a proximal end 117a and a distal end 117b. The proximal end 117a of the firing bar 117 is coupled to the distal end 130 of the rack 136. The rack 136 is received within the yoke 132. The firing bar 117 is received within the closure actuator 129, the spring to bar interface element 127, and the jaw open spring 138. The distal end 117b of the firing bar 117 is fixedly coupled to a knife pusher block 140, which is fixedly coupled to a cutting element 174 (knife). The cutting element 174 comprises flexible bands 174a, 174b, 174c, which are fastened by the knife pusher block 140 at the proximal end and by pins 144a, 144b at the distal end to form knife or cutting element having an I-beam configuration. As previously described, the teeth 131 of the sector gear of the firing plate 128 engage and rotate the pinions 133, 134, which drive the rack 136 distally. The rack 136 drives the firing bar 117, which in turn drives the flexible I-beam cutting element 174 when the lock arm 157 is disengaged from a notch 158 formed in the rack 136.

Figure 47:
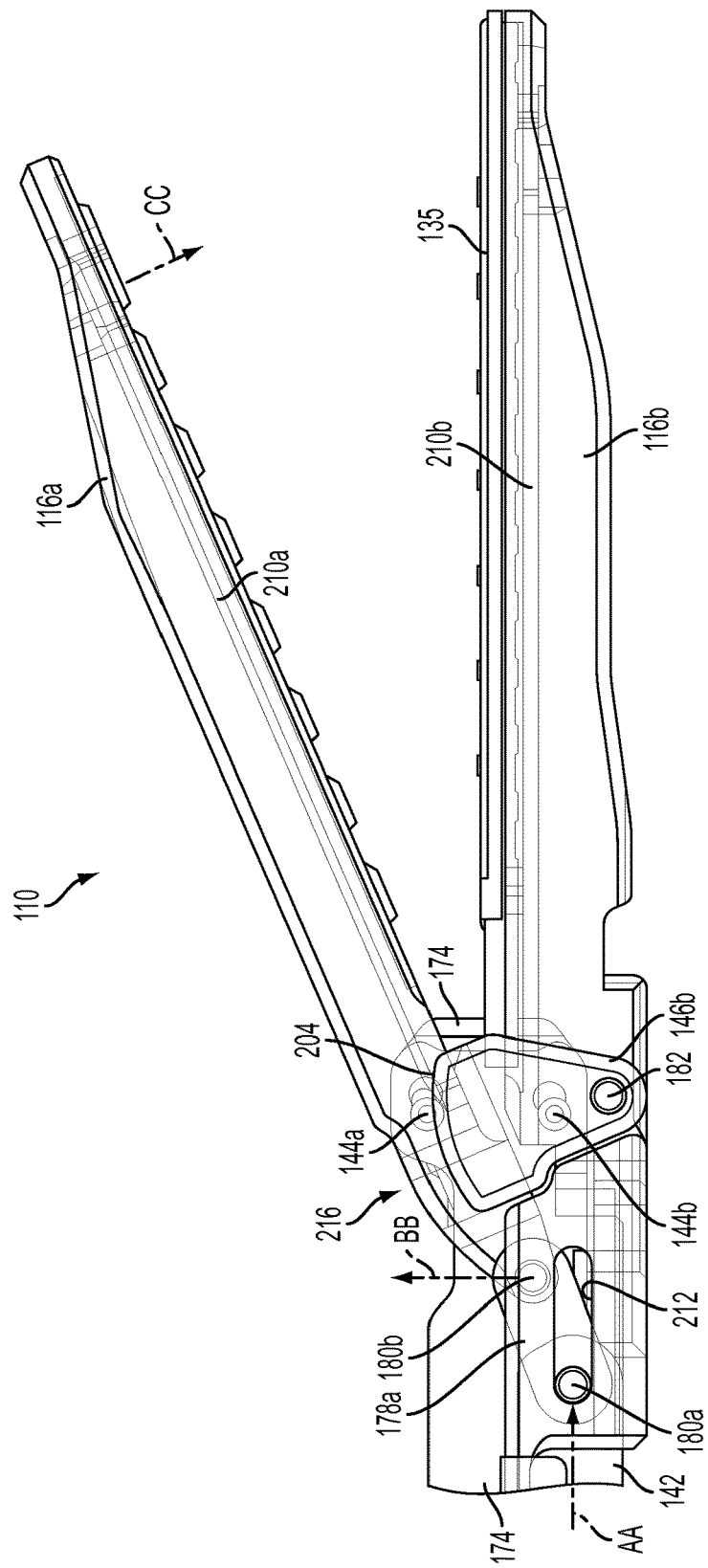
FIG. 47 is a side view of an end effector portion of the surgical instrument shown in FIGS. 1 and 2 with the jaws open, according to one embodiment.

FIG. 47 is a side view of an end effector 110 portion of the surgical instrument 102 shown in FIGS. 1 and 2 with the jaws open, according to one embodiment. The closure bar 142 is operatively coupled to the proximal end of the top jaw 116a via the closure linkages 178a, 178b (not shown) and first and second pins 180a, 180b. The lower pin 180a is slidably movable within a slot 212. As the closure bar 142 moves distally in the direction indicated by arrow AA, the pin 180a slides in the slot 212 to and forces the second pin 180b to move upwardly in the direction indicated by arrow BB to force the top jaw 116a to rotate to a closed position as indicated by arrow CC. The top jaw 116a pivots about a pivot point defined by the fastener pin 182. The bottom jaw 116b comprises the electrode 135, which is electrically coupled to an energy source (e.g., an RF electrosurgical energy source). The flexible 1-beam band knife comprises a knife or cutting element 174. The cutting element 174 and the fastener pins 144a, 144b form an 1-beam member 216 that forces the jaws 116a, 116b shut when the cutting element 174 is fired by the rack 136 and firing bar 117, as previously described. The 1-beam member 216 advances distally on tracks 210a, 210b formed in the respective upper and lower jaws 116a, 116b to force the jaws 116a, 116b shut and compress the tissue located therebetween. A ramp 204 is defined at the proximal end of the top track 210a in the top jaw 116a. Accordingly, a predetermined force is required to advance the 1-beam member 216 over the ramp 204 before the 1-beam member 216 engages the top track 210a to close the jaws 116a, 116b as the 1-beam member 216 is advanced distally by the flexible 1-beam band 174. In the present view, the 1-beam member 216 is located behind the ramp 204 as the linkages 178a, 178b (not shown) close the jaws 116a, 116b.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

The invention claimed is:

1. A surgical instrument, comprising:
 a handle assembly comprising:
  a trigger operatively coupled to a firing plate;
  an energy button configured to deliver energy to at least one electrode;
  a lockout element operatively coupled to the energy button, the lockout element configured to transition between an enabled position that prevents operation of the firing plate and a disabled position; and
  a lockout disabling mechanism configured to move relative to the lockout element between a first position and a second position, wherein when the lockout disabling mechanism is located in the first position, the lockout element can transition between the enabled position and the disabled position, and wherein when the lockout disabling mechanism moves to the second position, the lockout disabling mechanism engages the lockout element to hold the lockout element in the disabled position;
 wherein actuation of actuating the energy button transitions the lockout element from the enabled position to the disabled position when the lockout disabling mechanism is in the first position.

2. The surgical instrument of claim 1, wherein the lockout disabling mechanism comprises:
 a button slidably movable between the first position and the second position;
 a slider operatively coupled to the button, wherein the slider is slidably movable between the first position and the second position by the button; and a lever arm having a first end and a second end, the first end coupled to the slider and the second end coupled to the lockout element;

wherein the lever arm disables the lockout element when the slider is slidably moved from the first position to the second position.

3. The surgical instrument of claim 2, wherein the lockout disabling mechanism comprises a lock arm operatively coupled to the lever arm and the lockout element.

4. The surgical instrument of claim 2, wherein the slider comprises a ramped wall portion to engage the first end of the lever arm.

5. The surgical instrument of claim 2, wherein the slider comprises a detent to provide tactile feedback when locking and unlocking the lockout disabling mechanism.

6. The surgical instrument of claim 5, wherein the detent is configured to maintain the slider in a locked position.

7. The surgical instrument of claim 1, wherein the lockout disabling mechanism comprises:
a button rotatably movable between the first position and the second position;
a rotator operatively coupled to the button, wherein the rotator is rotatably movable between the first position and the second position by the button; and
a lever arm having a first end and a second end, the first end coupled to the rotator and the second end coupled to the lockout element;
wherein the lever arm disables the lockout element when the rotator is rotatably moved from the first position to the second position.

8. The surgical instrument of claim 7, wherein the lockout disabling mechanism comprises a lock arm operatively coupled to the lever arm and the lockout element.

9. The surgical instrument of claim 1, wherein the lockout disabling mechanism is operable independently of the energy button.

10. The surgical instrument of claim 1, wherein the disabled position of the lockout element permits operation of the firing plate.

11. A surgical instrument, comprising:
a handle assembly comprising:
a trigger operatively coupled to a trigger plate and a firing plate;
an energy button configured to deliver energy to at least one electrode;
a lockout element operatively coupled to the energy button, the lockout element configured to transition between an enabled position that prevents operation of the firing plate and a disabled position;
a lockout disabling mechanism configured to move relative to the lockout element between a first position and a second position, wherein when the lockout disabling mechanism is located in the first position, the lockout element can transition between the enabled position and the disabled position, and wherein when the lockout disabling mechanism moves to the second position, the lockout disabling mechanism engages the lockout element to hold the lockout element in the disabled position;
wherein actuation of the energy button transitions the lockout element from the enabled position to the disabled position when the lockout disabling mechanism is in the first position;
a shaft assembly comprising a proximal end and a distal end, wherein the shaft assembly is coupled to the handle assembly at the proximal end; and
an end effector coupled to the distal end of the shaft assembly, the end effector comprising:
a jaw assembly, comprising:
a first jaw member; and
a second jaw member, wherein rotation of the trigger plate transitions the jaw assembly between an open configuration and an approximated configuration by moving at least one of the first jaw member and the second jaw member relative to the other one of the first jaw member and the second jaw member; and
a cutting member deployable in response to rotation of the firing plate.

12. The surgical instrument of claim 11, wherein the lockout disabling mechanism comprises:
a button slidably movable between the first position and the second position;
a slider operatively coupled to the button, wherein the slider is slidably movable between the first position and the second position by the button; and
a lever arm having a first end and a second end, the first end coupled to the slider and the second end coupled to the lockout element;
wherein the lever arm disables the lockout element when the slider is slidably moved from the first position to the second position.

13. The surgical instrument of claim 12, wherein the lockout disabling mechanism comprises a lock arm operatively coupled to the lever arm and the lockout element.

14. The surgical instrument of claim 12, wherein the slider comprises a ramped wall portion to engage the first end of the lever arm.

15. The surgical instrument of claim 12, wherein the slider comprises a detent to provide tactile feedback when locking and unlocking the lockout disabling mechanism.

16. The surgical instrument of claim 15, wherein the detent is configured to maintain the slider in a locked position.

17. The surgical instrument of claim 11, wherein the lockout disabling mechanism comprises:
a button rotatably movable between the first position and the second position;
a rotator operatively coupled to the button, wherein the rotator is rotatably movable between the first position and the second position by the button; and
a lever arm having a first end and a second end, the first end coupled to the rotator and the second end coupled to the lockout element;
wherein the lever arm disables the lockout element when the rotator is rotatably moved from the first position to the second position.

18. The surgical instrument of claim 17, wherein the lockout disabling mechanism comprises a lock arm operatively coupled to the lever arm and the lockout element.

19. The surgical instrument of claim 11, wherein the lockout disabling mechanism is operable independently of the energy button.

20. The surgical instrument of claim 11, wherein the disabled position of the lockout element permits operation of the firing plate.

21. A surgical instrument, comprising:
an energy button;
a lockout mechanism configured to transition between an enabled position that prevents a cutting element from being fired and a disabled position; and
a lockout disabling mechanism configured to move relative to the lockout mechanism between a first position and a second position, wherein when the lockout disabling mechanism is located in the first position, the lockout mechanism can be transitioned between the enabled position and the disabled position, and wherein when the lockout disabling mechanism is moved to the second position, the lockout disabling mechanism engages the lockout mechanism to hold the lockout mechanism in the disabled position;

wherein actuation of the energy button transitions the lockout mechanism from the enabled position to the disabled position when the lockout disabling mechanism is in the first position.

22. The surgical instrument of claim 21, wherein the lockout disabling mechanism comprises:

a button slidably movable between the first position and the second position;

a slider operatively coupled to the button, wherein the slider is slidably movable between the first position and the second position by the button; and a lever arm having a first end and a second end, the first end coupled to the slider and the second end coupled to the lockout mechanism;

wherein the lever arm disables the lockout mechanism when the slider is slidably moved from the first position to the second position.

23. The surgical instrument of claim 22, wherein the lockout disabling mechanism comprises a lock arm operatively coupled to the lever arm and the lockout mechanism;

wherein the slider comprises a ramped wall portion to engage the first end of the lever arm;

wherein the slider comprises a detent to provide tactile feedback when locking and unlocking the lockout disabling mechanism; and wherein the detent is configured to maintain the slider in a locked position.

24. The surgical instrument of claim 21, wherein the lockout disabling mechanism comprises:

a button rotatably movable between the first position and the second position;

a rotator operatively coupled to the button, wherein the rotator is rotatably movable between the first position and the second position by the button; and a lever arm having a first end and a second end, the first end coupled to the rotator and the second end coupled to the lockout mechanism;

wherein the lever arm disables the lockout mechanism when the rotator is rotatably moved from the first position to the second position.

25. The surgical instrument of claim 21, wherein the lockout disabling mechanism is operable independently of the energy button.

26. The surgical instrument of claim 21, wherein the disabled position of the lockout mechanism permits the cutting element to be fired.

* * * * *